United States Patent
Small et al.

(10) Patent No.: US 11,667,590 B2
(45) Date of Patent: Jun. 6, 2023

(54) ETHYLENE OLIGOMERIZATION PROCESSES

(71) Applicant: Chevron Phillips Chemical Company LP, The Woodlands, TX (US)

(72) Inventors: Brooke L. Small, Kingwood, TX (US); Orson L. Sydora, Houston, TX (US); Ronald D. Knudsen, Saratoga Springs, UT (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 0 days.

(21) Appl. No.: 17/330,523

(22) Filed: May 26, 2021

(65) Prior Publication Data

US 2022/0380274 A1 Dec. 1, 2022

(51) Int. Cl.
  *C07C 2/30* (2006.01)
  *B01J 31/12* (2006.01)
  *B01J 31/14* (2006.01)

(52) U.S. Cl.
  CPC ............ *C07C 2/30* (2013.01); *B01J 31/12* (2013.01); *B01J 31/128* (2013.01); *B01J 31/143* (2013.01); *C07C 2531/14* (2013.01); *C07C 2531/22* (2013.01)

(58) Field of Classification Search
  CPC ... C07C 2/30; C07C 2531/14; C07C 2531/22; B01J 31/12; B01J 31/128; B01J 31/143
  See application file for complete search history.

(56) References Cited

U.S. PATENT DOCUMENTS

| | | |
|---|---|---|
| 4,361,714 A | 11/1982 | Langer et al. |
| 4,377,720 A | 3/1983 | Langer |
| 4,396,788 A | 8/1983 | Langer, Jr. |
| 4,409,414 A | 10/1983 | Langer, Jr. |
| 4,410,750 A | 10/1983 | Langer, Jr. |
| 4,434,312 A | 2/1984 | Langer, Jr. |
| 4,434,313 A | 2/1984 | Langer, Jr. |
| 4,442,309 A | 4/1984 | Langer, Jr. |
| 4,486,615 A | 12/1984 | Langer, Jr. |

(Continued)

FOREIGN PATENT DOCUMENTS

| | | |
|---|---|---|
| EP | 0320571 A2 | 6/1989 |
| EP | 0 328 728 | 8/1989 |

(Continued)

OTHER PUBLICATIONS

Sekiyu Gakkaishi, Development of α-Olefin Production Catalyst and Its Process, vol. 37, No. 4, 1994, pp. 337-346 (with English summary).

(Continued)

*Primary Examiner* — Ali Z Fadhel
(74) *Attorney, Agent, or Firm* — Merchant & Gould P.C.

(57) ABSTRACT

Process for producing alpha olefins comprising contacting ethylene, a zirconium based catalyst system comprising, a hydrocarbylmetal compound, a chain transfer agent, and optionally an organic reaction medium. Chain transfer agents which can be utilized include a) hydrogen, b) a compound comprising a hydrogen silicon bond, a compound having a hydrogen sulfur bond, a compound having a hydrogen phosphorus bond, or c) a transition metal compound chain transfer agent.

11 Claims, 1 Drawing Sheet

(56) References Cited

U.S. PATENT DOCUMENTS

| | | | |
|---|---|---|---|
| 4,783,573 A * | 11/1988 | Shiraki | C07C 2/36 585/511 |
| 4,855,525 A | 8/1989 | Young et al. | |
| 4,886,933 A | 12/1989 | Shiraki et al. | |
| 4,966,874 A | 10/1990 | Young et al. | |
| 5,260,500 A * | 11/1993 | Shiraki | C07C 2/30 585/524 |
| 6,492,473 B1 * | 12/2002 | Canich | C08F 10/00 526/170 |
| 6,576,721 B2 | 6/2003 | Kobayashi et al. | |
| 7,169,961 B2 | 1/2007 | Kobayashi et al. | |
| 7,291,685 B2 | 11/2007 | Kobayashi et al. | |
| 7,566,679 B2 | 7/2009 | Bölt et al. | |
| 7,897,826 B2 | 3/2011 | Fritz et al. | |
| 8,269,055 B2 | 9/2012 | Fritz et al. | |
| 2002/0147375 A1 * | 10/2002 | Tembe | C07C 2/30 585/521 |
| 2003/0153798 A1 | 8/2003 | Kobayashi et al. | |
| 2005/0070425 A1 * | 3/2005 | Biagini | B01J 31/143 502/103 |
| 2009/0216057 A1 | 8/2009 | Fritz et al. | |
| 2009/0306312 A1 | 12/2009 | Fritz et al. | |
| 2009/0306449 A1 * | 12/2009 | Aliyev | C07C 2/30 502/117 |
| 2010/0191029 A1 | 7/2010 | Fritz et al. | |
| 2010/0292423 A1 | 11/2010 | Aliyev et al. | |
| 2011/0046429 A1 | 2/2011 | Aliyev et al. | |
| 2011/0054130 A1 | 3/2011 | Aliyev et al. | |
| 2011/0054233 A1 | 3/2011 | Mousa et al. | |
| 2012/0184692 A1 | 7/2012 | Fritz et al. | |
| 2017/0081257 A1 | 3/2017 | Kreischer | |
| 2020/0055799 A1 | 2/2020 | Nadler et al. | |
| 2020/0055800 A1 | 2/2020 | Weber et al. | |
| 2020/0062672 A1 | 2/2020 | Weber et al. | |
| 2020/0062673 A1 | 2/2020 | Weber et al. | |
| 2021/0178376 A1 * | 6/2021 | Singh | C07C 2/32 |

FOREIGN PATENT DOCUMENTS

| | | | |
|---|---|---|---|
| EP | 0444505 A2 | 2/1990 | |
| EP | 1749807 A1 | 2/2007 | |
| EP | 1752434 A1 | 2/2007 | |
| EP | 1 759 766 | 3/2007 | |
| EP | 1780189 A1 | 5/2007 | |
| EP | 2258674 A1 | 12/2010 | |
| JP | 0444505 A2 * | 2/1991 | C07C 2/32 |
| WO | WO 91/02707 | 3/1991 | |
| WO | WO 2009/074203 | 6/2009 | |

OTHER PUBLICATIONS

Sekiyu Gakkaishi, Synthesis of α-Olefin by Oligomerization of Ethylene (Part 2) Study of the Mechanism of By-product Formation, vol. 42, No. 4, 1999, pp. 235-245 (with English summary).

Sekiyu Gakkaishi, Synthesis of α-Olefin by Oligomerization of Ethylene (Part 3) Development of Three Components Catalyst Consisting of Zirconiumtetrachloride, Ethylaluminumsesquichloride and Triethylaluminum, vol. 43, No. 5, 2000, pp. 328-338 (with English summary).

Sekiyu Gakkaishi, Synthesis of α-Olefin by Oligomerization of Ethylene (Part 4) Effects of Solvent and Additional Component as Ligand, vol. 44, No. 1, 2001, pp. 25-35 (with English summary).

Sekiyu Gakkaishi, Synthesis of α-Olefin by Oligomerization of Ethylene (Part 5) Post-treatment of Catalysts, vol. 44, No. 2, 2001, pp. 109-119 (with English translation).

Invitation to Pay Additional Fees and, Where Applicable, Protest Fee of the International Searching Authority in PCT/US2022/027448 dated Oct. 27, 2022, 13 pages.

International Search Report of the International Searching Authority in PCT/US2022/027448 dated Dec. 19, 2022, 6 pages.

Written Opinion of the International Searching Authority in PCT/US2022/027448 dated Dec. 19, 2022, 12 pages.

Cetinkaya et al, "Effect of the different chain transfer agents on molecular weight and optical properties of poly(methyl methacrylate)", Optical Materials, vol. 70, (2017), pp. 25-30, DOI: 10.1016/j.optmat.2017.05.009.

Khamiyev et al, "Zirconium Catalyzed Ethylene Oligomerization", Applied Organometallic Chemistry, vol. 34, No. 3, (2020), pp. 1-22, DOI: 10.1002/aoc.5409.

Sydora, "Selective Ethylene Oligomerization", Organometallics, vol. 38, No. 5, (2019), pp. 997-1010, DOI: 10.1021/acs.organomet.8b00799.

* cited by examiner

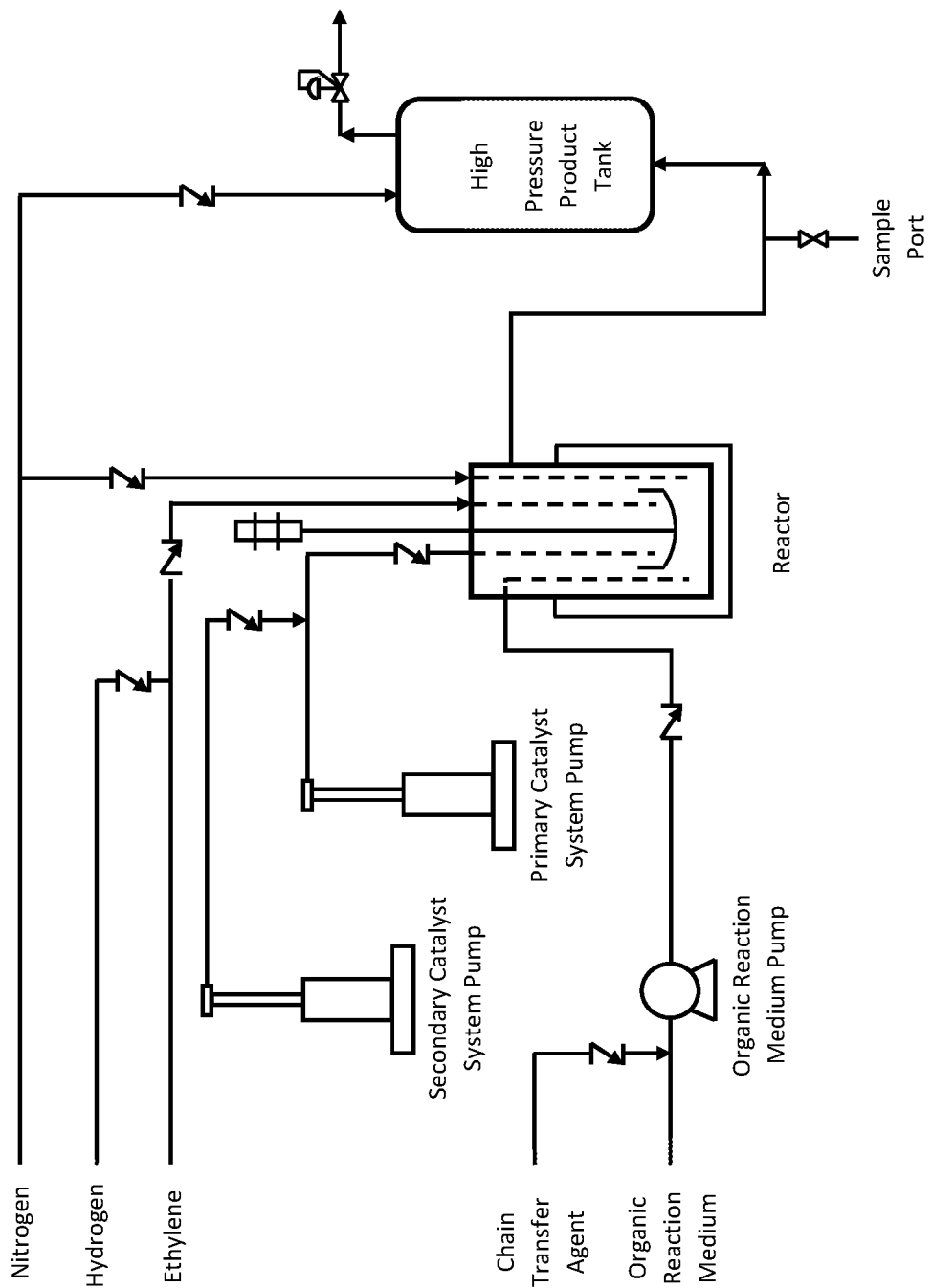

ETHYLENE OLIGOMERIZATION PROCESSES

FIELD OF THE INVENTION

The present disclosure relates to processes for producing normal alpha olefins. More particularly, the present disclosure relates to improved processes for oligomerizing ethylene to normal alpha olefins.

BACKGROUND OF THE INVENTION

Alpha olefins are important items of commerce. Their many applications include employment as intermediates in the manufacture of detergents, as precursors to more environmentally friendly refined oils, as monomers, and as precursors for many other types of products. One method of making alpha olefins is via oligomerization of ethylene in a catalytic reaction involving various types of catalysts and/or catalyst systems. Some ethylene oligomerization catalyst systems produce significant quantities of polymer which can reduce reaction system operation time before requiring reactor cleaning, reduce reaction system reliability, and/or complicate product isolation. Applications and demand for normal alpha olefins continue to increase and competition to supply them correspondingly intensifies. Thus, novel and improved processes for ethylene oligomerization are desirable.

SUMMARY OF THE INVENTION

The present application relates to processes comprising: a) contacting i) ethylene, ii) a catalyst system comprising 1) a zirconium compound having the formula $ZrX^1_m Y^1_q$, where each $X^1$ independently is a halide, each $Y^1$ independently is a hydrocarboxide, a dihydrocarbylazanide, a hydrocarbylcarboxylate, a hydrocarbylsulfonate, or a β-diketonate, m is a range from 0 to 4, q is in a range from 0 to 4, and m+q is an integer from 2 to 4, and 2) a hydrocarbylmetal compound, iii) a chain transfer agent, and iv) optionally, an organic reaction medium; and b) forming an oligomer product in a reaction zone; and wherein the oligomer product has a Schulz-Flory K value from 0.4 to 0.8. In an aspect, the chain transfer agent can be i) a compound comprising a hydrogen silicon bond, a compound having a hydrogen sulfur bond, a compound having a hydrogen phosphorus bond, or any combination thereof, ii) hydrogen, or 3) a transition metal compound. In some aspects, the processes can produce an oligomer product comprising (a) less than 1 wt. % of polymer, (b) less than 1 wt. % compounds having a weight average molecular weight of greater than 1000 g/mol, or (c) any combination thereof wherein the wt. % is based on the total weight of the oligomer product. In another aspect, the processes can produce an oligomer product comprising (a) polymer having a lower Mw, (b) a polymer having a lower Mw maximum peak, (c) a reduced percentage of polymer, (d) a polymer having a reduced percentage of polymer having a Mw greater than 100,000, or (e) any combination thereof relative to the same process not using the chain transfer agent comprising a compound having a hydrogen silicon bond, a compound having a hydrogen sulfur bond, a compound having a hydrogen phosphorus bond, or any combination thereof.

BRIEF DESCRIPTION OF THE DRAWING

The patent application subject matter can be understood by reference to the following description taken in conjunction with the accompanying drawings, in which like reference numerals identify like elements, and in which:

FIG. 1 illustrates an example of an ethylene oligomerization apparatus.

While the patent application subject matter is susceptible to various modifications and alternative forms, the drawing illustrates specific embodiments herein described in detail by way of example. It should be understood, however, that the description herein of specific embodiments is not intended to limit the claimed subject matter to the particular forms disclosed, but on the contrary, the intention is to cover all modifications, equivalents, and alternatives falling within the spirit and scope of the invention as defined by the appended claims.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter can be described such that, within particular aspects and/or statements, a combination of different features can be envisioned. For each and every aspect, and/or statement, and/or feature disclosed herein, all combinations that do not detrimentally affect the systems, compositions, processes, and/or methods described herein are contemplated with or without explicit description of the particular combination. Additionally, unless explicitly recited otherwise, any aspect, and/or statement, and/or feature disclosed herein can be combined to describe inventive processes and systems consistent with the present disclosure.

The terms "a," "an," and "the" are intended, unless specifically indicated otherwise, to include plural alternatives, e.g., at least one, or one or more. For instance, the disclosure of "a trialkylaluminum compound" is meant to encompass one trialkylaluminum compound, or mixtures or combinations of more than one trialkylaluminum compound unless otherwise specified.

Groups of elements of the periodic table are indicated using the numbering scheme found in the version of the periodic table of elements published in Chemical and Engineering News, 63(5), 27, 1985. In some instances, a group of elements can be indicated using a common name assigned to the group; for example alkali metals for Group 1 elements, alkaline earth metals for Group 2 elements, transition metals for Group 3-12 elements, and halogens for Group 17 elements, among others.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to a $C_6$ hydrocarbon refers to all hydrocarbon having 6 carbon atoms, a general reference to pentane includes n-pentane, 2-methylbutane, and 2,2-dimethylpropane, and a general reference to a butyl group includes an n-butyl group, a sec-butyl group, an iso-butyl group, and a tert-butyl group. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogens atoms, as necessary for the situation, removed from the alkane. Throughout, the disclosure of a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "hydrocarbon" whenever used in this specification and claims refers to a compound containing only carbon and hydrogen. Other identifiers can be utilized to indicate the presence of particular groups in the hydrocarbon (e.g. halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g. halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl groups are derived by removal of a hydrogen atom from a primary, secondary, or tertiary carbon atom, respectively, of an alkane. The n-alkyl group can be derived by removal of a hydrogen atom from a terminal carbon atom of a linear alkane.

The term "substituted" when used to describe a compound or group, for example, when referring to a substituted analog of a particular compound or group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

The term "olefin" whenever used in this specification and claims refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc . . . carbon-carbon double bonds can be identified by use of the term "mono," "di," "tri," etc. . . . within the name of the olefin. The olefins can be further identified by the position of the carbon-carbon double bond(s).

The term "alpha olefin" as used in this specification and claims refers to an olefin that has a carbon-carbon double bond between the first and second carbon atoms of the longest contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of other carbon-carbon double bonds unless explicitly indicated. The term "linear alpha olefin" as used herein refers to a non-branched alpha olefin having a carbon-carbon double bond between the first and second carbon atom.

The term "normal alpha olefin" whenever used in this specification and claims refers to a linear aliphatic mono-olefin having a carbon-carbon double bond between the first and second carbon atoms. It is noted that "normal alpha olefin" is not synonymous with "linear alpha olefin" as the term "linear alpha olefin" can include linear olefinic compounds having a double bond between the first and second carbon atoms and additional double bonds.

A cycloalkane is a saturated cyclic hydrocarbon, with or without side chains, for example, cyclobutane. Unsaturated cyclic hydrocarbons having one or more endocyclic double or one triple bond are called cycloalkenes and cycloalkynes, respectively. Cycloalkenes and cycloalkynes having only one, only two, only three, etc. . . . endocyclic double or triple bonds, respectively, can be identified by use of the term "mono," "di," "tri, etc. . . . within the name of the cycloalkene or cycloalkyne. Cycloalkenes and cycloalkynes can further identify the position of the endocyclic double or triple bonds.

A "cycloalkyl group" is a univalent group derived by removing a hydrogen atom from a ring carbon atom of a cycloalkane. Similarly, a "cycloalkylene group" refers to a group derived by removing two hydrogen atoms from a cycloalkane, at least one of which is a ring carbon. Thus, a "cycloalkylene group" includes both a group derived from a cycloalkane in which two hydrogen atoms are formally removed from the same ring carbon, a group derived from a cycloalkane in which two hydrogen atoms are formally removed from two different ring carbons, and a group derived from a cycloalkane in which a first hydrogen atom is formally removed from a ring carbon and a second hydrogen atom is formally removed from a carbon atom that is not a ring carbon. A "cycloalkane group" refers to a generalized group formed by removing one or more hydrogen atoms (as necessary for the particular group and at least one of which is a ring carbon) from a cycloalkane. It should be noted that according to the definitions provided herein, general cycloalkane groups (including cycloalkyl groups and cycloalkylene groups) include those having zero, one, or more than one hydrocarbyl substituent groups attached to a cycloalkane ring carbon atom (e.g., a methylcyclopropyl group) and is a member of the group of hydrocarbon groups. However, when referring to a cycloalkane group having a specified number of cycloalkane ring carbon atoms (e.g., cyclopentane group or cyclohexane group, among others), the base name of the cycloalkane group having a defined number of cycloalkane ring carbon atoms refers to the unsubstituted cycloalkane group (including having no hydrocarbyl groups located on cycloalkane group ring carbon atom). Consequently, a substituted cycloalkane group having a specified number of ring carbon atoms (e.g., substituted cyclopentane or substituted cyclohexane, among others) refers to the respective group having one or more substituent groups (including halogens, hydrocarbyl groups, or hydrocarboxy groups, among other substituent groups) attached to a cycloalkane group ring carbon atom. When the substituted cycloalkane group having a defined number of cycloalkane ring carbon atoms is a member of the group of hydrocarbon groups (or a member of the general group of cycloalkane groups), each substituent of the substituted cycloalkane group having a defined number of cycloalkane ring carbon atoms is limited to hydrocarbyl substituent group. One can readily discern and select general groups, specific groups, and/or individual substituted cycloalkane group(s) having a specific number of ring carbons atoms which can be utilized as member of the hydrocarbon group (or a member of the general group of cycloalkane groups).

An aliphatic compound is an acyclic or cyclic, saturated or unsaturated, carbon compound, excluding aromatic compounds. An "aliphatic group" is a generalized group formed by removing one or more hydrogen atoms (as necessary for the particular group) from the carbon atom of an aliphatic compound. Aliphatic compounds and therefore aliphatic groups can contain organic functional group(s) and/or atom(s) other than carbon and hydrogen.

An aromatic compound is a compound containing a cyclically conjugated double bond system that follows the Hückel (4n+2) rule and contains (4n+2) pi-electrons, where n is an integer from 1 to 5. Aromatic compounds include "arenes" (hydrocarbon aromatic compounds) and "heteroarenes," also termed "hetarenes" (heteroaromatic compounds formally derived from arenes by replacement of one or more methine (—C=) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Hückel rule (4n+2). While arene compounds and heteroarene compounds are mutually exclusive members of the group of aromatic compounds, a compound that has both an arene group and a heteroarene group are generally considered a heteroarene compound. Aromatic compounds, arenes, and heteroarenes can be monocyclic (e.g., benzene, toluene, furan, pyridine, methylpyridine) or polycyclic unless otherwise specified. Polycyclic aromatic compounds, arenes, and heteroarenes, include, unless otherwise specified, compounds wherein the aromatic rings can be fused (e.g., naphthalene, benzofuran, and indole), compounds where the aromatic groups can be separate and joined by a bond (e.g., biphenyl or 4-phenylpyridine), or compounds where the aromatic groups are joined by a group containing linking atoms (e.g., carbon of the methylene group in diphenylmethane; oxygen of diphenyl ether; nitrogen of triphenyl amine; among others linking groups). As disclosed herein, the term "substituted" can be used to describe an aromatic group, arene, or heteroarene wherein a non-hydrogen moiety formally replaces a hydrogen in the compound and is intended to be non-limiting.

An "aromatic group" refers to a generalized group formed by removing one or more hydrogen atoms (as necessary for the particular group and at least one of which is an aromatic ring carbon atom) from an aromatic compound. For a univalent "aromatic group," the removed hydrogen atom must be from an aromatic ring carbon. For an "aromatic group" formed by removing more than one hydrogen atom from an aromatic compound, at least one hydrogen atom must be from an aromatic hydrocarbon ring carbon. Additionally, an "aromatic group" can have hydrogen atoms removed from the same ring of an aromatic ring or ring system (e.g., phen-1,4-ylene, pyridin-2,3-ylene, naphth-1,2-ylene, and benzofuran-2,3-ylene), hydrogen atoms removed from two different rings of a ring system (e.g., naphth-1,8-ylene and benzofuran-2,7-ylene), or hydrogen atoms removed from two isolated aromatic rings or ring systems (e.g., bis(phen-4-ylene)methane).

An arene is aromatic hydrocarbon, with or without side chains (e.g., benzene, toluene, or xylene, among others). An "aryl group" is a group derived from the formal removal of a hydrogen atom from an aromatic ring carbon of an arene. It should be noted that the arene can contain a single aromatic hydrocarbon ring (e.g., benzene, or toluene), contain fused aromatic rings (e.g., naphthalene or anthracene), and contain one or more isolated aromatic rings covalently linked via a bond (e.g., biphenyl) or non-aromatic hydrocarbon group(s) (e.g., diphenylmethane). Similarly, an "arylene group" refers to a group formed by removing two hydrogen atoms (at least one of which is from an aromatic ring carbon) from an arene. An "arene group" refers to a generalized group formed by removing one or more hydrogen atoms (as necessary for the particular group and at least one of which is an aromatic ring carbon) from an arene. It should be noted that according the definitions provided herein, general arene groups (including an aryl group and an arylene group) include those having zero, one, or more than one hydrocarbyl substituent groups located on an aromatic hydrocarbon ring or ring system carbon atom (e.g., a toluene group or a xylene group, among others) and is a member of the group of hydrocarbon groups. However, a phenyl group (or phenylene group) and/or a naphthyl group (or naphthylene group) refer to the specific unsubstituted arene groups (including no hydrocarbyl group located on an aromatic hydrocarbon ring or ring system carbon atom). Consequently, a substituted phenyl group or substituted naphthyl group refers to the respective arene group having one or more substituent groups (including halogens, hydrocarbyl groups, or hydrocarboxy groups, among others) located on an aromatic hydrocarbon ring or ring system carbon atom. When the substituted phenyl group and/or substituted naphtyl group is a member of the group of hydrocarbon groups (or a member of the general group of arene groups), each substituent is limited to a hydrocarbyl substituent group. One having ordinary skill in the art can readily discern and select general phenyl and/or naphthyl groups, specific phenyl and/or naphthyl groups, and/or individual substituted phenyl or substituted naphthyl groups which can be utilized as a member of the group of hydrocarbon groups (or a member of the general group of arene groups).

An "aralkyl group" is an aryl-substituted alkyl group having a free valance at a non-aromatic carbon atom (e.g., a benzyl group, or a 2-phenyleth-1-yl group, among others). Similarly, an "aralkylene group" is an aryl-substituted alkylene group having two free valencies at a single non-aromatic carbon atom or a free valence at two non-aromatic carbon atoms while an "aralkane group" is a generalized aryl-substituted alkane group having one or more free valencies at a non-aromatic carbon atom(s). It should be noted that according the definitions provided herein, general aralkane groups include those having zero, one, or more than one hydrocarbyl substituent groups located on an aralkane aromatic hydrocarbon ring or ring system carbon atom and is a member of the group of hydrocarbon groups. However, specific aralkane groups specifying a particular aryl group (e.g., the phenyl group in a benzyl group or a 2-phenylethyl group, among others) refer to the specific unsubstituted aralkane groups (including no hydrocarbyl group located on the aralkane aromatic hydrocarbon ring or ring system carbon atom). Consequently, a substituted aralkane group specifying a particular aryl group refers to a respective aralkane group having one or more substituent groups (including halogens, hydrocarbyl groups, or hydrocarboxy groups, among others). When the substituted aralkane group specifying a particular aryl group is a member of the group of hydrocarbon groups (or a member of the general group of aralkane groups), each substituent is limited to a hydrocarbyl substituent group. One can readily discern and select substituted aralkane groups specifying a particular aryl group which can be utilized as a member of the group of hydrocarbon groups (or a member of the general group of aralkane groups).

As utilized herein the term "hydrocarbylmetal compound" refers to a compound having at least one metal-carbon bond where the carbon atom taking part in the metal-carbon bond is part of a hydrocarbyl group. The "hydrocarbyl compound" can contain other non-hydrocarbyl groups such as halides, hydocarboxides, alkoxides, carboxylates, and azanides, among other non-hydrocarbyl groups, as long as the compound contains at least one metal-carbon bond where the carbon atom taking part in the metal-carbon bond is part of a hydrocarbyl group. Similarly, any specific "hydrocarbylmetal compound" (compounds where the metal of the hydrocarbylmetal compound is specified) refers to the compound having at least one specific metal-carbon bond where the carbon atom taking part in the metal-carbon bond is part of a hydrocarbyl group.

A "halide" has its usual meaning; therefore, examples of halides include fluoride, chloride, bromide, and iodide.

The term "substituted" when used to describe a group, for example, when referring to a substituted analog of a particular group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

The terms "room temperature" or "ambient temperature" are used herein to describe any temperature from 15° C. to 35° C. wherein no external heat or cooling source is directly applied. Accordingly, the terms "room temperature" and "ambient temperature" encompass the individual temperatures and any and all ranges, subranges, and combinations of subranges of temperatures from 15° C. to 35° C. wherein no external heating or cooling source is directly applied. The term "atmospheric pressure" is used herein to describe an earth air pressure wherein no external pressure modifying means is utilized. Generally, unless practiced at extreme earth altitudes, "atmospheric pressure" is about 1 atmosphere (alternatively, about 14.7 psi or about 101 kPa). References to gaseous, liquid, and/or solid materials refer to the physical state of the material at 25° C. and atmospheric pressure.

Features within this disclosure that are provided as minimum values can be alternatively stated as "at least" or "greater than or equal to" any recited minimum value for the feature disclosed herein. Features within this disclosure that are provided as maximum values can be alternatively stated as "less than or equal to" for the feature disclosed herein.

Within this disclosure, the normal rules of organic nomenclature prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4-position and hydrogens located at the 2, 3, 5, and 6 positions. References to compounds or groups having substitutions at positions in addition to the indicated position can be referenced using comprising or some other alternative language. For example, a reference to a phenyl group comprising a substituent at the 4-position refers to a group having a non-hydrogen substituent at the 4-position and hydrogen or any non-hydrogen substituent at the 2, 3, 5, and 6 positions.

The term "reaction zone effluent," and its derivatives (e.g., oligomerization reaction zone effluent) generally refers to all the material which exits the reaction zone. The term "reaction zone effluent," and its derivatives, can also be prefaced with other descriptors that limit the portion of the reaction zone effluent being referenced. For example, the term "reaction zone effluent" refers to all material exiting the reaction zone (e.g., product and solvent or diluent, among others), while the term "olefin reaction zone effluent" refers to only the olefins within the reaction zone effluent and the term "oligomer product reaction zone effluent" refers to oligomer product within the reaction zone effluent.

The term oligomer refers to a product that contains from 2 to 20 monomer units. The terms "oligomer product" and "oligomer product effluent" include all oligomer products made by the "oligomerization" process, but exclude other non-oligomer components of the reaction zone effluent stream, such as unreacted monomer (ethylene), organic reaction medium, and hydrogen, amongst other components. The term "oligomerization," and its derivatives, refers to processes which produce an oligomer product comprising at least 20 wt. %, 35 wt. %, 50 wt. %, or 60 wt. % products comprising from 2 to 20 monomer units. In an example, an "oligomerization" process using ethylene as the monomer produces a mixture of products comprising at least 20 wt. %, 35 wt. %, 50 wt. %, or 60 wt. % oligomers having from 4 to 40 carbon atoms.

Schulz-Flory K value (sometimes referred to as Schulz-Flory chain growth factor, K value) can be defined the equation: $K=X_{q+1}/X_q$ wherein $X_{q+1}$ is the number of moles of oligomer product produced having q+1 monomer (e.g., ethylene) units and $X_q$ is the number of moles of oligomer product produced having q monomer (e.g., ethylene) units. Generally, the Schulz-Flory K value can be determined using any two oligomers of the oligomer product which differs in the number of monomer units by 1. However, one would appreciate that product isolation and analysis can lead to inaccuracies in a determined oligomer product distribution using particular oligomers (e.g., incomplete recovery of gaseous product and/or solid product during product isolation). One having ordinary skill in the art would recognize such issues and can choose the appropriate oligomers upon which to base the determination of the Schulz-Flory K value.

Catalyst system productivity is defined as grams of a product produced per gram (or mole) of zirconium in the catalyst system utilized in the oligomerization. Catalyst system activity is defined as grams of a product produced per gram (or mole) of zirconium per unit of time (e.g., hour) of an oligomerization. Catalyst system productivity and/or activity can be stated in terms of various products of an oligomerization and/or components of catalyst system. For example, in an ethylene oligomerization process utilizing a catalyst system comprising a zirconium compound, the catalyst system productivity which can be utilized include (g oligomer product)/(g Zr), among other productivities.

Unless otherwise specified, the terms "contact" and "combine," and their derivatives, can refer to any addition sequence, order, or concentration for contacting or combining two or more components of the disclosed embodiments. Combining or contacting of oligomerization components can occur in one or more reaction zones under suitable contact conditions such as temperature, pressure, contact time, flow rates, etc.

The terms "catalyst system", "catalyst composition", "catalyst mixture", and the like, do not depend upon the actual product or composition resulting from the contact or reaction of the initial components of the disclosed or claimed catalyst composition/mixture/system, the nature of the active catalytic site, or the fate of the organoaluminum compound and the heteroatomic ligand transition metal compound complex after combining these components. Therefore, the terms "catalyst system", "catalyst composition", "catalyst mixture", and the like, encompass the initial starting components of the composition, as well as whatever product(s) may result from contacting these initial starting components. The terms "catalyst system", "catalyst composition", "catalyst mixture", and the like, may be used interchangeably throughout this disclosure.

In this disclosure, a process can have multiple steps or can include features having a number of different elements (e.g., components in a catalyst system or components in an olefin oligomerization process, among other features). These steps and/or elements can be designated utilizing the terms first, second, and third, etc., the series a), b), c), etc., i), ii), iii), etc., (a), (b), (c), etc., and/or (i), (ii), (iii), etc. (among other designation series) as necessary to provide a designation for each process step and/or element. It should be understood that the numerical or alphabetical precedence of the designations within a designation series does not imply a particular order or preference of the process step in a process described herein, the feature(s) described herein, and/or an element(s) in a feature unless specifically specified otherwise or necessitated by other process steps, elements, and/or element features. Additionally, these designations series are provided to differentiate different process steps and/or elements in a feature and can be utilized as necessary, and without regard to the designation series utilized for a particular step, element, or feature utilized within this description as long as the designation series consistently distinguish different features, different process steps, and/or different elements of a feature.

The terms "simultaneously," "simultaneously contact," "contact simultaneously," and their derivatives when referring to a contact method refers to a contact method wherein the two or more recited compounds, mixtures, streams, and/or compositions are contacted by flowing into a common junction, pot, vessel, or reactor, among others, at the same time. The terms "substantially simultaneously," "substantially simultaneously contact," "contact substantially simultaneously," and their derivatives when referring to a contact method refers to a contact method wherein, during the contact of two or more recited compounds, mixtures, streams, and/or compositions, the two or more recited compounds, mixtures, streams, and/or compositions are contacted such that for some period during the contact process the two or more recited compounds, mixtures, streams, and/or compositions flow into a common junction, pot, vessel, or reactor at the same time. It should be noted that the terms "substantially simultaneously," "substantially simultaneously contact," "contact substantially simultaneously," and their derivatives do not mean that the two or more recited compounds, mixtures, streams, and/or compositions are contacted simultaneously over the entire addition of each of the two or more recited compounds, mixtures, streams, and/or compositions. The terms "substantially simultaneously," "substantially simultaneously contact," "contact substantially simultaneously," and it derivatives include scenarios where the flow of one of the (or less than all of the) recited compounds, mixtures, streams, and/or compositions can be initiated into the common junction, pot, vessel, or reactor before the others and/or the flow of one of the (or less than all of the) recited compounds, mixtures, streams, and/or compositions into the common junction, pot, vessel, or reactor can be completed, stopped, or discontinued before the other recited compounds, mixtures, streams, and/or compositions. In any aspect and/or embodiment described herein, the terms "simultaneously," "simultaneously contact," "contact simultaneously," and their derivatives, can be modified by the inclusion of a term providing a quantity of the each of the recited compounds, mixtures, streams, and/or compositions which can be contacted simultaneously indicate scenarios of various degrees of "substantially simultaneously," "substantially simultaneously contact," "contact substantially simultaneously," and their derivatives. For example, at least 20%, 30%, 40%, 50%, 60%, 70%, 75%, 80%, 85%, 90%, 95% of each of the recited compounds, mixtures, streams, and/or compositions can be "simultaneously contacted" or "contacted simultaneously." Generally, the percentages of the recited compounds, mixtures, streams, and/or compositions that can be "simultaneously contacted" or "contacted simultaneously" can be by weight (wt. %), by volume (volume %), or by mole (mole %). Unless otherwise specified, recited compounds, mixtures, streams, and/or compositions that are "substantially simultaneously," "substantially simultaneously contact," "contact substantially simultaneously," and their derivatives shall mean that at least 50% of each of the recited compounds, mixtures, streams, and/or compositions can be "simultaneously contacted" or "contacted simultaneously."

It should be further noted, that in reference to contact method or process, "simultaneously," "simultaneously contact," "contact simultaneously," "substantially simultaneously contact," "contact substantially simultaneously," and their derivatives is different than a process or method wherein one or more a first materials (e.g., compound, mixture, stream, and/or composition) already resides in a pot, vessel, or reactor and one or more other compounds, mixtures, streams, and/or compositions are added to the pot, vessel, or reactor. In this instance the first material in the pot, vessel, or reactor does not flow into the pot, vessel, or reactor concurrently with the other compounds, mixtures, streams, and/or compositions and the material in the pot. Thus, the first material and the other compounds, mixtures, streams, and/or compositions cannot be said to be "simultaneously contacted," "contacted simultaneously," "substantially simultaneously contacted," or "contacted substantially simultaneously." with the other component(s).

The term "contacting" is used herein to describe systems, compositions, processes, and methods in which the components are contacted or combined together in any order, in any manner, and for any length of time, unless otherwise specified. For example, the components can be combined by blending or mixing, using any suitable technique. Herein, "contacting" two or more components can result in a reaction product mixture or a reaction mixture.

Within this specification, the word "reactor" refers to a single piece of equipment, such as, for example, a vessel, in which a reaction takes place, but excludes any associated equipment such as piping, pumps, and the like which is external to the vessel. Examples of reactors include stirred tank reactors (e.g., a continuous stirred tank reactor), plug flow reactors, or any other type of reactor. Within this specification "reactor system" refers to any portion of equipment in which a desired reaction occurs, including but not limited to, a reactor, associated piping, associated pumps, and any other associated equipment. It should be noted that in some cases a "reactor" can also be a "reactor system." For example, in some instances a polyethylene loop reactor can be considered a reactor system. The terms "reactor" and "reactor system" can be qualified to refer to more specific "reactors" and "reactor systems" by use of additional qualifying terms. For example, the use of the term "oligomerization reactor" and "oligomerization reactor system" indicates that the desired reaction within the reactor and/or reactor system is an oligomerization.

Within this specification, term "reaction zone" refers to the portion of a reaction system where all the necessary reaction components and reaction conditions are present such that the reaction can occur at a desired rate. That is to say that the reaction zone begins where the necessary reaction components and reaction conditions are present to maintain the reaction within 25 percent of the average reaction rate and the reaction system ends where the conditions do not maintain a reaction rate within 25 percent of the average reaction rate (based upon a volume average of the reaction rate of the reaction zone). For example, in terms of an ethylene oligomerization process, the reaction zone begins at the point where sufficient ethylene and active catalyst system is present under the sufficient reaction conditions (e.g., temperature and/or pressure, among others) to maintain oligomer product production at the desired rate and the reaction zone ends at a point where either the catalyst system is deactivated, sufficient ethylene is not present to sustain oligomer product production, or other reaction conditions (e.g., temperature and/or pressure, among others) are not sufficient to maintain the oligomer product production or the desired oligomer product production rate. Within this specification the "reaction zone" can comprise one or more reactors. The term "reaction zone" can be qualified to refer to more specific "reaction zones" by use of additional qualifying terms. For example, the use of the term "oligomerization reaction zone" indicates that the desired reaction within the "reaction zone" is an oligomerization.

The term "reaction system" refers to all of the equipment to produce a product. The term "reaction system" includes reactors, reaction zones, and all the associated equipment, associated process lines, and control equipment which can bring the necessary component(s) into and out of the reaction system and control the reaction. Within this specification the "reaction system" can comprise one or more reactor zones, one or more reactors, and associated equipment to produce a product. The term "reaction system" can be qualified to refer to more specific "reaction systems" by use of additional qualifying terms. For example, the use of the term "oligomerization reaction system" indicates that the "reaction system" relates to an oligomerization.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

Disclosed herein are processes comprising a) contacting i) ethylene, ii) a catalyst system comprising 1) a zirconium compound, and 2) an hydrocarbylmetal compound, iii) a chain transfer agent comprising a silyl hydride compound, a compound having a hydrogen sulfur bond, a compound having a hydrogen phosphorus bond, or any combination thereof, and iv) optionally, an organic reaction medium and b) forming an oligomer product in a reaction zone. Also disclosed herein, are processes comprising a) contacting i) ethylene, ii) a catalyst system comprising 1) a zirconium compound, and 2) an hydrocarbylmetal compound, iii) hydrogen, and iv) optionally, an organic reaction medium and b) forming an oligomer product in a reaction zone. Further disclosed herein, are processes comprising a) contacting i) ethylene, ii) a catalyst system comprising 1) a zirconium compound, and 2) an hydrocarbylmetal compound, iii) a transition metal compound chain transfer agent, and iv) optionally, an organic reaction medium and b) forming an oligomer product in a reaction zone. Also disclosed herein are processes comprising a) introducing i) ethylene, ii) a catalyst system or catalyst system components comprising 1) a zirconium compound, and 2) an hydrocarbylmetal compound, iii) a chain transfer agent comprising a silyl hydride compound, a compound having a hydrogen sulfur bond, a compound having a hydrogen phosphorus bond, or any combination thereof, and iv) optionally, an organic reaction medium into a reaction zone and b) forming an oligomer product in the reaction zone. Also disclosed herein, are processes comprising a) introducing i) ethylene, ii) a catalyst system or catalyst system components comprising 1) a zirconium compound, and 2) an hydrocarbylmetal compound, iii) hydrogen, and iv) optionally, an organic reaction medium into a reaction zone and b) forming an oligomer product in the reaction zone. Further disclosed herein, are processes comprising a) introducing i) ethylene, ii) a catalyst system or catalyst system components comprising 1) a zirconium compound, and 2) an hydrocarbylmetal compound, iii) a transition metal compound chain transfer agent, and iv) optionally, an organic reaction medium into a reaction zone and b) forming an oligomer product in the reaction zone.

In an aspect, the oligomer product can be formed at, the reaction zone can have, or the reaction zone can operate at, conditions capable of forming an oligomer product. Generally, the catalyst system, the elements of the catalyst system (e.g., the zirconium compound, the hydrocarbylmetal compound, and any other catalyst system elements described herein), the chain transfer agent, the hydrogen, the transition metal compound chain transfer agent, the optional organic reaction medium, the oligomer product, the conditions at which the oligomer product is formed, the condition the reaction zone can have, the conditions at which the reaction can operate, and/or any other catalyst system and/or process elements described herein are independent elements of the processes described herein and are independently described herein. These independently described elements can be utilized in any combination, and without limitation, to further describe the processes provided herein.

In an aspect, the zirconium compound of the catalyst system can have the formula $ZrX^1_m Y^1_q$, $ZrX^1_m$, $ZrY^1_q$, or any combination thereof; alternatively, $ZrX^1_m Y^1_q$; alternatively, $ZrX^1_m$; or alternatively, $ZrY^1_q$. $X^1$, $Y^1$, m, and q of the zirconium compounds having the formula $ZrX^1_m Y^1_q$, $ZrX^1_m$, or $ZrY^1_q$, are independent elements of the zirconium compound and are independently described herein. The independent descriptions of $X^1$, $Y^1$, m, and q can be utilized without limitation, and in any combination, to further describe the zirconium compound. In an embodiment, each $X^1$ independently can be a halide. In an embodiment, each $Y^1$ independently can be a hydrocarboxide, a dihydrocarbylazanide, a hydrocarbylcarboxylate, a hydrocarbylsulfonate, or a β-diketonate; alternatively, a hydrocarboxide, a hydrocarbylcarboxylate, a hydrocarbylsulfonate, or a β-diketonate; alternatively, a hydrocarboxide, a hydrocarbylcarboxylate, a or hydrocarbylsulfonate; alternatively, a hydrocarbylcarboxylate or a hydrocarbylsulfonate; alternatively, a hydrocarboxide; alternatively, a dihydrocarbylazanide; alternatively, a hydrocarbylcarboxylate; alternatively, a hydrocarbylsulfonate; or alternatively, a β-diketonate. In an embodiment, in can be in a range from 0 to 4; alternatively, in a range from 2 to 4; alternatively, 2; alternatively, 3; or alternatively, 4. In an embodiment, q can be in a range from 0 to 4; alternatively, in a range from 2 to 4; alternatively, 2; alternatively, 3; or alternatively, 4. Where in +q is an integer in from 2 to 4; alternatively, 2; alternatively, 3; or alternatively 4.

Each halide which can be utilized as $X^1$ of the zirconium compound independently can be fluoride, chloride, bromide, or iodide; alternatively, chloride, bromide, or iodide; alternatively, chloride; alternatively, bromide; or alternatively iodide.

The hydrocarboxide which can be utilized as Y of the zirconium compound can be a $C_1$ to $C_{20}$, a $C_1$ to $C_{10}$, or a $C_1$ to $C_5$ hydrocarboxide. The hydrocarboxide, $Y^1$, can have the formula $^-OR^2$. $R^2$ of the hydrocarboxide having the formula $^-OR^2$ can be a $C_1$ to $C_{20}$, a $C_1$ to $C_{10}$, or a $C_1$ to $C_5$ hydrocarbyl group. The $R^2$ hydrocarbyl group of the hydrocarboxide having the formula $^-OR^2$ can be an alkyl group, a cycloalkyl group, an aryl group, or an aralkyl group; alternatively, an alkyl group or an aryl group; alternatively, an alkyl group; alternatively, a cycloalkyl group; alternatively, an aryl group; or alternatively an aralkyl group. The $R^2$ alkyl group can be a $C_1$ to $C_{20}$, a $C_1$ to $C_{10}$, or a $C_1$ to $C_5$ alkyl group. The $R^2$ cycloalkyl group can be a $C_4$ to $C_{20}$, $C_5$ to $C_{15}$, or a $C_5$ to $C_{10}$ cycloalkyl group. The $R^2$ aryl group can be a $C_6$ to $C_{20}$, $C_6$ to $C_{15}$ or a $C_6$ to $C_{10}$ aryl group. The $R^2$ aralkyl group can be a $C_7$ to $C_{20}$, $C_7$ to $C_{15}$ or a $C_7$ to $C_{10}$ aralkyl group. In an aspect, the $R^2$ group of the hydrocarboxide having the formula $^-OR^2$ can be a methyl group, an ethyl group, a propyl group, a butyl group, a pentyl group, a cyclopentyl group, cyclohexyl group, a phenyl group, a toluyl group, a xylyl group, a benzyl group, or a ethylphenyl group; alternatively, a methyl group, an ethyl group, a propyl group, a butyl group, or a pentyl group; alternatively, a cyclopentyl group or a cyclohexyl group; alternatively, a phenyl group, a toluyl group, or a xylyl group; or alternatively, a benzyl group or an ethylphenyl group. In an aspect, each hydrocarboxide, $Y^1$ of the zirconium compound can be methoxide, ethoxide, a propoxide, a butoxide, a pentoxide, a cyclopentoxide, a cyclohexoxide, a phenoxide, a toluoxide, a xyloxide, a benzoxide, or a ethylphenoxide; alternatively, methoxide, ethoxide, a propoxide, a butoxide, or a pentoxide; alternatively, a cyclopentoxide or a cyclohexoxide; alternatively, a phenoxide, a toluoxide, or a xyloxide; or alternatively, a benzoxide or an ethylphenoxide.

The hydrocarbylcarboxylate which can be utilized as $Y^1$ of the zirconium compound can be a $C_1$ to $C_{20}$, a $C_1$ to $C_{15}$, a $C_1$ to $C_{10}$, or a $C_1$ to $C_5$ hydrocarbylcarboxylate. The hydrocarbylcarboxylate which can be utilized as $Y^1$ of the zirconium compound can have the formula $^-OC(=O)R^3$. The hydrocarbylsulfonate which can be utilized as $Y^1$ of the zirconium compound can be a $C_1$ to $C_{20}$, a $C_1$ to $C_{10}$, or a $C_1$ to $C_5$ hydrocarbylsulfonate. The hydrocarbylsulfonate which can be utilized as $Y^1$ of the zirconium compound can have the formula $^-OS(=O)_2R^3$. $R^3$ of the hydrocarboxylate having the formula $^-OC(=O)R^3$ and/or the hydrocarbylsulfonate having the formula $^-OS(=O)_2R^3$ can be a $C_1$ to $C_{20}$, a $C_1$ to $C_{15}$, a $C_1$ to $C_{10}$, or a $C_1$ to $C_5$ hydrocarbyl group. The $R^3$ hydrocarbyl group of the hydrocarboxylate having the formula $^-OC(=O)R^3$ and/or the hydrocarbylsulfonate having the formula $^-OS(=O)_2R^3$ can be an alkyl group, a cycloalkyl group, an aryl group, or an aralkyl group; alternatively, an alkyl group or an aryl group; alternatively, an alkyl group; alternatively, a cycloalkyl group; alternatively, an aryl group; or alternatively an aralkyl group. The $R^3$ alkyl group can be a $C_1$ to $C_{20}$, a $C_1$ to $C_{10}$, or a $C_1$ to $C_5$ alkyl group. The $R^3$ cycloalkyl group can be a $C_4$ to $C_{20}$, $C_5$ to $C_{15}$, or a $C_5$ to $C_{10}$ cycloalkyl group. The $R^3$ aryl group can be a $C_6$ to $C_{20}$, $C_6$ to $C_{15}$ or a $C_6$ to $C_1$ aryl group. The $R^3$ aralkyl group can be a $C_7$ to $C_{20}$, $C_7$ to $C_{15}$ or a $C_7$ to $C_{10}$ aralkyl group. The R group of the hydrocarboxylate having the formula $^-OC(=O)R^3$ and/or the hydrocarbylsulfonate having the formula $^-OS(=O)_2R^3$ can be a methyl group, an ethyl group, a propyl group, a butyl group, a pentyl group, a hexyl group, a heptyl group, a cyclopentyl group, a cyclohexyl group, a phenyl group, a toluyl group, a xylyl group, a benzyl group, or a ethylphenyl group; alternatively, a methyl group, an ethyl group, a propyl group, a butyl group, a pentyl group, a hexyl group, or an heptyl group; alternatively, a cyclopentyl group or a cyclohexyl group; alternatively, a phenyl group, a toluyl group, or a xylyl group; or alternatively, a benzyl group or an ethylphenyl group. Each hydrocarboxylate which can be utilized as $Y^1$ of the zirconium compound can be acetate, propanoate, a butanoate, a pentonate, a hexanoate, a heptanoate, octanoate, a cyclopentylacetate, a cyclohexylacetate, a benzoate, a methylbenzoate, a dimethylbenzoate, phenylacetate, or phenylpropanoate; alternatively, acetate, propanoate, a butanoate, a pentonate, a hexanoate, a heptanoate, or octanoate; alternatively, a cyclopentylacetate or cyclohexylacetate; alternatively, benzoate, a methylbenzoate, or dimethylbenzoate; or alternatively, phenylacetate or a phenylpropanoate. Each hydrocarbylsulfonate which can be utilized as $Y^1$ of the zirconium compound can be methyl sulfonate, ethyl sulfonate, a propyl sulfonate, a butyl sulfonate, a pentyl sulfonate, a hexyl sulfonate, a heptyl sulfonate, cyclopentyl sulfonate, cyclohexyl sulfonate, a phenyl sulfonate, a toluyl sulfonate, a xylyl sulfonate, a benzyl sulfonate, or a ethylphenyl sulfonate; alternatively, a methyl sulfonate, ethyl sulfonate, a propyl sulfonate, a butyl sulfonate, a pentyl sulfonate, a hexyl sulfonate, or an heptyl sulfonate; alternatively, a cyclopentyl sulfonate or a cyclohexyl sulfonate; alternatively, a phenyl sulfonate, a toluyl sulfonate, or a xylyl sulfonate.

The dihydrocarbylazanide which can be utilized a $Y^1$ of the zirconium compound can be a $C_2$ to $C_{30}$, a $C_2$ to $C_{20}$, or a $C_2$ to $C_5$ dihydrocarbylazanide. The dihydrocarbylazanide which can be utilized a $Y^1$ of the zirconium compound can have the formula $^-N(R^4)_2$. In some embodiments, each $R^4$ hydrocarbyl group of the dihydrocarbylazanide having the formula $^-N(R^4)_2$ independently can be an alkyl group, a cycloalkyl group, an aryl group, or an aralkyl group; alternatively, an alkyl group or an aryl group; alternatively, an alkyl group; alternatively, a cycloalkyl group; alternatively, an aryl group; or alternatively an aralkyl group. Each $R^4$ alkyl group independently can be a $C_1$ to $C_{15}$, a $C_1$ to $C_{10}$, or a $C_1$ to $C_5$ alkyl group. Each $R^4$ cycloalkyl group independently can be a $C_4$ to $C_{15}$, or a $C_5$ to $C_{15}$ cycloalkyl group. Each $R^4$ aryl group independently can be a $C_6$ to $C_{20}$, $C_6$ to $C_{15}$ or a $C_6$ to $C_{10}$ aryl group. Each $R^4$ aralkyl group independently can be a $C_7$ to $C_{20}$, $C_7$ to $C_{15}$ or a $C_7$ to $C_{10}$ aralkyl group. Each $R^4$ hydrocarbyl group of the dihydrocarbylazanide having the formula $^-N(R^4)_2$ independently can be a methyl group, an ethyl group, a propyl group, a butyl group, a pentyl group, a cyclopentyl group, a cyclohexyl group, a phenyl group, a toluyl group, a xylyl group, a benzyl group, or a ethylphenyl group; alternatively, a methyl group, an ethyl group, a propyl group, a butyl group, or a pentyl group; alternatively, a cyclopentyl group or a cyclohexyl group; alternatively, a phenyl group, a toluyl group, or a xylyl group; or alternatively, a benzyl group or an ethylphenyl group. In an aspect, the two $R^4$ groups of the dihydrocarbylazanide can be joined to form a hydrocarbylene group, $L^1$. In such an aspect, the joined $R^4$ groups, i.e., $L^1$, form a ring or ring system including the azanide nitrogen atom. In some aspects, the $L^1$ hydrocarbylene group can be a $C_2$ to $C_{30}$, a $C_2$ to $C_{20}$, or a $C_2$ to $C_{10}$ hydrocarbylene group; or alternatively, $L^1$ can be a $C_2$ to $C_{30}$, a $C_2$ to $C_{20}$, or a $C_2$ to $C_{10}$ alkylene group. In an aspect, $L^1$ can be a propylene group, a butylene group, a hexylene group, or a heptalene group. In an aspect, each dihydrocarbylazanide which can be utilized a $Y^1$ of the zirconium compound can be dimethylazanide, diethylazanide, a dipropylazinide, pyrrolidine azanide, piperidine azanide, diphenylazanide, a ditoluylazanide, a dixylyazanide, or dibenzylazanide; alternatively, dimethylazanide, diethylazanide, or a dipropylazinide; alternatively, pyrrolidine azanide or piperidine azanide; alternatively, diphenylazanide, a ditoluylazanide, a dixylyazanide; or alternatively dibenzylazanide.

The β-diketonate which can be utilized a $Y^1$ of the zirconium compound can be a be a $C_5$ to $C_{20}$, a $C_5$ to $C_{15}$, or a $C_5$ to $C_{10}$ β-diketonate. In an embodiment aspect, each β-diketonate independently can be acetylacetonate (i.e., 2,4-pentanedionate) or benzoylacetonate; alternatively, acetylacetonate; or alternatively, benzoylacetonate.

In an embodiment, the zirconium compound of the catalyst system can be an at least partially hydrolyzed zirconium compound by contacting the zirconium compound with water (referred to herein as a partially hydrolyzed zirconium compound). In some embodiments, the partially hydrolyzed zirconium compound comprises, consists essentially of or consists of, a zirconium compound (any described herein) contacted with water. In some embodiments, the zirconium compound of the partially hydrolyzed zirconium compound can have the formula $ZrX^1_m Y^1_q$ where each $X^1$ independently can be a halide (any disclosed herein), $Y^1$ can have the formula $^-OR^2$ where $R^2$ can be any $R^2$ hydrocarbyl group (general or specific) described herein or $^-OC(=O)R^3$ where $R^3$ can be any R hydrocarbyl group (general or specific) described herein, m can be in a range from 0 to 4, q can be in a range from 0 to 4, and m+q can be 4. In some embodiments, m can be in a range from 0 to 3. In an embodiment, the wherein the molar ratio of water to the zirconium of the zirconium compound can be in the range of 0.01:1 to 3:1, 0.1: to 2:1, 0.25:1 to 1.75:1.

In a non-limiting aspect, the zirconium compound of the catalyst system can have the formula $ZrX^1_m Y^1_q$ where each $X^1$ independently can be a halide (any disclosed herein), $Y^1$ can have the formula $^-OC(=O)R^3$ or $^-OS(=O)_2R^3$ where $R^3$ can be any $R^3$ hydrocarbyl group (general or specific) described herein, m can be in a range from 0 to 4, q can be in a range from 0 to 4, and m+q can be 4. In another non-limiting aspect, the zirconium compound of the catalyst system can have the formula $ZrX^1_m$ where each $X^1$ independently can be a halide (any disclosed herein) and m can be and integer from 2 to 4, alternatively 2; or alternatively, 4. In yet another non-limiting aspect, the zirconium compound can have the formula $ZrY^1_q$ where each $Y^1$ independently is $^-OR^2$ wherein $R^2$ is a $C_1$ to $C_{10}$ alkyl group or $^-OC(=O)R^3$ where $R^3$ is a $C_1$ to $C_{10}$ alkyl group and q is an integer from 2 to 4, alternatively, 2; alternatively, 4. In another non-limiting aspect, the zirconium compound of the catalyst system can have the formula $ZrX^1_m Y^1_q$ where each X independently can be a halide (any described herein), $Y^1$ can have the formula $^-OR^2$ where $R^2$ can be any $R^2$ hydrocarbyl group described herein, or can have the formula $^-OC(=O)R^3$ where $R^3$ can be any $R^3$ hydrocarbyl group (general or specific) described herein, in can be in a range from 0 to 4, q can be in a range from 0 to 4, and m+q can be 4. In a further non-limiting embodiment, the zirconium compound of the catalyst system can be a partially hydrolyzed zirconium compound where the zirconium compound can have the formula $ZrX^1_m Y^1_q$ where each $X^1$ independently can be a halide (any described herein), $Y^1$ can have the formula $^-OR^2$ where $R^2$ can be any $R^2$ hydrocarbyl group described herein, or can have the formula $^-OC(=O)R^3$ where R can be any $R^3$ hydrocarbyl group (general or specific) described herein, m can be in a range from 0 to 4, q can be in a range from 0 to 4, m+q can be 4, and the molar ratio of water to the zirconium of the zirconium compound can be in the range of 0.1: to 2:1.

Non-limiting exemplary zirconium compound which can be utilized in the catalyst systems for the processes described herein can comprise, can consist essentially of, or can be, $ZrCl_4$, $ZrBr_4$, $ZrI_4$, $ZrBr_2Cl_2$, $ZrBrCl_3$, $Zr(OC_2H_5)_4$, $Zr(OC_2H_5)_3Cl$, $Zr(OC_2H_5)_2Cl_2$, $Zr(OC_3H_7)_4$, $Zr(OC_3H_7)_3Cl$, $Zr(OC_3H_7)_2Cl_2$, $Zr(OC_4H_9)_4$, $Zr(OC_4H_9)_3Cl$, $Zr(OC_4H_9)_2Cl_2$, $Zr(OC_6H_5)_4$, $Zr(OC_6H_5)_3Cl$, $Zr(OC_6H_5)_2Cl_2$, $Zr(OCOCH_3)_4$, $Zr(OCOCH_3)_3Cl$, $Zr(OCOCH_3)_2Cl_2$, $Zr(OCOC_2H_5)_4$, $Zr(OCOC_2H_5)_3Cl$, $Zr(OCOC_2H_5)_2Cl_2$, $Zr(OCOC_3H_7)_4$, $Zr(OCOC_3H_7)_3Cl$, $Zr(OCOC_3H_7)_2Cl_2$, $Zr(OCOC_4H_9)_4$, $Zr(OCOC_4H_9)_3Cl$, $Zr(OCOC_4H_9)_2Cl_2$, $Zr(OCOC_6H_5)_4$, $Zr(OCOC_6H_5)_3Cl$, $Zr(OCOC_6H_5)_2Cl_2$, $Zr(OSO_3CH_3)_4$, $Zr(OSO_3C_2H_5)_4$, $Zr(OSO_3C_3H_7)_4$, $Zr(OSO_3C_4H_9)_4$, $Zr(OSO_3C_6H_5)_4$, $Zr(H_3CCOCHCOCH_3)_4$, $ZrCl_2(H_3CCOCHCOCH_3)_2$, $Zr((H_5C_6)COCHCO(C_5F_5))_4$, $ZrCl_2((H_5C_6)COCHCO(C_5F_5))_2$, $Zr((CH_3)_2N)_4$, $Zr((C_2H_5)_2N)_4$, $Zr((C_3H_7)_2N)_4$, or $Zr(C_4H_9)_2N)_4$. In some aspects, the zirconium compound can comprise, can consist essentially of, or can be, $ZrCl_4$, $ZrBr_4$, $ZrI_4$, $ZrBr_2Cl_2$, or $ZrBrCl_3$; alternatively, $Zr(OC_2H_5)_4$, $Zr(OC_2H_5)_3Cl$, $Zr(OC_2H_5)_2Cl_2$, $Zr(OC_3H_7)_4$, $Zr(OC_3H_7)_3Cl$, $Zr(OC_3H_7)_2Cl_2$, $Zr(OC_4H_9)_4$, $Zr(OC_4H_9)_3Cl$, $Zr(OC_4H_9)_2Cl_2$, $Zr(OC_6H_5)_4$, $Zr(OC_6H_5)_3Cl$, or $Zr(OC_6H_5)_2Cl_2$; alternatively, $Zr(OC_2H_5)_4$, $Zr(OC_3H_7)_4$, $Zr(OC_4H_9)_4$, or $Zr(OC_6H_5)_4$; alternatively, $Zr(OCH_5)_3Cl$, $Zr(OC_2H_5)_2Cl_2$, $Zr(OC_3H_7)_3Cl$, $Zr(OC_3H_7)_2Cl_2$, $Zr(OC_4H_9)_3Cl$, $Zr(OC_4H_9)_2Cl_2$, $Zr(OC_6H_5)_3Cl$, or $Zr(OC_6H_5)_2Cl_2$; alternatively, $Zr(OCOCH_3)_4$, $Zr(OCOCH_3)_3Cl$, $Zr(OCOCH_3)_2Cl_2$, $Zr(OCOC_2H_5)_4$, $Zr(OCOC_2H_5)_3Cl$, $Zr(OCOC_2H_5)_2Cl_2$, $Zr(OCOC_3H_7)_4$, $Zr(OCOC_3H)Cl$, $Zr(OCOC_3H_7)_2Cl_2$, $Zr(OCOC_4H_9)_4$, $Zr(OCOC_4H_9)_3Cl$, $Zr(OCOC_4H_9)_2Cl_2$, $Zr(OCOC_6H_5)_4$, $Zr(OCOC_6H_5)_3Cl$, or $Zr(OCOC_6H_5)_2Cl_2$; alternatively, $Zr(OCOCH_3)_4$, $Zr(OCOC_2H_5)_4$, $Zr(OCOC_3H_7)_4$, $Zr(OCOC_4H_9)_4$, or $Zr(OCOC_6H_5)_4$; alternatively, $Zr(OCOCH_3)_3Cl$, $Zr(OCOCH_3)_2Cl_2$, $Zr(OCOC_2H_5)_3Cl$, $Zr(OCOC_2H_5)_2Cl_2$, $Zr(OCOC_3H_7)_3Cl$, $Zr(OCOC_3H_7)_2Cl_2$, $Zr(OCOC_4H_9)_3Cl$, $Zr(OCOC_4H_9)_2Cl_2$, $Zr(OCOC_6H_5)_3Cl$, or $Zr(OCOC_6H_5)_2Cl_2$; alternatively, $Zr(OSO_3CH_3)_4$, $Zr(OSO_3C_2H_5)_4$, $Zr(OSO_3C_3H_7)_4$, $Zr(OSO_3C_4H_9)_4$, or $Zr(OSO_3C_6H)_4$; alternatively, $Zr(H_3CCOCHCOCH_3)_4$, $ZrCl_2(H_3CCOCHCOCH_3)_2$, $Zr((H_5C_6)COCHCO(C_5H_5))_4$, or $ZrCl_2((H_5C_6)COCHCO(C_5H_5))_2$; alternatively, $Zr(H_3CCOCHCOCH_3)_4$, or $Zr((H_5C_6)COCHCO(C_5H_5))_4$; alternatively, $ZrCl_2(H_3CCOCHCOCH_3)_2$ or $ZrCl_2((H_5C_6)COCHCO(C_5H_5))_2$; or alternatively, $Zr((CH_3)_2N)_4$, $Zr((C_2H_5)_2N)_4$, or $Zr((C_3H_7)_2N)_4$, $Zr(C_4H_9)_2N)_4$. In other aspects, the zirconium compound can comprise, can consist essentially of, or can be, $ZrCl_4$; alternatively, $Zr(OC_2H_5)_4$; alternatively, $Zr(OC_3H_7)_4$; alternatively, $Zr(OC_4H_9)_4$; alternatively, $Zr(OC_6H_5)_4$; alternatively, $Zr(OCOCH_3)_4$; alternatively, $Zr(OCOC_2H_5)_4$; alternatively, $Zr(OCOC_3H_7)_4$; alternatively, $Zr(OCOC_4H_9)_4$; alternatively, $Zr(OCOC_6H_5)_4$; alternatively, $Zr(OSO_3CH_3)_4$; alternatively, $Zr(OSO_3C_2H_5)_4$; alternatively, $Zr(OSO_3C_3H_7)_4$; alternatively, $Zr(OSO_3C_4H_9)_4$; or alternatively, or $Zr(OSO_3C_6H_5)_4$.

Generally, the hydrocarbylmetal compound can be any hydrocarbylmetal compound which in conjunction with the zirconium compound can form an oligomer product when contacted with ethylene. The hydrocarbylmetal compound of the catalyst system can comprise, can consist essentially of, or can be, any heteroleptic or homoleptic hydrocarbylmetal compound. In an aspect, the hydrocarbylmetal can have the formula $(R^1)_aM(X^2)_b$ where $R^1$ is a hydrocarbyl group, $X^2$ is a halide or hydrocarboxide, M is a metal, a ranges from 1 to 4, b ranges from 0 to 3, and a+b equal the oxidation state of the metal, M. In an aspect, the metal of the hydrocarbylmetal compound can comprise, can consist essentially of, or can consist of, a group 1, 2, 11, 12, 13, or 14 metal; alternatively, a group 1 or 2 metal; alternatively, a group 12, 13, or 14 metal; or alternatively, a group 12 or 13 metal; alternatively, a group 1 metal; alternatively, a group 2 metal; alternatively, a group 12 metal; or alternatively, a group 13. In some aspects, the metal of the hydrocarbylmetal compound can comprise, can consist essentially of, or can be, lithium, sodium, potassium, magnesium, copper, zinc, aluminum, or tin; alternatively, lithium, sodium, potassium, or magnesium; alternatively, zinc, aluminum, or tin; alternatively, lithium; alternatively, sodium; alternatively, potassium; alternatively, magnesium; alternatively, zinc; alternatively, aluminum; or alternatively, tin.

The hydrocarbyl group of the hydrocarbylmetal compound can be a $C_1$ to $C_{20}$, a $C_1$ to $C_{10}$, or a $C_1$ to $C_6$ hydrocarbyl group. In an aspect, the hydrocarbyl group of the hydrocarbylmetal compound can be an alkyl group, a cycloalkyl group, an aryl group, or an aralkyl group; alternatively, be an alkyl group; alternatively, a cycloalkyl group; alternatively, an aryl group; or alternatively, an aralkyl group. The alkyl group of the hydrocarbylmetal compound can be a $C_1$ to $C_{20}$, a $C_1$ to $C_{10}$, or a $C_1$ to $C_6$ alkyl group. The cycloalkyl group of the hydrocarbylmetal compound can be a $C_4$ to $C_{20}$, a $C_4$ to $C_{15}$, or a $C_4$ to $C_{10}$ cycloalkyl group. The aryl group of the hydrocarbylmetal compound can be a $C_6$ to $C_{20}$, a $C_6$ to $C_{15}$, or a $C_6$ to $C_{10}$ aryl group. The aralkyl group of the hydrocarbylmetal compound can be a $C_7$ to $C_{20}$, a $C_7$ to $C_{15}$, or a $C_7$ to $C_{10}$ aralkyl group.

In any aspect disclosed herein, the hydrocarbylmetal compound of the catalyst system can be an alkylmetal compound (i.e., a hydrocarbylmetal compound where $R^1$ is an alkyl group. In an embodiment, the alkylmetal compound of the catalyst system can comprise, can consist essentially of, or can be, an alkyllithium ($R^1Li$), an alkylsodium ($R^1Na$), an alkylpotassium ($R^1K$), an alkylmagnesium compound ($R^1_2Mg$ or $R^1MgX^2$), an alkylcopper compound ($R^1_2Cu$ or $R^1CuX^2$), an alkylzinc compound ($R^1_2Zn$ or $R^1ZnX^2$), an alkyltin compound ($R^1_4Sn$, $R^1_2Sn$, $R^1_3SnX^2$, $R^1_2SnX^2_2$, $R^1_2SnX^2_3$, $R^1_2Sn$, or $R^1SnX^2$), or an alkylaluminum compound ($AlX^2_2R^1$, $AlX^2R^1_2$, $AlR^1_3$, $Al_2X^2_5R^1$, $Al_2X^2_3(R^1)_3$, or $Al_2X^2R^1_5$); alternatively, an alkyllithium ($R^1Li$), an alkylsodium ($R^1Na$), an alkylpotassium ($R^1K$), an alkylmagnesium compound ($R^1_2Mg$ or $R^1MgX^2$), an alkylzinc compound ($R^1_2Zn$ or $R^1ZnX^2$), or an alkylaluminum compound ($AlX^2_2R^1$, $AlX^2R^1_2$, $AlR^1_3$, $Al^2X^2_5R^1$, $Al_2X^2_3R^1_3$, or $Al^2X^2R^1_5$); alternatively, an alkyllithium ($R^1Li$), an alkylsodium ($R^1Na$), or an alkylpotassium ($R^1K$); alternatively, an alkyllithium ($R^1Li$); alternatively, an alkylsodium ($R^1Na$); alternatively, an alkylmagnesium compound ($R^1_2Mg$ or $R^1MgX^2$); alternatively, an alkylzinc compound ($R^1_2Zn$ or $R^1ZnX^2$); alternatively, an alkyltin compound ($R^1_4Sn$, $R^1_2Sn$, $R^1_3SnX^2$, $R^1_2SnX^2_2$, $R^1_2SnX^2_3$, $R^1_2Sn$, or $R^1SnX^2$); or alternatively, an alkylaluminum compound ($AlX^2_2R^1$, $AlX^2R^1_2$, $AlR^1_3$, $Al^2X^2_5R^1$, $Al_2X^2_3R^1_3$, or $Al_2X^2R^1_5$). In some aspects, the alkylmetal compound of the catalyst system can comprise, can consist essentially of, or can be, an alkyllithium ($R^1Li$), an alkylsodium ($R^1Na$), an alkylpotassium ($R^1K$), an alkylmagnesium halide ($R^1MgX^2$), a dialkylmagnesium ($R^1_2Mg$), an alkylcopper halide ($R^1CuX^2$), a dialkylcopper ($R^1_2Cu$), an alkylzinc halide ($R^1ZnX^2$), a dialkylzinc ($R^1_2Zn$), an alkyltin halide ($R^1_3SnX^2$, $R^1_2SnX^2_2$, $R^1_2SnX^2_3$, $R^1_2Sn$, or $R^1SnX^2$), a dialkyltin ($R^1_2Sn$), a tetraalkyltin ($R^1_4Sn$), an alkylaluminum dihalide ($AlX^2_2R^1$), a dialkylaluminum halide ($AlX^2R^1_2$), a trialkylaluminum ($AlR^1_3$), an alkylaluminum sesquihalide ($Al_2X^2_3R^1$), an alkylaluminum dialkoxide ($AlX^2_2R^1$), a dialkylaluminum alkoxide ($AlX^2R^1_2$), or an aluminoxane; alternatively, an alkyllithium ($R^1Li$), an alkylsodium ($R^1Na$), an alkylpotassium ($R^1K$), a dialkylmagnesium ($R^1_2Mg$), a dialkylzinc ($R^1_2Zn$), an alkylaluminum dihalide ($AlX^2_2R^1$), a dialkylaluminum halide ($AlX^2R^1_2$), a trialkylaluminum ($AlR^1_3$), or an alkylaluminum sesquihalide ($Al_2X^2_3R^1_3$); alternatively, an alkyllithium ($R^1Li$), an alkylsodium ($R^1Na$), an alkylpotassium ($R^1K$); alternatively, an alkylmagnesium halide ($R^1MgX^2$) or a dialkylmagnesium ($R^1_2Mg$); alternatively, a diakyltin ($R^1_2Sn$), a tetraalkyl tin ($R^1_4Sn$); alternatively, an alkylzinc compound ($R^1_2Zn$ or $R^1ZnX^2$) and an alkylaluminum compound ($AlX^2_2R^1$, $AlX^2R^1_2$, $AlR^1_3$, $Al_2X^2_5R^1$, $Al_2X^2_3R^1_3$, or $Al_2X^2R^1_5$); alternatively, an alkylaluminum dihalide ($AlX^2_2R^1$), a dialkylaluminum halide ($AlX^2R^1_2$), an alkylaluminum sesquihalide ($Al_2X^2_3R^1_3$), a trialkylaluminum ($AlR^1_3$), or an aluminoxane; alternatively, an alkyllithium ($R^1Li$); alternatively, an alkylsodium ($R^1Na$); alternatively, an alkylpotassium ($R^1K$); alternatively, an alkylmagnesium halide ($R^1MgX^2$); alternatively, a dialkylmagnesium ($R^1_2Mg$); alternatively, an alkylzinc halide ($R^1ZnX^2$); alternatively, a dialkylzinc ($R^1_2Zn$); alternatively, an alkylaluminum dihalide ($AlX^2_2R^1$); alternatively, a dialkylaluminum halide ($AlX^2R^1_2$); alternatively, an alkylaluminum sesquihalide ($Al_2X^2_3R^1_3$); alternatively, an alkylaluminum dialkoxide ($AlX^2_2R^1$); alternatively, a dialkylaluminum alkoxide ($AlX^2R^1_2$); alternatively, a trialkylaluminum ($AlR^1_3$); or alternatively, an aluminoxane.

Generally, each halide of any hydrocarbylmetal halide (or alkylmetal halide) can be any halide. Each halide of any alkylmetal halide disclosed herein independently can be fluoride, chloride, bromide, or iodide; alternatively, chloride, bromide, or iodide; alternatively, fluoride; alternatively, chloride; alternatively, bromide; or alternatively, iodide.

Each alkyl group of any alkylmetal compound disclosed herein independently can be a $C_1$ to $C_{20}$, a $C_1$ to $C_{10}$, or a $C_1$ to $C_6$ alkyl group. In an aspect, each alkyl group of any alkylmetal compound disclosed herein independently can be a methyl group, an ethyl group, a propyl group, a butyl group, a pentyl group, a hexyl group, a heptyl group, or an octyl group; alternatively, a methyl group, an ethyl group, a butyl group, a hexyl group, or an octyl group. In some aspects, each alkyl group(s) of any alkylmetal compound disclosed herein independently can be a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

Each alkoxide of any alkylmetal alkoxide disclosed herein independently can be a $C_1$ to $C_{20}$, a $C_1$ to $C_{10}$, or a $C_1$ to $C_6$ alkoxide. In an aspect, each alkoxide of any alkylmetal alkoxide disclosed herein independently can be a methoxide, an ethoxide, a propoxide, a butoxide, a pentoxide, a hexoxide, a heptoxide, or an octoxide; alternatively, a methoxide, an ethoxide, a butoxide, a hexoxide, or an octoxide. In some aspects, each alkoxide group of any alkylmetal alkoxide disclosed herein independently can be a methoxide, an ethoxide, an n-propoxide, an n-butoxide, an iso-butoxide, an n-hexoxide, or an n-octoxide; alternatively, a methoxide, an ethoxide, an n-butoxide, or an iso-butoxide; alternatively, a methoxide; alternatively, an ethoxide; alternatively, an n-propoxide; alternatively, an n-butoxide; alternatively, an iso-butoxide; alternatively, an n-hexoxide; or alternatively, an n-octoxide.

The hydrocarbyllithium compound (or alkyllithium compound) which can be utilized as the hydrocarbylmetal compound can comprise, can consist essentially of, or can be, methyllithium, n-butyllithium, sec-butyllithium, tert-butyllithium; alternatively, methyllithium; alternatively, n-butyllithium; alternatively, sec-butyllithium; or alternatively, tert-butyllithium. The hydrocarbylsodium compound (or alkylsodium compound) which can be utilized as the hydrocarbylmetal compound can comprise, can consist essentially of, or can be, methylsodium, n-butylsodium, sec-butylsodium, tert-butylsodium; alternatively, methylsodium; alternatively, n-butylsodium; alternatively, sec-butylsodium; or alternatively, tert-butylsodium. The hydrocarbylpotassium compound (or alkylpotassium compound) which can be utilized as the hydrocarbylmetal compound can comprise, can consist essentially of, or can be, methylpotassium, n-butylpotassium, sec-butylpotassium, tert-butylpotassium; alternatively, methylpotassium; alternatively, n-butylpotassium; alternatively, sec-butylpotassium; or alternatively, tert-butylpotassium.

The hydrocarbylmagnesium halide (or alkylmagnesium halide) which can be utilized as the hydrocarbylmetal compound can comprise, can consist essentially of, or can be, methylmagnesium halide, ethylmagnesiun halide, a propylmagnesium halide, or a butylmagnesium halide; alternatively, methylmagnesium halide; alternatively, ethylmagnesiun halide; alternatively, a propylmagnesium halide; alternatively, a butylmagnesium halide. The dihydrocarbylmagnesium (or dialkylmagnesium) which can be utilized as the hydrocarbylmetal compound can comprise, can consist essentially of, or can be, dimethylmagnesium, diethylmagnesium, a dipropyl magnesium, or a dibutylmagnesium; alternatively, dimethylmagnesium; alternatively, diethylmagnesium; alternatively, a dipropylmagnesium; or alternatively, a dibutylmagnesium.

The hydrocarbylzinc halide which can be utilized as the hydrocarbylmetal compound can comprise, can consist essentially of, or can be, a methylzinc halide, an ethylzinc halide, a propylzinc halide, a butylzinc halide, a pentylzinc halide, a hexylzince halide, a cyclopentylzinc halide, a cyclohexylzinc halide, a phenyl zinc halide, a toulylzinc halide, a xylylzinc halide, or a benzylzinc halide; alternatively, a methylzinc halide, an ethylzinc halide, a propylzinc halide, a butylzinc halide, a pentylzinc halide, or a hexylzince halide; alternatively, a cyclopentylzinc halide or a cyclohexylzinc halide; alternatively, a phenyl zinc halide, a toulylzinc halide, or a xylylzinc halide; alternatively, a methylzinc halide; alternatively, an ethylzinc halide; alternatively, a propylzinc halide; alternatively, a butylzinc halide; alternatively, a pentylzinc halide; alternatively, a hexylzince halide; alternatively, a cyclopentylzinc halide; alternatively, a cyclohexylzinc halide; alternatively, a phenyl zinc halide; alternatively, a toulylzinc halide; alternatively, a xylylzinc halide; or alternatively, a benzylzinc halide. The dihydrocarbylzinc which can be utilized as the hydrocarbylmetal compound can comprise, can consist essentially of, or can be, dimethylzinc, diethylzinc, a dipropylzinc, dibutylzinc, a dipentylzinc, a dihexylzinc, dicyclopenylzinc, dicyclohexylzinc, diphenylzinc, a ditoulylzinc, a dixylylzinc, or dibenzylzinc; alternatively, dimethylzinc, diethylzinc, a dipropylzinc, dibutylzinc, a dipentylzinc, or a dihexylzinc; alternatively, dicyclopentylzinc or dicyclohexylzinc; alternatively, diphenylzinc, a ditoulylzinc, a dixylylzinc; alternatively, or dibenzylzinc; alternatively, dimethylzinc;

alternatively, diethylzinc; alternatively, a dipropylzinc; alternatively, dibutylzinc; alternatively, a dipentylzinc; alternatively, a dihexylzinc; alternatively, dicyclopenylzinc; alternatively, dicyclohexylzinc; alternatively, diphenylzinc; alternatively, a ditoulylzinc; alternatively, a dixylylzinc; or alternatively, dibenzylzinc.

In an aspect, the hydrocarbylmetal compound in the catalyst system can be an alkylaluminum compound. Generally, the hydrocarbylaluminum compound which can be utilized as the hydrocarbylmetal compound in the catalyst system can have the formula $AlX^2_{3-n}R^1_n$, $Al_2X^2_{6-q}R^1_q$, or any combination thereof; alternatively, $AlX^2_nR^1_{3-n}$; or alternatively $Al_2X^2_qR^1_{6-q}$. $X^2$, $R^1$, n, and q of the formulas $AlX^2_{3-n}R^1_n$ and $Al_2X^2_{6-q}R^1_q$ are independent elements of the hydrocarbylaluminum compound having the formulas $AlX^2_{3-n}R^1_n$ and $Al_2X^2_{6-q}R^1_q$ and are independently described herein. The independent descriptions of $X^2$, $R^1$, n, and q can be utilized without limitation, and in any combination, to describe the hydrocarbylaluminum compounds having the formula $AlX^2_{3-n}R^1_n$ or $Al_2X^2_{6-q}R^1_q$. Within the formulas $AlX^2_{3-n}R^1_n$ and $Al_2X^2_{6-q}R^1_q$, each $R^1$ independently can be a $C_1$ to $C_{20}$, a $C_1$ to $C_{10}$, or a $C_1$ to $C_6$ hydrocarbyl group; or alternatively, a $C_1$ to $C_{20}$, a $C_1$ to $C_{10}$, or a $C_1$ to $C_6$ alkyl group (in which case the hydrocarbyl aluminum compound can be referred to as an alkylaluminum compound). In an aspect, each $R^1$ independently can be a methyl group, an ethyl group, a propyl group, a butyl group, a pentyl group, a hexyl group, a heptyl group, or an octyl group; alternatively, a methyl group, an ethyl group, a butyl group, a hexyl group, an octyl group; alternatively, a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group. Within the formulas $AlX^2_{3-n}R^1_n$ and $Al_2X^2_{6-q}R^1_q$, each $X^2$ independently can be fluoride, chloride, bromide, or iodide; alternatively, chloride, bromide, or iodide; alternatively, chloride; alternatively, bromide; or alternatively iodide. Within the formulas $AlX^2_{3-n}R^1_n$ and $Al_2X^2_{6-q}R^1_q$, n can be in a range from 1 to 3; alternatively, in a range from 1 to 2; alternatively, 1; alternatively, 2, or alternatively, 3. Within the formulas $AlX^2_{3-n}R^1_n$ and $Al_2X^2_{6-q}R^1_q$, q can be 1, 3, or 5; alternatively, 1; alternatively, 3; or alternatively, 5. In an aspect, the hydrocarbylaluminum (or alkylaluminum) compound having the formula $AlX^2_{3-n}R^1_n$ or $Al_2X^2_{6-q}R^1_q$, can comprise, consist essentially of, or can be, a trialkylaluminum, an alkylaluminum halide, or any combination thereof; alternatively, a trialkylaluminum; or alternatively, an alkylaluminum halide. The trialkylaluminum compound can comprise, can consist essentially of, or can be, trimethylaluminum, triethylaluminum, tripropylaluminum, tributylaluminum, trihexylaluminum, trioctylaluminum, or any combination thereof; alternatively, trimethylaluminum, triethylaluminum, tripropylaluminum, tri-n-butylaluminum, tri-isobutylaluminum, trihexylaluminum, tri-n-octylaluminum, or mixtures thereof; alternatively, triethylaluminum, tri-n-butylaluminum, tri-isobutylaluminum, trihexylaluminum, tri-n-octylaluminum, or any combination thereof; alternatively, triethylaluminum, tri-n-butylaluminum, trihexylaluminum, tri-n-octylaluminum, or any combination thereof; alternatively, trimethylaluminum; alternatively, triethylaluminum; alternatively, tripropylaluminum; alternatively, tri-n-butylaluminum; alternatively, tri-isobutylaluminum; alternatively, tri-hexylaluminum; or alternatively, tri-n-octylaluminum. The alkylaluminum halide can comprise, can consist essentially of, or can be, diethylaluminum chloride, diethylaluminum bromide, ethylaluminum dichloride, ethylaluminum sesquichloride, or any combination thereof; alternatively, diethylaluminum chloride, ethylaluminum dichloride, ethylaluminum sesquichloride, or any combination thereof; alternatively, diethylaluminum chloride; alternatively, diethylaluminum bromide; alternatively, ethylaluminum dichloride; or alternatively, ethylaluminum sesquichloride.

In some aspects, the hydrocarbylaluminum (or alkylaluminum) compound which can be utilized as the hydrocarbylmetal compound in the catalyst system can have the formula $AlX^2_{3-n}R^1_n$, $Al_2X^2_{6-q}R^1_q$, or any combination thereof (alternatively, $AlX^2_nR^1_{3-n}$; or alternatively $Al_2X^2_{6-q}R^1_q$) wherein at least a portion of (or all of) the $X^2$s can be an alkoxide, a carboxylate, a dihydrocarbylazanide, or an carboxamide anion; alternatively, alkoxide; alternatively, a carboxylate; alternatively, a dihydrocarbylazanide; or alternatively, or an carboxamide anion. $R^1$, n, and q of the formulas $AlX^2_{3-n}R^1_n$ and $Al_2X^2_{6-q}R^1_q$ are described herein as elements of the hydrocarbylaluminum (or alkylaluminum) compound and these independent descriptions of $R^1$, n, and q can be utilized without limitation, and in any combination, to describe the hydrocarbylaluminum compounds having the formula $AlX^2_{3-n}R^1_n$ or $Al_2X^2_{6-q}R^1_q$ where at least a portion of (or all of) the $X^2$s are an alkoxide, a carboxylate, a dihydrocarbylazanide, and/or an carboxamide anion. When only a portion of (or all of) the $X^2$s are an alkoxide, a carboxylate, a dihydrocarbylazanide, and/or an carboxamide anion, the remainder of the $X^2$s can be a halide; alternatively, fluoride, chloride, bromide, or iodide; alternatively, chloride, bromide, or iodide; alternatively, chloride; alternatively, bromide; or alternatively iodide. Specific alkoxides, for hydrocarbylaluminum (or alkylaluminum) compounds having the formula $AlX^2_{3-n}R^1_n$ and/or $Al_2X^2_{6-q}R^1_q$ where at least a portion of (or all of) the $X^2$s can be an alkoxide, can be a $C_1$ to $C_{20}$, a $C_1$ to $C_{10}$, or a $C_1$ to $C_6$ alkoxide; alternatively, a methoxide, an ethoxide, a propoxide, a butoxide, a pentoxide, a hexoxide, a heptoxide, or an octoxide; alternatively, a methoxide, a ethoxide, a butoxide, a hexoxide, or an octoxide; alternatively, a methoxide, an ethoxide, an n-propoxide, an n-butoxide, an iso-butoxide, an n-hexoxide, or an n-octoxide; alternatively, a methoxide, an ethoxide, an n-butoxide, or an iso-butoxide; alternatively, a methoxide; alternatively, an ethoxide; alternatively, an n-propoxide; alternatively, an n-butoxide; alternatively, an iso-butoxide; alternatively, an n-hexoxide; or alternatively, an n-octoxide. Specific carboxylates, for hydrocarbylaluminum (or alkylaluminum) compounds having the formula $AlX^2_{3-n}R^1_n$ and/or $Al_2X^2_{6-q}R^1_q$ where at least a portion of (or all of) the $X^2$s can be an carboxylate, can be $C_2$ to $C_{20}$, $C_2$ to $C_{10}$, or $C_2$ to $C_6$ carboxylate; alternatively acetate, propanoate, a butanoate, a pentonate, a hexanoate, a heptanoate, octanoate, a benzoate, a methylbenoate, a dimethylbenzoate, or phenylactetate; alternatively, acetate, propanoate, a butanoate, a pentonate, a hexanoate, a heptanoate, or octanoate; alternatively, benzoate, a methylbenzoate, or dimethylbenzoate; or alternatively, phenylacetate. Specific dihydrocarbylazanides, for hydrocarbylaluminum (or alkylaluminum) compounds having the formula $AlX^2_{3-n}R^1_n$ and/or $Al_2X^2_{6-q}R^1_q$ where at least a portion of (or all of) the $X^2$s can be an dihydrocarbylazanides, can be $C_2$ to $C_{20}$, $C_2$ to $C_{10}$, or $C_2$ to $C_6$ dihydrocarbylazanide; alternatively, dimethylazanide, diethylazanide, a dipropylazanide, pyrrolidine azanide, piperidine azanide, diphenylazanide, a ditoluylazanide, a dixylyazanide, or dibenzylazanide; alternatively, dimethylazanide, diethylazanide, or a dipropylazanide; alternatively, pyrrolidine azanide or piperidine azanide; alternatively, diphenylazanide, a ditoluylazanide, a dixylyazanide; or alternatively dibenzylazanide. Specific carboxamide anions, for hydrocarbylaluminum (or alkylaluminum) compounds having the formula $AlX^2_{3-n}R^1_n$ and/or $Al_2X^2_{6-q}R^1_q$ where at least a portion of (or all of) the $X^2$s can be an carboxamide anion, can be $C_2$ to $C_{20}$, $C_2$ to $C_{10}$, or $C_2$ to $C_6$ carboxylamide anion; alternatively, dimethylformamide anion, diethylformamide anion, dimethylacetamide anion, diethylacetamide anion, 2-pyrrolidone anion, valerolactan anion, or caprolactam anion; alternatively, dimethylformamide anion, diethylformamide anion, dimethylacetamide anion, diethylacetamide anion; alternatively, 2-pyrrolidone anion, valerolactam anion, or caprolactam anion; alternatively, dimethylformamide anion; alternatively, dimethylacetamide anion; alternatively, 2-pyrrolidone anion; alternatively, valerolactam anion; or alternatively, caprolactam anion. When at least a portion of (or all of) the $X^2$s of the hydrocarbylaluminum (or alkylaluminum) compounds having the formula $AlX^2_{3-n}R^1_n$ and/or $Al_2X^2_{6-q}R^1_q$ are an alkoxide, a carboxylate, a dihydrocarbylazanide, and/or an carboxamide anion the molar ratio of alkoxide, carboxide, azanide, and/or amide anion to aluminum can be in a range from 0.1:1 to 1:1, 0.1:1 to 0.75:1, or from 0.1:1 to 0.5:1.

In aspects, where the hydrocarbylaluminum (or alkylaluminum) compound has the formula $AlX^2_{3-n}R^1_n$ or $Al_2X^2_{6-q}R^1_q$ and at least a portion of (or all of) the $X^2$s are an alkoxide, a carboxylate, a dihydrocarbylazanide, and/or an carboxamide anion, the hydrocarbylaluminum (or alkylaluminum) compound having the formula $AlX^2_{3-n}R^1_n$ or $Al_2X^2_{6-q}R^1_q$ can be generated in situ. These in situ generated hydrocarbylaluminum (or alkylaluminum) compounds can be formed by contacting an appropriate alcohol, a carboxylic acid or a simple ester of a carboxylic acid, an amine, and/or an amide with a hydrocarbylaluminum (or alkylaluminum) compound having the formula $AlX^2_{3-n}R^1_n$ or $Al_2X^2_{6-q}R^1_q$; where i) each $R^1$ independently any hydrocarbyl or alkyl $R^1$ group described herein for the hydrocarbylaluminum (or alkylaluminum) compound having the formula $AlX^2_{3-n}R^1_n$ or $Al_2X^2_{6-q}R^1_q$, ii) each $X^2$ independently can be any halide described herein for the hydrocarbylaluminum (or alkylaluminum) compound having the formula $AlX^2_{3-n}R^1_n$ or $Al_2X^2_{6-q}R^1_q$, iii) n can have any value described herein for the hydrocarbylaluminum (or alkylaluminum) compound having the formula $AlX^2_{3-n}R^1_n$ or $Al_2X^2_{6-q}R^1_q$, and iv) q can have any value described herein for the hydrocarbylaluminum (or alkylaluminum) compound having the formula $AlX^2_{3-n}R^1_n$ or $Al_2X^2_{6-q}R^1_q$. The alcohol that can be utilized to generate the in situ generated hydrocarbylaluminum (or alkylaluminum) compound can be methanol, ethanol, a propanol, a butanol, a pentanol, a hexanol, a heptanol, or an octanol; alternatively, methanol, ethanol, a butanol, a hexanol, or an octanol; alternatively, methanol, ethanol, n-propanol, n-butanol, iso-butanol, n-hexanol, or n-octanol; alternatively, methanol, ethanol, n-butanol, or iso-butanol; alternatively, methanol; alternatively, ethanol; alternatively, n-propanol; alternatively, n-butanol; alternatively, iso-butanol; alternatively, n-hexanol; or alternatively, n-octanol. The carboxylic acid or carboxylic acid of the simple ester of a carboxylic acid that can be utilized to generate the in situ generated hydrocarbylaluminum (or alkylaluminum) compound can be $C_2$ to $C_{20}$, $C_2$ to $C_{10}$, or $C_2$ to $C_6$ carboxylic acid; alternatively acetic acid, propionic acid, a butanoic acid, a pentanoic acid, a hexanoic acid, a heptanoic acid, an octanoic acid, benzoic acid, a methylbenzoic acid, a dimethylbenzoic acid, or phenylacetic acid; alternatively, acetic acid, propanoic acid, a butanoic acid, a pentanoic acid, a hexanoic acid, a heptanoic acid, or an octanoic acid; alternatively, benzoic acid, a methylbenzoic acid, or a dimethylbenzoic acid; or alternatively, phenylacetic acid. Generally, the alcohol of the alcohol derived portion of the simple ester of a carboxylic acid can be methanol and/or ethanol; alternatively, methanol; or ethanol. The amine that can be utilized to generate the in situ generated hydrocarbylaluminum (or alkylaluminum) compound having dihydrocarbylazanide can be a $C_2$ to $C_{20}$, $C_2$ to $C_{10}$, or $C_2$ to $C_6$ amine; alternatively, dimethyl amine, diethyl amine, a dipropyl amine, pyrrolidine, piperidine, diphenyl amine, a ditoluyl amine, a dixyly amine, or dibenzyl amine; alternatively, dimethyl amine, diethyl amine, or a dipropyl amine; alternatively, pyrrolidine or piperidine; alternatively, diphenyl amine, a ditoluyl amine, a dixyly amine; or alternatively dibenzyl amine. The amide that can be utilized to generate the in situ generated hydrocarbylaluminum (or alkylaluminum) compound having carboxamide anions can be a $C_2$ to $C_{20}$, $C_2$ to $C_{10}$, or $C_2$ to $C_6$ amide; alternatively, dimethylformamide, diethylformamide, dimethylacetamide, diethylacetamide, 2-pyrrolidone, valerolactam, or caprolactam; alternatively, dimethylformamide, diethylformamide, dimethylacetamide, diethylacetamide; alternatively, 2-pyrrolidone, valerolactam, or caprolactam; alternatively, dimethylformamide; alternatively, dimethylacetamide; alternatively, 2-pyrrolidone; alternatively, valerolactam; or alternatively, caprolactam. The molar ratio of the alcohol, carboxylic acid, carboxylic acid ester, amine, and/or amide to hydrocarbylaluminum (or alkylaluminum) compound having the formula $AlX^2_{3-n}R^1_n$ or $Al_2X^2_{6-q}R^1_q$ used to the prepare the in situ generated hydrocarbylaluminum (or alkylaluminum) compound having the formula $AlX^2_{3-n}R^1_n$ or $Al_2X^2_{6-q}R^1_q$ where at least a portion of (or all of) the $X^2$s are alkoxides, a carboxylates, a dihydrocarbylazanides, and/or an carboxamide anions can be in a range from 0.1:1 to 1:1, 0.1:1 to 0.75:1, or from 0.1:1 to 0.5:1.

Generally, the in situ generated hydrocarbylaluminum (or alkylaluminum) compound having the formula $AlX^2_{3-n}R^1_n$ or $Al_2X^2_{6-q}R^1_n$ can be formed in any way that can produce the desired in situ generated hydrocarbylaluminum (or alkylaluminum) compound. In an aspect, the in situ generated hydrocarbylaluminum (or alkylaluminum) compound having the formula $AlX^2_{3-n}R^1_n$ or $Al_2X^2_{6-q}R^1_q$ where at least a portion of (or all of) the $X^2$s are an alkoxide, a carboxylate, a dihydrocarbylazanide, and/or an carboxamide anion can be 1) formed by contacting the alcohol, carboxylic acid or simple ester of a carboxylic acid, amine, and/or amide with the appropriate (or desired) hydrocarbylaluminum (or alkylaluminum) compound having the formula $AlX^2_{3-n}R^1_n$ and/or $Al_2X^2_{6-q}R^1_q$ prior to contacting the in situ generated hydrocarbylaluminum (or alkylaluminum) compound with the zirconium compound component of the catalyst system.

The aluminoxane compound which can be utilized as the hydrocarbyl metal (or alkylmetal, or hydrocarbylaluminum, or alkylaluminum) compound of the catalyst system can comprise, can consist essentially of, or can be, methylaluminoxane (MAO), ethylaluminoxane, modified methylaluminoxane (MMAO), n-propylaluminoxane, iso-propyl-aluminoxane, n-butylaluminoxane, sec-butylaluminoxane, isobutylaluminoxane, t-butylaluminoxane, 1-pentylaluminoxane, 2-entylaluminoxane, 3-pentyl-aluminoxane, isopentylaluminoxane, neopentylaluminoxane, or any combination thereof. In some non-limiting aspects, the aluminoxane can comprise, can consist essentially of, or can be, methylaluminoxane (MAO), modified methylaluminoxane (MMAO), isobutyl aluminoxane, t-butyl aluminoxane, or any combination thereof; alternatively, methylaluminoxane (MAO); alternatively, ethylaluminoxane; alternatively, modified methylaluminoxane (MMAO); alternatively, n-propylaluminoxane; alternatively, iso-propylaluminoxane; alternatively, n-butylaluminoxane; alternatively, sec-butylaluminoxane; alternatively, iso-butylaluminoxane; alternatively, t-butyl aluminoxane; alternatively, 1-pentylaluminoxane; alternatively, 2-pentylaluminoxane; alternatively, 3-pentylaluminoxane; alternatively, iso-pentylaluminoxane; or alternatively, neopentylaluminoxane.

Non-limiting exemplary hydrocarbylaluminum (or alkylaluminum) compounds which can be utilized in the catalyst systems of the processes described herein can comprise, can consist essentially of, or can be $Al(CH_3)_3$, $Al(C_2H_5)_3$, $Al(C_3H_7)_3$, $Al(C_4H_9)_3$, $Al(C_5H_{11})_3$, $Al(C_6H_{13})_3$, $Al(C_8H_{17})_3$, $Al(C_2H_5)_2Cl$, $Al(C_2H_5)_2Br$, $Al(C_2H_5)_2I$, $Al(C_2H_5)Cl_2$, $Al(C_2H_5)Br_2$, $Al(C_2H_5)I_2$, $AlC_2H_5(OC_2H)_2$, $AlC_2H_5(OC_3H_7)_2$, $AlC_2H_5(OC_4H_9)_2$, $Al(OC_2H_5)_2Cl$, $Al(OC_3H_7)_2Cl$, $Al(OC_4H_9)_2Cl$, $Al(OC_2H_5)Cl_2$, $Al(OC_3H_5)Cl_2$, $Al(OC_4H_9)Cl_2$, $AlC_2H_5(OCOC_2H_5)_2$, $AlC_2H_5(OCOC_3H_7)_2$, $AlC_2H_5(OCOC_4H_9)_2$, $Al(OCOC_2H_5)_2Cl$, $Al(OCOC_3H_7)_2Cl$, $Al(OCOC_4H_9)_2Cl$, $Al(OCOC_2H_5)Cl_2$, $Al(OCOC_3H_7)Cl_2$, $Al(OCOC_4H_9)Cl_2$, $Al(C_2H_5)_2OC_2H_5$, $Al(C_2H_5)_2OC_3H_7$, $Al(C_2H_5)_2OC_4H_9$, $Al(C_2H_5)_2N(C_2H_5)_2$, $Al(C_2H)_2N(C_3H_7)_2$, $Al(C_2H_5)_2N(C_4H_9)_2$, $Al_2(CH_3)_3Cl_3$, $Al_2(CH_3)_3Br_3$, $Al_2(C_2H_5)_3Cl_3$, $Al_2(C_2H_5)_3Br_3$, $Al_2(C_2H_5)_3I_3$, $Al_2(C_2H_5)_2BrCl_2$, $Al_2(C_3H_7)_3Cl_3$, $Al_2(C_4H_9)_3Cl_3$, $Al_2(C_5H_7)_3Cl_3$, $Al_2(OCOC_4H_9)_3Cl_3$, or any combination thereof. In some aspects, the hydrocarbylaluminum (or alkylaluminum) compound can comprise, can consist essentially of, or can be, $Al(CH_3)_3$, $Al(C_2H)_3$, $Al(C_3H_7)_3$, $Al(C_4H)_3$, $Al(C_5H_{11})_3$, $Al(C_6H_{13})_3$, $Al(C_8H_{17})_3$, $Al(C_2H_5)_2Cl$, $Al(C_2H_5)_2Br$, $Al(C_2H_5)_2I$, $Al(C_2H_5)Cl_2$, $Al(C_2H_5)Br_2$, $Al(C_2H_5)I_2$, $Al_2(CH_3)_3Cl_3$, $Al_2(CH_3)_3Br_3$, $Al_2(C_2H_5)_3Cl_3$, $Al_2(C_2H_5)_3Br_3$, $Al_2(C_2H_5)_3I_3$, $Al_2(C_2H_5)_2BrCl_2$, $Al_2(C_3H_7)_3Cl_3$, $Al_2(C_4H_9)_3Cl_3$, $Al_2(C_5H_7)_3Cl_3$, or any combination thereof; alternatively, $AlC_2H_5(OC_2H_5)_2$, $AlC_2H_5(OC_3H_7)_2$, $AlC_2H(OC_4H_9)_2$, $AlC_2H(OCOC_2H_5)_2$, $AlC_2H_5(OCOC_3H_7)_2$, $AlC_2H_5(OCOC_4H_9)_2$, $Al(C_2H_5)_2OC_2H_5$, $Al(C_2H)_2OC_3H_7$, $Al(C_2H_5)_2OC_4H_9$, $Al(C_2H_5)_2N(C_2H_5)_2$, $Al(C_2H_5)_2N(C_3H_7)_2$, $Al(C_2H_5)_2N(C_4H_9)_2$, or any combination thereof; alternatively, $AlC_2H_5(OC_2H_5)_2$, $AlC_2H_5(OC_3H_7)_2$, $AlC_2H_5(OC_4H_9)_2$, or any combination thereof; or alternatively, $AlC_2H_5(OCOC_2H_5)_2$, $AlC_2H_5(OCOC_3H_7)_2$, $AlC_2H_5(OCOC_4H_9)_2$, $Al(C_2H_5)_2OC_2H_5$, $Al(C_2H_5)_2OC_3H_7$, $Al(C_2H_5)_2OC_4H_9$, or any combination thereof; alternatively, $Al(C_2H_5)_2N(C_2H_5)_2$, $Al(C_2H_7)_2N(C_3H_7)_2$, $Al(C_2H_5)_2N(C_4H_9)_2$, or any combination thereof. In other aspects, the hydrocarbylaluminum (or alkylaluminum) compound can comprise, can consist essentially of, or can be, $Al_2(CH_3)_3Cl_3$, $Al_2(CH_3)_3Br_3$, $Al_2(C_2H_5)_3Cl_3$, $Al_2(C_2H_5)_3Br_3$, $Al_2(C_2H_5)_3I_3$, $Al_2(C_2H_5)_2BrCl_2$, $Al_2(C_3H_7)_3Cl_3$, $Al_2(C_4H_9)_3Cl_3$, $Al_2(C_5H_5)_3Cl_3$, or any combination thereof; or alternatively, $Al(C_2H_5)_3$, $Al(C_2H_5)_2Cl$, $Al(C_2H_5)Cl_2$, $Al_2(C_2HCl_3)$, or any combination thereof.

The molar ratio of the metal of the hydrocarbylmetal (or hydrocarbylaluminum, or alkylaluminum) compound to zirconium of the zirconium compound (also referred to herein as the M:Zr molar ratio) to can be any value that provides a catalyst system which can form an oligomer product. In an aspect, the minimum M:Zr (or Al:Zr) molar ratio can be 0.1:1, 0.2:1, 0.6:1, 1:1, 2:1 10:1; alternatively, or additionally, the maximum M:Zr (or Al:Zr) molar ratio can be 100:1 75:1, 50:1 25:1, 15:1, or 10:1. Generally, the M:Zr (or Al:Zr) molar ratio can range from any minimum M:Zr (or Al:Zr) molar ratio disclosed herein to any maximum M:Zr (or Al:Zr) molar ratio disclosed herein. Accordingly, suitable non-limiting ranges for the M:Zr (or Al:Zr) molar ratios can range from 0.1:1 to 100:1, 0.2:1 to 75:1, 0.6:1 to 25:1, 1:1 to 50:1, 2:1 to 25:1, 1:1 to 15:1, 2:1 to 10:1, 10:1 to 50:1, or 10:1 to 25:1. Other appropriate M:Zr (or Al:Zr) molar ranges are readily apparent from this disclosure.

In some aspects, the catalyst system can further comprise (or have as a component) a neutral non-ionic organic modifier. Generally, the neutral non-ionic organic modifier can be any neutral non-ionic organic modifier which in conjunction with the zirconium compound and the hydrocarbylmetal compound can form an oligomer product. The neutral non-ionic organic modifier can comprise, consist essentially of, or can be, an ether, an ester, a ketone, an aldehyde, an alcohol, an anhydride, an acid chloride, a nitrile, a sulfide, a disulfide, a phosphine, an amine, or an amide; alternatively, an ether; alternatively, an ester, alternatively, a ketone; alternatively, an aldehyde; alternatively, an alcohol; alternatively, a sulfide; alternatively, a disulfide, alternatively, a nitrile; alternatively, a phosphine; alternatively, an amine; or alternatively, an amine.

The ether which can be utilized as the neutral non-ionic organic modifier can be, a $C_2$ to $C_{20}$, $C_2$ to $C_{15}$, or $C_2$ to $C_{10}$, ether. The sulfide which can be utilized as the neutral non-ionic organic modifier can be, can be a $C_2$ to $C_{20}$, $C_2$ to $C_{15}$, or $C_2$ to $C_{10}$ sulfide. The disulfide which can be utilized as the neutral non-ionic organic modifier can be, can be a $C_2$ to $C_{20}$, $C_2$ to $C_{15}$, or $C_2$ to $C_{10}$ disulfide. The ether can have structure $R^{11}OR^{12}$. The sulfide can have structure $R^{11}SR^{12}$. The disulfide can have structure $R^{11}SSR^{12}$. Each $R^{11}$ and $R^{12}$ of the ether, sulfide, and/or disulfide independently can be $C_1$ to $C_{15}$, $C_1$ to $C_{10}$, or $C_1$ to $C_5$ hydrocarbyl groups, $C_1$ to $C_{15}$, $C_1$ to $C_{10}$, or $C_1$ to $C_5$ alkyl groups, $C_5$ to $C_{15}$ or $C_5$ to $C_{10}$ cycloalkyl groups, $C_6$ to $C_{15}$ or $C_6$ to $C_{10}$ aryl groups, or $C_7$ to $C_{15}$ or $C_7$ to $C_{10}$ aralkyl groups. In a non-limiting aspect, the ether which can be utilized as the neutral non-ionic organic modifier can comprise, can consist essentially of, or can be, dimethyl ether, diethyl ether, a dipropyl ether, a dibutyl ether, diphenyl ether, a ditolyl ether, a dixylyl ether, tetrahydrofuran, tetrahydropyran, a dioxane, furan, benzofuran, isobenzofuran, dibenzofuran, or any combination thereof. In some aspects, the ether which can be utilized as the neutral non-ionic organic modifier can comprise, can consist essentially of, or can be, dimethyl ether, diethyl ether, a dipropyl ether, a dibutyl ether, diphenyl ether, a ditolyl ether, a dixylyl ether, or any combination thereof; alternatively, tetrahydrofuran, tetrahydropyran, a dioxane, or any combination thereof; alternatively, furan, benzofuran, isobenzofuran, dibenzofuran, or any combination thereof; alternatively, diethyl ether; alternatively, a dipropyl ether; alternatively, a dibutyl ether; alternatively, diphenyl ether; alternatively, alternatively, a ditolyl ether; alternatively, a dixylyl ether, tetrahydrofuran; alternatively, tetrahydropyran; alternatively, a dioxane; alternatively, furan; alternatively, benzofuran; alternatively, isobenzofuran; or alternatively, dibenzofuran. In a non-limiting aspect, the sulfide which can be utilized as the neutral non-ionic organic modifier can comprise, consist essentially of, or can be, dimethyl sulfide, diethyl sulfide, a dipropyl sulfide, a dihexyl sulfide, a dioctyl sulfide, dicyclohexyl sulfide, diphenyl sulfide, thiophene, a methyl thiophene (e.g., 2-methyl thiophene or 3-methyl thiophene), a dimethyl thiophene (e.g., 2,3-dimethyl thiophene), an ethyl thiophene, benzothiophene, tetrahydrothiophene, thiopyran, or any combination thereof; alternatively, alternatively, dimethyl sulfide, diethyl sulfide, a dipropyl sulfide, a dibutyl sulfide, a dihexyl sulfide, a dioctyl sulfide, dicyclohexyl sulfide, diphenyl sulfide, or any combination thereof; alternatively thiophene, a methyl thiophene (e.g., 2-methyl thiophene or 3-methyl thiophene), a dimethyl thiophene (e.g., 2,3-dimethyl thiophene), an ethyl thiophene, benzothiophene, tetrahydrothiophene, thiopyran, or any combination thereof; alternatively, dimethyl sulfide; alternatively, diethyl sulfide; alternatively, dibutyl sulfide; alternatively, a dihexyl sulfide; alternatively, a dioctyl sulfide; alternatively, dicyclohexyl sulfide; alternatively, diphenyl sulfide; alternatively, thiophene; alternatively, tetrahydrothiophene; or alternatively, thiourea. In an aspect, the disulfide can comprise, consist essentially of, or can be, dimethyl disulfide, diethyl disulfide, a dipropyl disulfide, a dibutyl disulfide, a dihexyl disulfide, a dioctyl disulfide, dicyclohexyl disulfide, ethylmethyl disulfide, diphenyl disulfide, methylphenyl disulfide, or any combination thereof; alternatively, dimethyl disulfide, diethyl disulfide, a dipropyl disulfide, a dibutyl disulfide, a dihexyl disulfide, a dioctyl disulfide, dicyclohexyl disulfide, ethylmethyl disulfide, diphenyl disulfide, methylphenyl disulfide, or any combination thereof; alternatively, dimethyl disulfide; alternatively, diethyl disulfide; alternatively, a dibutyl disulfide; alternatively, a dioctyl disulfide; or alternatively, diphenyl disulfide.

The ester which can be utilized as the neutral non-ionic organic modifier can be a $C_3$ to $C_{20}$, $C_3$ to $C_{15}$, or $C_3$ to $C_{10}$, ester. The ester can have structure $R^{13}(C=O)OR^{14}$. $R^{13}$ and $R^{14}$ of the ester independently can be $C_1$ to $C_{15}$, $C_1$ to $C_{10}$, or $C_1$ to $C_5$ hydrocarbyl groups, $C_1$ to $C_{15}$, $C_1$ to $C_{10}$, or $C_1$ to $C_5$ alkyl groups, $C_5$ to $C_{15}$ or $C_5$ to $C_{10}$ cycloalkyl groups, $C_6$ to $C_{15}$ or $C_6$ to $C_{10}$ aryl groups, or $C_7$ to $C_{15}$ or $C_7$ to $C_{10}$ aralkyl groups. The ester which can be utilized as the neutral non-ionic organic modifier can be a $C_1$ to $C_{15}$, $C_1$ to $C_{10}$, or $C_1$ to $C_5$ hydrocarbyl, $C_1$ to $C_{15}$, $C_1$ to $C_{10}$, or $C_1$ to $C_5$ alkyl, $C_5$ to $C_{15}$ or $C_5$ to $C_{10}$ cycloalkyl, $C_6$ to $C_{15}$ or $C_6$ to $C_{10}$ aryl, or $C_2$ to $C_{15}$ or $C_7$ to $C_{10}$ aralkyl ester of a $C_1$ to $C_{15}$, $C_1$ to $C_{10}$, or $C_1$ to $C_5$ hydrocarbyl, $C_1$ to $C_{15}$, $C_1$ to $C_{10}$, or $C_1$ to $C_5$ alkyl, $C_6$ to $C_{15}$ or $C_6$ to $C_{10}$ aryl, or $C_7$ to $C_{15}$ or $C_7$ to $C_{10}$ aralkyl carboxylic acid. In non-limiting aspects, the ester which can be utilized as the neutral non-ionic organic modifier can comprise, consist essentially of, or can be, a methyl, ethyl, propyl, butyl, pentyl, hexyl, heptyl, octyl, nonyl, decyl, undecyl, dodecyl, tridecyl, phenyl, toluyl, xylyl, or benzyl acetate, propionate, butanoate, pentanoate, hexanoate, heptanoate, octanoate, nonanoate, decanoate, benzoate, methyl benzoate, dimethyl benzoate, or naphtanoate; alternatively, a methyl, ethyl, propyl, butyl, pentyl, hexyl, heptyl, octyl, nonyl, decyl, undecyl, dodecyl, or tridecyl, acetate, propionate, butanoate, pentanoate, hexanoate, heptanoate, octanoate, nonanoate, decanoate; alternatively, a phenyl, toluyl, xylyl, or benzyl acetate, propionate, butanoate, pentanoate, hexanoate, heptanoate, octanoate, nonanoate, or decanoate; or alternatively, a methyl, ethyl, propyl, butyl, pentyl, hexyl, heptyl, octyl, nonyl, decyl, undecyl, dodecyl, or tridecyl benzoate, methyl benzoate, dimethyl benzoate, or naphtanoate. In some aspects, the ester which can be utilized as the neutral non-ionic organic modifier can be a $C_4$ to $C_{20}$, $C_4$ to $C_{15}$, or $C_4$ to $C_{10}$ cyclic ester; alternatively, butyrolactone, valerolactone, phthalide, or any combination thereof; alternatively, butyrolactone; alternatively, valerolactone; or alternatively, phthalide.

The aldehyde which can be utilized as the neutral non-ionic organic modifier can be a $C_2$ to $C_{20}$, $C_2$ to $C_{15}$, or $C_2$ to $C_{10}$ aldehyde. The ketone which can be utilized as the neutral non-ionic organic modifier can be a $C_3$ to $C_{20}$, $C_3$ to $C_{15}$, or $C_3$ to $C_{10}$ ketone. The aldehyde can have structure $R^{15}(C=O)H$. The ketone can have structure $R^{15}(C=O)R^{16}$. $R^{15}$ of the aldehyde, and $R^{15}$ and $R^{16}$ of the ketone independently can be $C_1$ to $C_{15}$, $C_1$ to $C_{10}$, or $C_1$ to $C_5$ hydrocarbyl groups, $C_1$ to $C_{15}$, $C_1$ to $C_{10}$, or $C_1$ to $C_5$ alkyl groups, $C_5$ to $C_{15}$ or $C_5$ to $C_{10}$ cycloalkyl groups, $C_6$ to $C_{15}$ or $C_6$ to $C_{10}$ aryl groups, or $C_7$ to $C_{15}$ or $C_7$ to $C_{10}$ aralkyl groups. In a non-limiting aspect, the aldehyde which can be utilized as the neutral non-ionic organic modifier can comprise, consist essentially of, formaldehyde, acetaldehyde, propionaldehyde, a butyraldehyde, benzaldehyde, a tolualdehyde, a xylylaldehyde, a furaldehyde, or any combination thereof; alternatively, formaldehyde, acetaldehyde, propionaldehyde, a butyraldehyde, or any combination thereof; alternatively, benzaldehyde, a tolualdehyde, a xylylaldehyde, or any combination thereof; alternatively, formaldehyde; alternatively, acetaldehyde; alternatively, propionaldehyde; alternatively, a butyraldehyde; alternatively, benzaldehyde; alternatively, a tolualdehyde; alternatively, a xylylaldehyde; alternatively, a furaldehyde. The ketone which can be utilized as the neutral non-ionic organic modifier can comprise, consist essentially of, or can be propanone, butanone, a pentanone, a hexanone, a heptanone, a octanone, a nonanone, a decanone, phenylethanone, phenylpropanone, benzophenone, or any combination thereof; alternatively, propanone, butanone, a pentanone, a hexanone, a heptanone, a octanone, a nonanone, a decanone, or any combination thereof; alternatively, phenylethanone, phenylpropanone, benzophenone, or any combination thereof; alternatively, propanone; alternatively, butanone; alternatively, a pentanone; alternatively, a hexanone; alternatively, a heptanone; alternatively, a octanone; alternatively, a nonanone; alternatively, a decanone; alternatively, phenylethanone; alternatively, phenylpropanone; or alternatively, benzophenone.

The acid halides which can be utilized as the neutral non-ionic organic modifier can be a $C_2$ to $C_{20}$, $C_2$ to $C_{15}$, or $C_2$ to $C_{10}$ acid halide. The anhydride, which can be utilized as the neutral non-ionic organic modifier can be a $C_2$ to $C_{20}$, $C_2$ to $C_{15}$, or $C_2$ to $C_{10}$ anhydride. The acid halide can have the structure $R^{17}(C=O)X^{10}$. The anhydride can have the structure $R^{17}(C=O)O(C=O)R^{17}$. $X^{10}$ of the acid halide can be chloride, bromide, or iodide; alternatively, chloride; alternatively, bromide; or alternatively, iodide. Each $R^{17}$ of the acid halide and anhydrides independently can be a $C_1$ to $C_{15}$, $C_1$ to $C_{10}$, or $C_1$ to $C_5$ hydrocarbyl group, a $C_1$ to $C_{15}$, $C_1$ to $C_{10}$, or $C_1$ to $C_5$ alkyl group, a $C_5$ to $C_{15}$ or $C_5$ to $C_{10}$ cycloalkyl group, a $C_6$ to $C_{15}$ or $C_6$ to $C_{10}$ aryl group, or a $C_7$ to $C_{15}$ or $C_7$ to $C_{10}$ aralkyl group. In a non-limiting aspect, the acid halide which can be utilized as the neutral non-ionic organic modifier can comprise, consist essentially of, or can be acetyl chloride, acetyl bromide, propionyl chloride, propionyl bromide, a butyryl chloride, a valeroyl chloride, hexanoyl chloride, benzoyl chloride, benzoyl bromide, a methylbenzoyl chloride, a dimethyl benzoyl chloride, or any combination thereof; alternatively, acetyl chloride, acetyl bromide, propionyl chloride, propionyl bromide, a butyryl chloride, a valeroyl chloride, hexanoyl chloride, or any combination thereof; alternatively, benzoyl chloride, benzoyl bromide, a methylbenzoyl chloride, a dimethyl benzoyl chloride, or any combination thereof; alternatively, acetyl chloride; alternatively, acetyl bromide; alternatively, propionyl chloride; alternatively, propionyl bromide; alternatively, a butyryl chloride; alternatively, a valeroyl chloride; alternatively, hexanoyl chloride; alternatively, benzoyl chloride; alternatively, benzoyl bromide; alternatively, a methylbenzoyl chloride; or alternatively, a dimethyl benzoyl chloride.

In a non-limiting aspect, the anhydride which can be utilized as the neutral non-ionic organic modifier can be ethanoic anhydride, propanoic anhydride, a butanoic anhydride, a hexanoic anhydride, maleic anhydride, succinic anhydride, glutaric anhydride, benzoic anhydride, a methylbenzoic anhydride, a dimethyl benzoic anhydride, phthalic anhydride, homophthalic anhydride, or any combination thereof; alternatively, ethanoic anhydride, propanoic anhydride, a butanoic anhydride, a hexanoic anhydride; alternatively, maleic anhydride, succinic anhydride, glutaric anhydride, or any combination thereof; alternatively, benzoic anhydride, a methylbenzoic anhydride, a dimethyl benzoic anhydride, or any combination thereof; alternatively, phthalic anhydride, homophthalic anhydride, or any combination thereof; alternatively, ethanoic anhydride; alternatively, propanoic anhydride; alternatively, a butanoic anhydride; alternatively, a hexanoic anhydride; alternatively, maleic anhydride; alternatively, succinic anhydride; alternatively, glutaric anhydride; alternatively, benzoic anhydride; alternatively, a methylbenzoic anhydride; alternatively, a dimethyl benzoic anhydride; alternatively, phthalic anhydride; or alternatively, homophthalic anhydride.

The nitrile which can be utilized as the neutral non-ionic organic modifier can be a $C_2$ to $C_{20}$, $C_2$ to $C_{15}$, or $C_2$ to $C_{10}$ nitrile. The nitrile can have the structure $R^{18}CN$. $R^{18}$ of the nitrile can be a $C_1$ to $C_{15}$, $C_1$ to $C_{10}$, or $C_1$ to $C_5$ hydrocarbyl group, a $C_1$ to $C_{15}$, $C_1$ to $C_{10}$, or $C_1$ to $C_5$ alkyl group, a $C_5$ to $C_{15}$ or $C_5$ to $C_{10}$ cycloalkyl group, a $C_6$ to $C_{15}$ or $C_6$ to $C_{10}$ aryl group, or a $C_7$ to $C_{15}$ or $C$; to $C_{10}$ aralkyl group. In a non-limiting aspect, the nitrile which can be utilized as the neutral non-ionic organic modifier can comprise, consist essentially of, or can be acetonitrile, propionitrile, a butyronitrile, benzonitrile, or any combination thereof; alternatively, acetonitrile; alternatively, propionitrile; alternatively, a butyronitrile; or alternatively, benzonitrile.

The phosphine which can be utilized as the neutral non-ionic organic modifier can be a $C_3$ to $C_{20}$, $C_3$ to $C_{15}$, or $C_3$ to $C_{10}$ phosphine. The phosphine can have the structure $(R^{19})_3P$. The amine can have the structure $(R^{19})_3N$. Each $R^{19}$ of the phosphine independently can be a $C_1$ to $C_{15}$, $C_1$ to $C_{10}$, or $C_1$ to $C_5$ hydrocarbyl group, a $C_1$ to $C_{15}$, $C_1$ to $C_{10}$, or $C_1$ to $C_5$ alkyl group, a $C_5$ to $C_{15}$ or $C_5$ to $C_{10}$ cycloalkyl group, a $C_6$ to $C_{15}$ or $C_6$ to $C_{10}$ aryl group, or a $C_7$ to $C_{15}$ or $C$; to $C_{10}$ aralkyl group. In a non-limiting aspect, the phosphine which can be utilized as the neutral non-ionic organic modifier can comprise, consist essentially of, or can be, trimethylphosphine, triethylphosphine, a tripropyl phosphine, a tributylphosphine, a trihexyl phosphine, a trioctylphosphine, tricyclopentylphosphine, tricyclohexylphosphine, triphenylphosphine, or any combination thereof; alternatively, trimethylphosphine, triethylphosphine, a tributylphosphine, a trihexyl phosphine, a trioctylphosphine, or any combination thereof; alternatively, tricyclopentylphosphine, tricyclohexylphosphine, or any combination thereof; alternatively, triethylphosphine; alternatively, a tributylphosphine; alternatively, a trihexyl phosphine; alternatively, a trioctylphosphine; alternatively, tricyclopentylphosphine; alternatively, tricyclohexylphosphine; or alternatively, triphenylphosphine.

The amine which can be utilized as the neutral non-ionic organic modifier can be a $C_1$ to $C_{20}$, $C_1$ to $C_{15}$, or $C_1$ to $C_{10}$ amine. The amine can have the structure $H_2NR^{20}$, $HN(R^{20})_2$, $N(R^{20})_3$, or any combination thereof; alternatively, $H_2NR^{20}$; alternatively, $HN(R^{20})_2$; or alternatively, $N(R^{20})_3$. Each $R^{20}$ of the amine having structure $H_2NR^{20}$, $HN(R^{20})_2$, or $N(R^{20})_3$ independently can be a $C_1$ to $C_{15}$, $C_1$ to $C_{10}$, or $C_1$ to $C_5$ hydrocarbyl group, a $C_1$ to $C_{15}$, $C_1$ to $C_{10}$, or $C_1$ to $C_5$ alkyl group, a $C_5$ to $C_{15}$ or $C_5$ to $C_{10}$ cycloalkyl group, a $C_6$ to $C_{15}$ or $C_6$ to $C_{10}$ aryl group, or a $C_7$ to $C_{15}$ or $C_7$ to $C_{10}$ aralkyl group. In a non-limiting aspect, the amine which can be utilized as the neutral non-ionic organic modifier can comprise, consist essentially of, or can be methylamine, ethylamine, a propylamine, a butylamine, a pentylamine, a hexylamine, a heptylamine, an octylamine, a decylamine, cyclopentylamine, cyclohexylamine, a piperidine, a methylpiperidine, a dimethylpiperidine, a trimethylpiperidine, a tetramethylpiperidine, aniline, benzylamine, a naphthylamine, dimethylamine, diethylamine, a dibutylamine, diphenylamine, methylphenylamine, trimethyl amine, triethyl amine, a tributyl amine, triphenyl amine, pyridine, a picoline, or any combination thereof; alternatively, methylamine, ethylamine, a propylamine, a butylamine, a pentylamine, a hexylamine, a heptylamine, an octylamine, a decylamine, cyclopentylamine, cyclohexylamine, aniline, benzylamine, a naphthylamine, dimethylamine, diethylamine, a dibutylamine, diphenylamine, methylphenylamine, or any combination thereof; alternatively, methylamine, ethylamine, a propylamine, a butylamine, a pentylamine, a hexylamine, a heptylamine, an octylamine, a decylamine, cyclopentylamine, cyclohexylamine, aniline, benzylamine, a naphthylamine, or any combination thereof; alternatively, dimethylamine, diethylamine, a dibutylamine, diphenylamine, methylphenylamine, or any combination thereof; alternatively, piperidine, a methylpiperidine, a dimethylpiperidine, a trimethylpiperidine, a tetramethylpiperidine, or any combination thereof; alternatively, trimethyl amine, triethyl amine, a tributyl amine, triphenyl amine, or any combination thereof; alternatively, pyridine, a picoline, or any combination thereof; alternatively, aniline, naphthyl amine, or any combination thereof; alternatively, dimethyl amine, diethyl amine, dibutyl amine, diphenyl amine, methylphenyl amine; or any combination thereof; alternatively, trimethyl amine, triethyl amine, tributyl amine, triphenyl amine, or any combination thereof; alternatively, methylamine; alternatively, ethylamine; alternatively, a propylamine; alternatively, a butylamine; alternatively, a pentylamine; alternatively, a hexylamine; alternatively, a heptylamine; alternatively, an octylamine; alternatively, a decylamine; alternatively, cyclopentylamine; alternatively, cyclohexylamine; alternatively, piperidine; alternatively, a methylpiperidine; alternatively, a dimethylpiperidine; alternatively, a trimethylpiperidine; alternatively, a tetramethylpiperidine; alternatively, aniline; alternatively, benzylamine; alternatively, naphthylamine; alternatively, dimethylamine; alternatively, diethylamine; alternatively, dibutylamine; alternatively, diphenylamine; alternatively, methylphenylamine; alternatively, trimethylamine; alternatively, triethylamine; alternatively, tributylamine; alternatively, triphenylamine; alternatively, pyridine; or alternatively, picoline.

The amide which can be utilized as the neutral non-ionic organic modifier can be a $C_2$ to $C_{20}$, $C_2$ to $C_{15}$, or $C_2$ to $C_{10}$ amide. The amide can have the structure $H(C=O)NHR^{22}$, $H(C=O)N(R^{22})_2$, $R^{21}(C=O)NH_2$, $R^{21}(C=O)NHR^{22}$, $R(C=O)N(R^{22})_2$, or any combination thereof; alternatively, $H(C=O)NHR^{22}$ or $H(C=O)N(R^{22})_2$, or any combination thereof; alternatively, $R^{21}(C=O)NH_2$, $R^{21}(C=O)NHR^{21}$, or $R(C=O)N(R^{21})_2$, or any combination thereof; alternatively, $H(C=O)NHR^{22}$; alternatively, $H(C=O)N(R^{22})_2$; alternatively, $R^{21}(C=O)NH_2$; alternatively, $R^{21}(C=O)NHR^{22}$, or alternatively, $R(C=O)N(R^{22})_2$. $R^{21}$ and each $R^{22}$ of the amide independently can be a $C_1$ to $C_{15}$, $C_1$ to $C_{10}$, or $C_1$ to $C_5$ hydrocarbyl group, a $C_1$ to $C_{15}$, $C_1$ to $C_{10}$, or $C_1$ to $C_5$ alkyl group, a $C_5$ to $C_{15}$ or $C_5$ to $C_{10}$ cycloalkyl group, a $C_6$ to $C_{15}$ or $C_6$ to $C_{10}$ aryl group, or a $C_7$ to $C_{15}$ or $C_7$ to $C_{10}$ aralkyl group. In a non-limiting aspect, the amide which can be utilized as the neutral non-ionic organic modifier can comprise, consist essentially of, or can be, N-methylformamide, N,N-dimethylformamide, N-ethylformamide, N,N-diethylformamide, an N-propylformamide, an N,N-dipropylformamide, an N-butylformamide, a N,N-dibutylformamide, N-phenylformamide, N,N-diphenylformamide, acetamide, N-methylacetamide, N,N-dimethylacetamide, N-ethylacetamide, N,N-diethylacetamide, a N-propylacetamide, an N,N-dipropylacetamide, an N-butylacetamide, an N,N-dibutylacetamide, N-phenylacetamide, N,N-diphenylacetamide, an N-(methylphenyl)acetamide, N,N-(dimethylphenyl)acetamide, propionamide, N-methylpropionamide, N,N-dimethylpropionamide, N-ethylpropionamide, N,N-diethylpropionamide, N-phenylpropionamide, N,N-diphenylpropionamide, a butyramide, an N-methylbutyramide, N,N-dimethylbutyramide, N-ethylbutyramide, N,N-diethylbutyramide, N-phenylbutyramide, N,N-diphenylbutyramide, benzamide, N-methylbenzamide, N,N-dimethylbenzamide, N-ethylbenzamide, N,N-diethylbenzamide, N-phenylbenzamide, N,N-diphenylbenzamide, a methylbenzamide, an N-methyl-methylbenzamide, N,N-dimethyl-methylbenzamide, N-ethyl-methylbenzamide N,N-diethyl-methylbenzamide, N-phenyl-methylbenzamide N,N-diphenyl-methylbenzamide or any combination thereof; alternatively, N-methylformamide, N,N-dimethylformamide, N-methylacetamide, N,N-dimethylacetamide, N-ethylacetamide, N,N-diethylacetamide, N-phenylacetamide, N,N-diphenylacetamide, N-methylpropionamide, N,N-dimethylpropionamide, N-methylbenzamide, N,N-dimethylbenzamide, or any combination thereof; alternatively, N-methylformamide; alternatively, N,N-dimethylformamide; alternatively, N-methylacetamide; alternatively, N,N-dimethylacetamide; alternatively, N-ethylacetamide; alternatively, N,N-diethylacetamide; alternatively, N-phenylacetamide; alternatively, N,N-diphenylacetamide; alternatively, N-methylpropionamide; alternatively, N,N-dimethylpropionamide; alternatively, N-methylbenzamide; or alternatively, N,N-dimethylbenzamide.

The alcohol which can be utilized as the neutral non-ionic organic modifier can be a $C_2$ to $C_{20}$, $C_2$ to $C_{15}$, or $C_2$ to $C_{10}$ alcohol. The nitrile can have the structure $R^{23}CH_2H$. $R^{23}$ of the alcohol nitrile can be a $C_1$ to $C_{15}$, $C_1$ to $C_{10}$, or $C_1$ to $C_5$ hydrocarbyl group, a $C_1$ to $C_{15}$, $C_1$ to $C_{10}$, or $C_1$ to $C_5$ alkyl group, a $C_5$ to $C_{15}$ or $C_5$ to $C_{10}$ cycloalkyl group, a $C_6$ to $C_{15}$ or $C_6$ to $C_{10}$ aryl group, or a $C_7$ to $C_{15}$ or $C_7$ to $C_{10}$ aralkyl group. In a non-limiting aspect, the alcohol which can be utilized as the neutral non-ionic organic modifier can comprise, consist essentially of, or can be, methanol, ethanol, a propanol, a butanol, a pentanol, a hexanol, a heptanol, an octanol, a nonanol, an decanol, phenol, a methylphenol, a dimethylphenol, an ethylphenol, a propylphenol, a dibutylphenol, or any combination thereof; alternatively, methanol, ethanol, a propanol, a butanol, a pentanol, or any combination thereof; alternatively, a methylphenol, a dimethylphenol, an ethylphenol, a propylphenol, a dibutylphenol, or any combination thereof; alternatively, methanol; alternatively, ethanol; alternatively, a propanol; alternatively, a butanol; alternatively, a pentanol; alternatively, methylphenol; alternatively, a dimethylphenol; alternatively, an ethylphenol; alternatively, a propylphenol; or alternatively, a dibutylphenol.

Generally, when a neutral non-ionic organic modifier is utilized, the neutral non-ionic organic modifier can be utilized in relation to the zirconium compound and/or the hydrocarbylmetal (or hydrocarbylaluminum) compound. The neutral non-ionic organic modifier to zirconium of the zirconium compound molar ratio (also referred to herein as modifier:Zr molar ratio) and/or neutral non-ionic organic modifier to hydrocarbylmetal (or hydrocarbylaluminum) compound molar ratio (also referred to herein as modifier:M (or modifier:Al) molar ratio), can be any ratio, which can form an oligomer product when the catalyst system is contacted with ethylene. When the neutral non-ionic organic modifier is utilized in relation to the zirconium of the zirconium compound, the minimum modifier:Zr molar ratio can be 0.1:1, 0.5:1, 0.75:1 0.8:1, 0.9:1, or 1:1; additionally or alternatively, the maximum modifier:Zr molar ratio can be 20:1, 15:1, 10:1 7.5:1, or 5:1. Generally, the modifier:Zr molar ratio can range from any minimum modifier:Zr molar ratio described herein to any maximum modifier:Zr molar ratio described herein. Accordingly, suitable non-limiting modifier:Zr molar ratios can be in a range from 0.5:120:1, 0.5:1 to 15:1, 0.75: 10:1, 1:1 to 15:1, 1:1 to 10:1, 1:1 to 5:1, 0.5:1 to 5:1, 0.75:1 to 3:1, 0.8:1 to 2:1, 0.9:1 or 1.25. Other appropriate modifier:Zr molar ratio ranges are readily apparent from this disclosure. When the neutral non-ionic organic modifier is utilized in relation to the hydrocarbylmetal (or hydrocarbylaluminum) compound, the minimum modifier:M (or modifier:Al) molar ratio can be 0.05:1, 0.1:1, 0.5:1, 0.75:1 0.8:1, 0.9:1, or 1:1; additionally or alternatively, the maximum modifier:Zr molar ratio can be 5:1, 3:1, 2:1, 1.5:1, 1:1, 0.75:1, or 0.5:1. Generally, the minimum modifier:M (or modifier:Al) molar ratio can range from any minimum modifier:M (or modifier:Al) molar ratio described herein to any maximum minimum modifier:M (or modifier:Al) molar ratio described herein. Accordingly, suitable non-limiting minimum modifier:M (or modifier:Al) molar ratio can be in a range from 0.5:1 to 5:1, 0.5:1 to 3:1, 0.75:1 to 2:1, or 0.75:1 to 1.5:1. Other appropriate modifier:M (or modifier:Al) molar ratio ranges are readily apparent from this disclosure.

In an aspect, the catalyst system can be prepared and then either i) contacted with ethylene, the chain transfer agent, and optional organic reaction medium or ii) introduced into the reaction zone. For example, in an aspect the process can comprise contacting the zirconium compound and the hydrocarbylmetal (or hydrocarbyl aluminum) compound to form the catalyst system which is then i) contacted with the ethylene, the chain transfer agent, and optional organic reaction medium, or ii) introduced into the reaction zone. When a neutral non-ionic organic modifier is utilized in the catalyst system, the neutral non-ionic organic modifier can be contacted with the zirconium compound prior to contacting the hydrocarbylmetal (or hydrocarbylaluminum) compound, can be contacted with the hydrocarbylmetal (or hydrocarbylaluminum) compound prior to contacting the zirconium compound, or can be contacted with a mixture of the zirconium compound and the hydrocarbylmetal (or hydrocarbylaluminum) compound. In another aspect, the neutral non-ionic organic modifier, the zirconium compound, and the hydrocarbylmetal (or hydrocarbylaluminum) compound can be simultaneously contacted to form the catalyst system.

In an alternative aspect, the catalyst system can be prepared in-situ where two or more components of the catalyst system are either i) separately (and/or simultaneously) contacted with ethylene, the chain transfer agent, and optional organic reaction medium or ii) separately (and/or simultaneously) introduced into the reaction zone. For example, in an aspect the process can comprise i) separately (and/or simultaneously) contacting the zirconium compound and the hydrocarbyl compound with the ethylene, the chain transfer agent, and optional organic reaction medium, or ii) separately (and/or simultaneously) introducing the zirconium compound and the hydrocarbyl compound into the reaction zone. In an aspect when a neutral non-ionic organic modifier is utilized in the catalyst system, the neutral non-ionic organic modifier can be contacted with the zirconium compound (to form a zirconium compound/neutral non-ionic organic modifier mixture) prior to separately (and/or simultaneously) contacting the zirconium compound (or the zirconium compound/neutral non-ionic organic modifier mixture) and the hydrocarbylmetal (or hydrocarbylaluminum) compound with ethylene, the chain transfer agent, and optional organic reaction medium or separately (and/or simultaneously) introducing the zirconium compound (or the zirconium compound/neutral non-ionic organic modifier mixture) and the hydrocarbylmetal (or hydrocarbylaluminum) compound into the reaction zone. In another aspect when a neutral non-ionic organic modifier is utilized in the catalyst system, the neutral non-ionic organic modifier can be contacted with the hydrocarbylmetal (or hydrocarbylaluminum) compound (to form a hydrocarbylmetal (or hydrocarbylaluminum) compound/neutral non-ionic organic modifier mixture) prior to separately (and/or simultaneously) contacting the hydrocarbylmetal (or hydrocarbylaluminum) compound or the hydrocarbylmetal (or hydrocarbylaluminum) compound/neutral non-ionic organic modifier mixture) and the zirconium compound with ethylene, the chain transfer agent, and optional organic reaction medium or separately (and/or simultaneously) introducing the hydrocarbylmetal (or hydrocarbylaluminum) compound (or hydrocarbylmetal (or hydrocarbylaluminum) compound/neutral non-ionic organic modifier mixture) and the zirconium compound into the reaction zone. In a further aspect when a neutral non-ionic organic modifier is utilized in the catalyst system, the neutral non-ionic organic modifier, the zirconium compound, and the hydrocarbylmetal (or hydrocarbylaluminum) compound can be separately (and/or simultaneously) contacted with ethylene, the chain transfer agent, and optional organic reaction medium or separately (and/or simultaneously) introduced into the reaction zone.

In one non-limiting aspect, the catalyst system can comprise a zirconium compound having the formula $ZrX^1_m$ and a hydrocarbylmetal compound comprise a hydrocarbylmetal compound having the formula $AlX^2_n R^1_{3-n}$, $Al_2X^2_3R^1_3$, $R^1_2Zn$) or any combination thereof. $X^1$, $X^2$, $R^1$, m, and n are independently described herein and these independent descriptions can be utilized without limitation and in any combination to further describe the catalyst system that can comprise a zirconium compound having the formula $ZrX^1_m$ and a hydrocarbylmetal compound comprising an alkylaluminum compound having the formula $AlX^2_n R^1_{3-n}$, $Al_2X^2_3R^1$, a dialkyl zinc compound ($R^1_2Zn$). In an aspect, each $X^1$ of $ZrX^1_m$ independently can be chloride or bromide and m is 4. In an aspect, the zirconium compound having the formula $ZrX^1_m$ can comprise, consist essentially of, or can be, $ZrCl_4$, $ZrBr_4$, $ZrClBr_3$, $ZrCl_2Br_2$ and $ZrCl_3Br$; alternatively, $ZrCl_4$ or $ZrBr_4$; or alternatively, $ZrClBr_3$; or alternatively, $ZrCl_4$. In an aspect, the hydrocarbylmetal compound can comprise an hydrocarbylmetal compound having the formula $AlX^2_2R^1$, $AlX^2R^1_2$, $AlR^1_3$, $Al^2X^2_3R^1_3$, $R^1_2Zn$, or any combination thereof; alternatively, $AlX^2_2R^1$, $AlX^2R^1_2$, $AlR^1_3$, $Al_2X^2_3R^1_3$, or any combination thereof. $X^2$ and $R^1$ are independently described herein and these independent descriptions can be utilized without limitation and in any combination to further describe the catalyst system that can comprise a zirconium compound having the formula $ZrX^1_m$ and a hydrocarbylmetal compound comprising an alkylaluminum compound having the formula $AlX^2_n R^1_{3-n}$, $Al_2X^2_3R^1_3$, $R^1_2Zn$ or any combination thereof. In an aspect, each $X^2$ of the hydrocarbylmetal compound independently can be a halide and each $R^1$ independently can be a $C_2$ to $C_4$ alkyl group. In some aspects, the alkylmetal compound can comprise, or consist essentially of, triethylaluminum, diethylaluminum chloride, ethylaluminum dichloride, ethylaluminum sesquichloride, diethylzinc, or any combination thereof, alternatively, triethylaluminum and diethylaluminum chloride; alternatively, triethylaluminum and ethylaluminum dichloride; alternatively, triethylaluminum and ethylaluminum sesquichloride; alternatively, diethylaluminum chloride and ethylaluminum dichloride; alternatively, ethylaluminum sesquichloride. Non-limiting values for the metal of the hydrocarbylmetal (or aluminum of the hydrocarbylaluminum) compound to zirconium of the zirconium compound molar ratio can be in a range of from 1:1 to 50:1, 1:1 to 15:1, or 10:1 to 25:1. In some non-limiting aspects, the catalyst system (or catalyst system components) can further comprise a neutral non-ionic organic modifier comprising $C_2$ to $C_{20}$ ester (any described herein) where the neutral non-ionic organic modifier to zirconium of the zirconium compound molar ratio can be in any range disclosed herein (e.g., in a range of 0.5:1 to 5:1). In other non-limiting aspects, the catalyst system (or catalyst system components) can further comprise a neutral non-ionic organic modifier comprising a $C_2$ to $C_{20}$ ether, $C_2$ to $C_{20}$ sulfide, a $C_1$ to $C_{20}$ amine, a $C_3$ to $C_{20}$ phosphine, or any combination thereof (alternatively, a $C_2$ to $C_{20}$ ether, $C_2$ to $C_{20}$ sulfide, or any combination thereof, alternatively, a $C_2$ to $C_{20}$ ether; alternatively, a $C_2$ to $C_{20}$ sulfide; alternatively, a $C_1$ to $C_{20}$ amine; or alternatively, a $C_3$ to $C_{20}$ phosphine) wherein the neutral non-ionic organic modifier to zirconium of the zirconium compound molar ratio can be any range disclosed herein (e.g., in a range of from 0.5:1 to 20:1)

In another non-limiting aspect, the zirconium compound can have the formula $ZrX^1_m Y^1_q$ and the hydrocarbylmetal compound can comprise a hydrocarbylmetal compound having the formula $AlX^2_n R^1_{3-n}$ $Al_2X^2_3R^1_3$, or any combination thereof. $X^1$, $Y^1$, $X^2$, $R^1$, n, and q are independently described herein and these independent descriptions can be utilized without limitation and in any combination to further describe the catalyst system that can comprise a zirconium compound having the formula $ZrX^1_m Y^1_q$ and a hydrocarbylmetal compound comprising an alkylaluminum compound having the formula $AlX^2_n R_{3-n}$, $Al_2X^2_3R^1_3$, or any combination thereof. Each $X^1$ of $ZrX^1_m Y^1_q$ independently can be chloride or bromide; alternatively, chloride. Each $Y^1$ of $ZrX^1_m Y^1_q$ independently can be a $C_1$ to $C_{10}$ hydrocarboxide (e.g., any described herein), a $C_1$ to $C_{10}$ hydrocarbylcarboxylate (e.g., any described herein), or a $C_1$ to $C_{15}$ hydrocarbylsulfonate (e.g., any described herein); alternatively, a $C_1$ to $C_{10}$ hydrocarboxide (e.g., any described herein); alternatively, a $C_1$ to $C_{10}$ hydrocarbylcarboxylate (e.g., any described herein); or alternatively, a $C_1$ to $C_{15}$ hydrocarbylsulfonate (e.g., any described herein). For $ZrX^1_m Y^1_q$, m can be in a range from 0 to 4, q can be in a range from 0 to 4, and m+q can be 4; alternatively, m can be 4 and q can be 0; or alternatively, m can be 0 and q can be 4. In an aspect the zirconium compound having the formula $ZrX^1_m Y^1_q$ can comprise, can consist essentially of, or can be, a zirconium tetra $C_1$ to $C_{10}$ hydrocarbylcarboxylate; alternatively, a zirconium tetra $C_1$ to $C_5$ hydrocarbylcarboxylate; or alternatively, $Zr(O_2C_3H_7)_4$. In another aspect, the zirconium compound having the formula $ZrX^1_m$ can comprise, consist essentially of, or can be, $ZrCl_4$, $ZrBr_4$, $ZrClBr_3$, $ZrCl_2Br_2$ and $ZrCl_3Br$; alternatively, $ZrCl_4$ or $ZrBr_4$; or alternatively, $ZrClBr_3$; or alternatively $ZrCl_4$. In an aspect, hydrocarbylmetal compound can comprise an hydrocarbylmetal compound having the formula $AlX^2_2R^1$, $AlX^2R^1_2$, $AlR^1_3$, $Al_2X^2_3R^1_3$, or any combination thereof; alternatively, $AlX^2_2R$, $AlX^2R^1_2$, $AlR^1_3$, $Al_2X^2_3R^1_3$, or any combination thereof. $X^2$ and $R^1$ are independently described herein and these independent descriptions can be utilized without limitation and in any combination to further describe the catalyst system that can comprise a zirconium compound having the formula $ZrX^1_m$ and a hydrocarbylmetal compound comprising an alkylaluminum compound having the formula $AlX^2_nR^1_{3-n}$, $Al_2X^2_3R^1_3$, $R^1_2Zn$, or any combination thereof. In an aspect, each $X^2$ of the hydrocarbylmetal compound independently can be a halide and each $R^1$ independently can be a $C_2$ to $C_4$ alkyl group. In some aspects, the alkylmetal compound can comprise, or consist essentially of, triethylaluminum, diethylaluminum chloride, ethylaluminum dichloride, ethylaluminum sesquichloride, or any combination thereof; alternatively, triethylaluminum and diethylaluminum chloride; alternatively, triethylaluminum and ethylaluminum dichloride; alternatively, triethylaluminum and ethylaluminum sesquichloride; alternatively, diethylaluminum chloride and ethylaluminum dichloride; alternatively, ethylaluminum sesquichloride. Non-limiting values for the metal of the hydrocarbylmetal (or aluminum of the hydrocarbylaluminum) compound to zirconium of the zirconium compound molar ratio can be in a range of from 1:1 to 50:1, 2:1 to 25:1, or 1:1 to 15:1, among others disclosed herein. In an aspect, the zirconium compound having the formula $ZrX^1_mY^1_q$ can be at partially hydrolyzed by contacting $ZrX^1_mY^1_q$ with water at a water to zirconium molar ratio of 0.01:1 to 3:1, 0.1: to 2:1, or 0.25:I to 1.75:1. In an aspect, the catalyst system (or catalyst system components) can further comprise a neutral non-ionic organic modifier comprising a $C_2$ to $C_{15}$ alcohol, $C_1$ to $C_{15}$ amine, $C_2$ to $C_{15}$ amide, or any combination thereof; alternatively, $C_2$ to $C_{15}$ alcohol; alternatively, $C_1$ to $C_{15}$ amine; or alternatively, $C_2$ to $C_{15}$ amide. In an aspect, the neutral non-ionic organic modifier to metal of the hydrocarbylmetal (or aluminum of the hydrocarbylaluminum) compound molar ratio is in a range of 0.75:1 to 2:1, or 0.75:1 to 1.5:1, among others disclosed herein. In an aspect, neutral non-ionic organic modifier can be contacted with the hydrocarbylmetal (or hydrocarbylaluminum) compound prior to the hydrocarbylmetal (or hydrocarbylaluminum) compound contacting the zirconium compound and/or ethylene (and/or being introduced into the reaction zone). In some aspects, the neutral non-ionic organic modifier is contacted with the zirconium compound prior to the zirconium compound contacting ethylene and/or the hydrocarbylmetal compound (and/or being introduced into the reaction zone).

The process described herein can utilize 1) a chain transfer agent comprising a compound having a hydrogen silicon bond, a compound having a hydrogen sulfur bond, a compound having a hydrogen phosphorus bond, or any combination thereof, 2) hydrogen, 3) a transition metal compound chain transfer agent, or any combination thereof; alternatively, 1) a chain transfer agent comprising a compound having a hydrogen silicon bond, a compound having a hydrogen sulfur bond, a compound having a hydrogen phosphorus bond, and 2) hydrogen; alternatively, a chain transfer agent comprising a compound having a hydrogen silicon bond, a compound having a hydrogen sulfur bond, a compound having a hydrogen phosphorus bond, or any combination thereof; alternatively, hydrogen; or alternatively, a transition metal compound chain transfer agent. Generally, the chain transfer agent, hydrogen, and/or the transition metal compound chain transfer agent are utilized to achieve a desirable effect in the process of forming an oligomer product. The desirable effect can include the production of (a) less than 1 wt. % of polymer, (b) less than 1 wt. % compounds having a weight average molecular weight of greater than 1000 g/mol, or (c) any combination thereof wherein the wt. % is based on the total weight of the oligomer product; alternatively or additionally, producing an oligomer product (a) comprising a polymer having a lower Mw, (b) an oligomer product where the polymer has a lower Mw maximum peak, (c) an oligomer product having a reduced quantity of polymer, (d) an oligomer product having a reduced % of polymer having a molecular weight greater than 100,000 molecular weight, or (e) any combination thereof relative to the same process not using a 1) a chain transfer agent comprising a compound having a hydrogen silicon bond, a compound having a hydrogen sulfur bond, a compound having a hydrogen phosphorus bond, or any combination thereof, 2) hydrogen, and/or 3) a transition metal compound chain transfer agent.

The chain transfer agent can comprise, consist essentially of, or can be, a compound having a hydrogen silicon bond, a compound having a hydrogen sulfur bond, a compound having a hydrogen phosphorus bond, or any combination thereof; alternatively, a compound having a hydrogen silicon bond; alternatively, a compound having a hydrogen sulfur bond; or alternatively, a compound having a hydrogen phosphorus bond. The reaction zone can have any chain transfer agent to ethylene mole ratio which can provide any desired effect described herein. In an aspect, the reaction zone can have a minimum chain transfer agent to ethylene mole ratio of $1\times10^{-5}$:1, $5\times10^{-4}$:1, $1\times10^{-4}$:1, or $5\times10^{-3}$:1; additionally or alternatively, a maximum chain transfer agent to ethylene mole ratio of $5\times10^{-1}$:1, $1\times10^{-1}$:1, $5\times10^{-2}$:1, or $1\times10^{-2}$:1. Generally, the reaction zone can have chain transfer agent to ethylene mole ratio that can range from any minimum chain transfer agent to ethylene mole ratio described herein to any maximum chain transfer agent to ethylene mole ratio described herein. Accordingly, suitable reaction zone chain transfer agent to ethylene mole ratios can be in a range from $1\times10^{-5}$:1 to $5\times10^{-1}$:1, $5\times10^{-4}$:1 to $1\times10^{-1}$:1, $1\times10^{-4}$:1 to $5\times10^{-2}$:1, or $5\times10^{-3}$:1 to $1\times10^{-2}$:1. Other appropriate reaction zone chain transfer agent to ethylene mole ratio ranges are readily apparent from this disclosure.

The compound having a hydrogen silicon bond which can be utilized as the neutral non-ionic organic modifier can be a $C_1$ to $C_{40}$, $C_1$ to $C_{30}$, or $C_1$ to $C_{20}$ compound having a hydrogen silicon bond. In an aspect, the compound having a hydrogen silicon bond which can be utilized as a chain transfer agent can have the formula $R^{31}SiH_3$, $(R^{31})_2SiH_2$, $(R^{31})_3SiH$, $R^{31}OSiH3$, $(R^{31}O)_2SiH_2$, $(R^{31}O)_3SiH$, or any combination thereof, alternatively, $R^{31}SiH_3$, $(R^{31})_2SiH_2$, $(R^{31})_3SiH$, or any combination thereof, alternatively, $R^{31}OSiH3$, $(R^{31}O)_2SiH_2$, $(R^{31}O)_3SiH$, or any combination thereof, alternatively, $R^{31}SiH_3$; alternatively, $(R^{31})_2SiH_2$; alternatively, $(R^{31})_3SiH$; alternatively, $R^{31}OSiH3$; alternatively, $(R^{31}O)_2SiH_2$; or alternatively, $(R^{31}O)_3SiH$. Each $R^{31}$ of the formulas od the compounds having a hydrogen silicon bond independently can be a $C_1$ to $C_{15}$, $C_1$ to $C_{10}$, or $C_1$ to $C_5$ hydrocarbyl group, a $C_1$ to $C_{15}$, $C_1$ to $C_{10}$, or $C_1$ to $C_5$ alkyl group, a $C_5$ to $C_{15}$ or $C_5$ to $C_{10}$ cycloalkyl group, a $C_6$ to $C_{15}$ or $C_6$ to $C_{10}$ aryl group, or a $C_7$ to $C_{15}$ or $C_7$ to $C_{10}$ aralkyl group. In a non-limiting aspect, the compound having a hydrogen silicon bond (e.g., having any formula described herein) can comprise, consist essentially of, or can be, trimethylsilane, diethylsilane, triethylsilane, a tripropylsilane, a dibutylsilane, a tributylsilane, a hexylsilane, a dihexylsilane a trihexylsilane, an octylsilane, a dioctylsilane, a trioctylsilane, a decylsilane, a didecylsilane, a tridecylsilane, a tridodecylsilane, phenylsilane, diphenylsilane, triphenylsilane, phenethylsilane, diphenethylsilane, triphenethylsilane, trimethoxysilane, triethoxysilane, 9,10-dimethyl-9,10-dihydro-9,10-disilaanthracene, tetraphenyldisilane, or any combination thereof; alternatively, trimethylsilane, diethylsilane, triethylsilane, a tripropylsilane, a dibutylsilane, a tributylsilane, a hexylsilane, a dihexylsilane, a trihexylsilane, an octylsilane, a dioctylsilane, a trioctylsilane, a decylsilane, a didecylsilane, a tridecylsilane, a tridodecylsilane, phenylsilane, diphenylsilane, triphenylsilane, phenethylsilane, diphenethylsilane, triphenethylsilane, or any combination thereof, trimethylsilane, diethylsilane, triethylsilane, a tripropylsilane, a dibutylsilane, a tributylsilane, a hexylsilane, a dihexylsilane, a trihexylsilane, an octylsilane, a dioctylsilane, a decylsilane, a didecylsilane, phenylsilane, diphenylsilane, triphenylsilane, phenethylsilane, diphenethylsilane, or any combination thereof, alternatively, a trioctylsilane, a tridecylsilane, a tridodecylsilane, triphenethylsilane, or any combination thereof, alternatively, trimethoxysilane, triethoxysilane, or any combination thereof; or alternatively, phenylsilane, diphenylsilane, or any combination thereof.

The compound having a hydrogen sulfur bond which can be utilized as the neutral non-ionic organic modifier can be a $C_1$ to $C_{20}$, $C_1$ to $C_{15}$, or $C_1$ to $C_{10}$ compound having a hydrogen sulfur bond. The compound having a hydrogen sulfur bond which can be utilized as the neutral non-ionic organic modifier can comprise, consist essentially of, or can be, a $C_1$ to $C_{20}$, $C_1$ to $C_{15}$, or $C_1$ to $C_{10}$ thiol, $C_1$ to $C_{20}$, $C_1$ to $C_{15}$, or $C_1$ to $C_{10}$ thioglycolate, and/or a $C_1$ to $C_{20}$, $C_1$ to $C_{15}$, or $C_1$ to $C_{10}$ mercaptopropionate; alternatively, $C_1$ to $C_{20}$, $C_1$ to $C_{15}$, or $C_1$ to $C_{10}$ thiol; alternatively, $C_1$ to $C_{20}$, $C_1$ to $C_{15}$, or $C_1$ to $C_{10}$ thioglycolate; or alternatively, a $C_1$ to $C_{20}$, $C_1$ to $C_{15}$, or $C_1$ to $C_{10}$ mercaptopropionate. In an aspect, the compound having a hydrogen sulfur bond which can be utilized as a chain transfer agent can have the formula $R^{32}SH$, $R^{32}CO_2CH_2SH$, $R^{32}CO_2CH_2CH_2SH$, or any combination thereof, alternatively, $R^{32}CO_2CH_2SH$, $R^{32}CO_2CH_2CH_2SH$, or any combination thereof, alternatively, $R^{32}SH$; alternatively, $R^{32}CO_2CH_2SH$; or alternatively, $R^{32}CO_2CH_2CH_2SH$. $R^{32}$ of the formulas of compounds having a hydrogen sulfur bond can be a $C_1$ to $C_{15}$, $C_1$ to $C_{10}$, or $C_1$ to $C_5$ hydrocarbyl group, a $C_1$ to $C_{15}$, $C_1$ to $C_{10}$, or $C_1$ to $C_5$ alkyl group, a $C_5$ to $C_{15}$ or $C_5$ to $C_{10}$ cycloalkyl group, a $C_6$ to $C_{15}$ or $C_6$ to $C_{10}$ aryl group, or a $C_7$ to $C_{15}$ or $C_7$ to $C_{10}$ aralkyl group. In a non-limiting aspect, the compound having a hydrogen sulfur bond (e.g., having any formula described herein) can comprise, consist essentially of, or can be, methanethiol, ethanethiol, a propanethiol, a butanethiol, a pentanethiol, a hexanethiol, a heptanethiol, an octanethiol, a nonanethiol, a decanethiol, a undecanethiol, a dodecanethiol, methyl thioglycolate, ethyl thioglycolate, a methyl mercaptopropionate, an ethyl mercaptopropionate, or any combination thereof, alternatively, methanethiol, ethanethiol, a propanethiol, a butanethiol, a pentanethiol, a hexanethiol, a heptanethiol, an octanethiol, a nonanethiol, a decanethiol, a undecanethiol, a dodecanethiol, or any combination thereof, alternatively, methanethiol, ethanethiol, a propanethiol, a butanethiol, a pentanethiol or any combination thereof, alternatively, a hexanethiol, a heptanethiol, an octanethiol, a nonanethiol, a decanethiol, a undecanethiol, a dodecanethiol, or any combination thereof, alternatively, methyl thioglycolate, ethyl thioglycolate, a methyl mercaptopropionate, an ethyl mercaptopropionate, or any combination thereof, alternatively, ethanethiol; alternatively, a propanethiol; alternatively, a butanethiol; alternatively, tert-butylthiol; alternatively, octanethiol; alternatively, a decanethiol; alternatively, a dodecanethiol; alternatively, methyl thioglycolate; or alternatively, a methyl mercaptopropionate.

The compound having a hydrogen phosphorus bond which can be utilized as the neutral non-ionic organic modifier can be a $C_1$ to $C_{40}$, $C_1$ to $C_{30}$, or $C_1$ to $C_{20}$ compound having a hydrogen phosphorus bond. The compound having a hydrogen phosphorus bond which can be utilized as the neutral non-ionic organic modifier can comprise, consist essentially of, or can be, a $C_1$ to $C_{40}$, $C_1$ to $C_{30}$, or $C_1$ to $C_{20}$ phosphine and/or $C_1$ to $C_{40}$, $C_1$ to $C_{30}$, or $C_1$ to $C_{20}$ phosphite; alternatively, a $C_1$ to $C_{40}$, $C_1$ to $C_{30}$, or $C_1$ to $C_{20}$ phosphine; or alternatively a $C_1$ to $C_{40}$, $C_1$ to $C_{30}$, or $C_1$ to $C_{20}$ phosphite. In an aspect, the compound having a hydrogen phosphorus bond which can be utilized as a chain transfer can have the formula $(R^{33})_2PH$, $(R^{33}O)_2P(=O)H$, or any combination thereof; alternatively, $R^{33}PH_2$; or alternatively, $(R^{33}O)_2P(=O)H$. Each $R^{33}$ of the formulas of the compounds having a hydrogen phosphorus bond independently can be a $C_1$ to $C_{15}$, $C_1$ to $C_{10}$, or $C_1$ to $C_5$ hydrocarbyl group, a $C_1$ to $C_{15}$, $C_1$ to $C_{10}$, or $C_1$ to $C_5$ alkyl group, a $C_5$ to $C_{15}$ or $C_5$ to $C_{10}$ cycloalkyl group, a $C_6$ to $C_{15}$ or $C_6$ to $C_{10}$ aryl group, or a $C_7$ to $C_{15}$ or $C_7$ to $C_{10}$ aralkyl group. In a non-limiting aspect, the compound having a phosphorus hydrogen bond (e.g., having any formula described herein) can comprise, consist essentially of, or can be, dimethylphosphine, diethylphosphine, a dipropylphosphine, a dibutylphosphine, a dihexylphosphine, a dioctylphosphine, dicyclopenylphosphine, dicyclohexylphosphine, phenylphosphine, diphenyl phosphine, dimethylphosphite, diethylphosphite, a dibutylphosphite, a dihexylphosphite, a dioctylphosphite, diphenylphosphite, dibenzylphosphite, or any combination thereof; dimethylphosphine, diethylphosphine, a dibutylphosphine, a dioctylphosphine dicyclopenylphosphine, dicyclohexylphosphine, phenylphosphine, diphenyl phosphine, dimethylphosphite, diethylphosphite, diplienylphosphite, dibenzylphosphite, or any combination thereof; alternatively, dimethylphosphine, diethylphosphine, a dibutylphosphine, dicyclopenylphosphine, dicyclohexylphosphine, a dioctylphosphine, phenylphosphine, diphenyl phosphine, or any combination thereof; or alternatively, dimethylphosphite, diethylphosphite, diphenylphosphite, dibenzylphosphite, or any combination thereof.

The transition metal compound chain transfer agent can comprise, consist essentially of, or can be, a group 8 transition metal compound, a group 9 transition meal compound, a group 10 transition metal compound, or any combination thereof; alternatively, a group 8 transition metal compound; alternatively, a group 9 transition meal compound; or alternatively, a group 10 transition metal compound. In an aspect, the reaction zone can have a minimum as transition metal to ethylene mole ratio of $1 \times 10^{-9}:1$, $5 \times 10^{-8}:1$, $1 \times 10^{-8}:1$, $5 \times 10^{-7}:1$, or $1 \times 10^{-7}:1$; additionally or alternatively, a maximum as transition metal to ethylene mole ratio of $5 \times 10^{-3}:1$, $1 \times 10^{-3}:1$, $5 \times 10^{-4}:1$, $1 \times 10^{-4}:1$, or $5 \times 10^{-5}:1$. Generally, the reaction zone can have as transition metal to ethylene mole ratio that can range from any minimum as transition metal to ethylene mole ratio described herein to any maximum as transition metal to ethylene mole ratio described herein. Accordingly, suitable reaction zone as transition metal to ethylene mole ratios can be in a range from $1 \times 10^{-9}:1$ to $5 \times 10^{-3}:1$, $5 \times 10^{-8}:1$ to $1 \times 10^{-3}:1$, $1 \times 10^{-8}:1$ to $5 \times 10^{-4}:1$, $5 \times 10^{-7}:1$ to $1 \times 10^{-4}:1$, or $1 \times 10^{-7}:1$ to $5 \times 10^{-5}:1$. Other appropriate reaction zone as transition metal to ethylene mole ratio ranges are readily apparent from this disclosure.

Generally, the transition metal compound chain transfer agent can have the formula $MX^4_p$ where M is the transition metal, $X^4$ is a mono anion, and p is the oxidation state of the transition metal M. The transition metal M can be group 8-10 transition metal; alternatively, a group 8-9 transition metal; alternatively, a group 8 transition metal; alternatively, a group 9 transition metal; or alternatively, a group 10 transition metal. In an aspect, the transition metal M can be iron, cobalt, or nickel; alternatively, iron or cobalt; alternatively, iron; alternatively, cobalt; or alternatively, nickel. Generally, p of the transition metal compound chain transfer agent having the formula $MX^4_p$ is an integer from 2 to 4, is 2 or 3, 2, 3, or 4. In an aspect, each p of the transition metal compound chain transfer agent having the formula $MX^4_p$ independently can be a halide, a carboxylate, a beta-dionate, an hydrocarboxide, or a nitrate; alternatively, a carboxylate, a beta-dionate, or an hydrocarboxide; alternatively, a carboxylate or a beta-dionate; alternatively, a carboxylate; or alternatively, a beta-dionate. In an aspect, each carboxylate group of the transition metal compound chain transfer agent having the formula $MX^4_p$ independently can be a $C_2$ to $C_{24}$, a $C_4$ to $C_{19}$, or a $C_5$ to $C_{12}$ carboxylate. In an aspect, each hydrocarboxide of the transition metal compound chain transfer agent having the formula $MX^4_p$ independently can be a $C_1$ to $C_{24}$, a $C_4$ to $C_{19}$, or a $C_5$ to $C_{12}$ hydrocarboxide. In an aspect, each beta-dionate group of the transition metal compound chain transfer agent having the formula $MX^4_p$ independently can be a $C_5$ to $C_{24}$, a $C_5$ to $C_{19}$, or a $C_5$ to $C_{12}$ beta-dionate.

Generally, each halide of the transition metal compound chain transfer agent having the formula $MX^4_p$ independently can be chlorine, bromine, or iodine; alternatively, bromine; or alternatively, iodine. Generally, each carboxylate of the transition metal compound chain transfer agent having the formula $MX^4_p$ independently can be acetate, a propionate, a butyrate, a pentanoate, a hexanoate, a heptanoate, an octanoate, a nonanoate, a decanoate, an undecanoate, or a dodecanoate; alternatively, a pentanoate, a hexanoate, a heptanoate, an octanoate, a nonanoate, a decanoate, an undecanoate, or a dodecanoate; alternatively, a pentanoate, a hexanoate, a heptanoate, an octanoate, a nonanoate a decanoate, an undecanoate, or a dodecanoate; alternatively, a hexanoate; alternatively, a octanoate; alternatively, a decanoate; or alternatively a dodecanoate. Generally, each hydrocarboxide of the transition metal compound chain transfer agent having the formula $MX^4_p$ independently can be methoxide, ethoxide, a propoxide, a butoxide, a phenoxide, a methylphenoxide, or a dimethylphenoxide; alternatively, methoxide, ethoxide, a propoxide, or a butoxide; alternatively, a phenoxide, a methylphenoxide, or a dimethylphenoxide. Generally, each β-diketonate of the transition metal compound chain transfer agent having the formula $MX^4_p$ independently can be acetylacetonate (i.e., 2,4-pentanedionate), hexafluoroacetylacetonate (i.e., 1,1,1,5,5,5-hexafluoro-2,4-pentanedionate), or benzoylacetonate; alternatively, acetylacetonate; alternatively, hexafluoroacetylacetonate; or alternatively, benzoylacetonate. In some non-limiting aspects, transition metal compound chain transfer agent (or the transition metal compound chain transfer agent having the formula $MX^4_p$) can comprise, consist essentially of, or can be iron(II) chloride, iron(III) chloride, iron(II) acetate, iron(III) acetate, an iron(II) octanoate, an iron(III) octanoate, iron(II) acetylacetonate, iron(III) acetylacetonate, cobalt(II) chloride, cobalt(III) chloride, cobalt(II) acetate, cobalt(III) acetate, an cobalt(II) octanoate, a cobalt(III) octanoate, cobalt(II) acetylacetonate, cobalt(ITT) acetylacetonate, nickel(II) chloride, nickel(II) acetate, a nickel(II) octanoate, or nickel(II) acetylacetonate; alternatively, iron(II) acetate, iron(III) acetate, an iron(II) octanoate, an iron(III) octanoate, iron(II) acetylacetonate, iron(III) acetylacetonate, cobalt(II) acetate, cobalt (III) acetate, a cobalt(II) octanoate, a cobalt(III) octanoate, cobalt(II) acetylacetonate, cobalt(ITT) acetylacetonate, nickel(II) acetate, a nickel(II) octanoate, or nickel(II) acetylacetonate; alternatively, an iron(II) octanoate, an iron(III) octanoate, iron(II) acetylacetonate, iron(III) acetylacetonate, a cobalt(II) octanoate, a cobalt(III) octanoate, cobalt(II) acetylacetonate, cobalt(ITT) acetylacetonate, a nickel(II) octanoate, or nickel (II) acetylacetonate; alternatively, an iron(III) octanoate, iron(III) acetylacetonate, a cobalt(III) octanoate, cobalt(III) acetylacetonate, a nickel(II) octanoate, or nickel(II) acetylacetonate.

When hydrogen is utilized, the reaction zone can have any hydrogen to ethylene ratio which can provide any desired effect described herein. In an aspect, a minimum hydrogen to ethylene ratio can be (0.05 g hydrogen)/(kg ethylene), (0.1 g hydrogen)/(kg ethylene), (0.25 g hydrogen)/(kg ethylene), (0.4 g hydrogen)/(kg ethylene), or (0.5 g hydrogen)/(kg ethylene); additionally or alternatively, a maximum hydrogen to ethylene ratio can be (5 g hydrogen)/(kg ethylene), (3 g hydrogen)/(kg ethylene), (2.5 g hydrogen)/(kg ethylene), (2 g hydrogen)/(kg ethylene), or (1.5 g hydrogen)/(kg ethylene). Generally, the reaction zone can have hydrogen to ethylene ratio that can range from any minimum hydrogen to ethylene ratio described herein to any maximum hydrogen to ethylene ratio described herein. Accordingly, suitable reaction zone hydrogen to ethylene ratios can be in a range from (0.05 g hydrogen)/(kg ethylene) to (5 g hydrogen)/(kg ethylene), from (0.25 g hydrogen)/(kg ethylene) to (5 g hydrogen)/(kg ethylene), from (0.25 g hydrogen)/(kg ethylene) to (4 g hydrogen)/(kg ethylene), from (0.4 g hydrogen)/(kg ethylene) to (3 g hydrogen)/(kg ethylene), from (0.4 g hydrogen)/(kg ethylene) to (2.5 g hydrogen)/(kg ethylene), from (0.4 g hydrogen)/(kg ethylene) to (2 g hydrogen)/(kg ethylene), or from (0.5 g hydrogen)/(kg ethylene) to (2 g hydrogen)/(kg ethylene). Other appropriate reaction zone hydrogen to ethylene ratio ranges are readily apparent from this disclosure.

The organic reaction medium which can be utilized in the processes described herein can be a hydrocarbon, a halogenated hydrocarbon, or a combination thereof, for example. Hydrocarbons and halogenated hydrocarbons which can be used as the organic reaction medium can include aliphatic hydrocarbons, aromatic hydrocarbons, petroleum distillates, halogenated aliphatic hydrocarbons, halogenated aromatic hydrocarbons, or any combination thereof. Aliphatic hydrocarbons which can be useful as the organic reaction medium include $C_3$ to $C_{20}$ aliphatic hydrocarbons, or $C_4$ to $C_{15}$ aliphatic hydrocarbons, or $C_5$ to $C_{10}$ aliphatic hydrocarbons. The aliphatic hydrocarbons which can be used as the organic reaction medium can be cyclic or acyclic and/or can be linear or branched, unless otherwise specified. Non-limiting examples of suitable acyclic aliphatic hydrocarbon organic reaction mediums that can be utilized singly or in any combination include propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), and octane (n-octane or a mixture of linear and branched $C_5$ acyclic aliphatic hydrocarbons). Aromatic hydrocarbons which can be useful as the organic reaction medium include aromatic hydrocarbons, or $C_6$ to $C_{10}$ aromatic hydrocarbons. Non-limiting examples of suitable aromatic hydrocarbons that can be utilized singly or in any combination as the organic reaction medium include benzene, toluene, xylene (including ortho-xylene, meta-xylene, para-xylene, or mixtures thereof), and ethylbenzene. Halogenated aliphatic hydrocarbons which can be useful as the organic reaction medium include $C_1$ to $C_{15}$ halogenated aliphatic hydrocarbons, or $C_1$ to $C_{10}$ halogenated aliphatic hydrocarbons, or $C_1$ to $C_5$ halogenated aliphatic hydrocarbons. The halogenated aliphatic hydrocarbons which can be used as the organic reaction medium can be cyclic or acyclic and/or can be linear or branched, unless otherwise specified. Non-limiting examples of suitable halogenated aliphatic hydrocarbons which can be utilized as the organic reaction medium include methylene chloride, chloroform, carbon tetrachloride, dichloroethane, trichloroethane, or any combination thereof. Halogenated aromatic hydrocarbons which can be useful as the organic reaction medium include $C_6$ to $C_{20}$ halogenated aromatic hydrocarbons, or $C_6$ to $C_{10}$ halogenated aromatic hydrocarbons. Non-limiting examples of suitable halogenated aromatic hydrocarbons which can be used as the organic reaction medium include chlorobenzene, dichlorobenzene, or any combination thereof.

Generally, the oligomer product can be formed using any conditions capable of forming an oligomer product. Conditions which can be utilized to form the oligomer product can include, singly or in any combination, reaction zone pressure, reaction zone ethylene partial pressure, reaction zone temperature, reaction zone zirconium of the zirconium compound to ethylene molar ratio, reaction zone ethylene to organic reaction medium mass ratio, reaction zone residence time (or average residence time), ethylene conversion (or single pass ethylene conversions, oligomer product Schultz-Flory K value, and oligomer product selectivity to normal alpha olefins. Reaction zone pressure, reaction zone ethylene partial pressure, reaction zone temperature, reaction zone zirconium of the zirconium compound to ethylene molar ratio, reaction zone ethylene to organic reaction medium mass ratio, reaction zone residence time (or average residence time), ethylene conversion (or single pass ethylene conversions, oligomer product Schultz-Flory K value, oligomer product selectivity to normal alpha olefins are independently described herein and these independent descriptions of reaction zone pressure, reaction zone ethylene partial pressure, reaction zone temperature, reaction zone zirconium of the zirconium compound to ethylene molar ratio, reaction zone ethylene to organic reaction medium mass ratio, reaction zone residence time (or average residence time), ethylene conversion (or single pass ethylene conversions, oligomer product Schultz-Flory K value, and oligomer product selectivity to normal alpha olefins can be utilized without limitation and in any combination to further describe the processes disclosed herein.

The oligomer product can be formed at a reaction zone (or the reaction zone can have a) minimum pressure of 100 psi (689 kPa), 250 psi (1.72 MPa), 500 psi (3.45 MPa), 750 psi (5.17 MPa), 900 psi (6.21 MPa), or 1000 psi (6.89 MPa); alternatively or additionally, at a maximum pressure of 5000 psi (34.5 MPa), 4500 psi (31 MPa), 4,000 psi (27.6 MPa), 3500 psi (24.1 MPa), 3000 psi (20.7 MPa), 2,500 psi (17.2 MPa), 2,000 psi (13.8 MPa), 1,500 psi (10.3 MPa), 1250 psi (8.62 MPa), or 1000 psi (6.89 MPa). Generally, the oligomer product can be formed at a reaction zone (or the reaction zone can have a) a pressure ranging from any minimum pressure disclosed herein to any maximum pressure disclosed herein. In some non-limiting aspects, the oligomer product can be formed at a reaction zone (or the reaction zone can have a) pressure from 100 psi (689 kPa) to 5000 psi (34.5 MPa), 100 psi (689 kPa) to 2,500 psi (17.2 MPa), 100 psi (689 kPa) to 1000 psi (6.89 kPa), 500 psi (3.45 MPa) to 4500 psi (31 MPa), 500 psi (3.45 MPa) to 2,500 psi (17.2 MPa), 500 psi (3.45 MPa) to 1000 psi (6.89 MPa), 750 psi (5.17 MPa) to 4500 psi (31 MPa), 900 psi (6.21 MPa) to 4,000 psi (27.6 MPa), or 1000 psi (6.89 MPa) to 3500 psi (24.1 MPa). Other pressure ranges that can be utilized are readily apparent to those skilled in the art with the aid of this disclosure.

The oligomer product can be formed at a reaction zone (or the reaction zone can have a) minimum ethylene partial pressure of 100 psi (689 kPa), 250 psi (1.72 MPa), 500 psi (3.45 MPa), 750 psi (5.17 MPa), 900 psi (6.21 MPa), or 1000 psi (6.89 MPa); alternatively or additionally, at a maximum pressure of 5000 psi (34.5 MPa), 4500 psi (31 MPa), 4,000 psi (27.6 MPa), 3500 psi (24.1 MPa), 3000 psi (20.7 MPa), 2,500 psi (17.2 MPa), 2,000 psi (13.8 MPa), 1,500 psi (10.3 MPa), 1250 psi (8.62 MPa), or 1000 psi (6.89 MPa). Generally, the oligomer product can be formed at a reaction zone (or the reaction zone can have an) ethylene partial pressure ranging from any minimum ethylene partial pressure disclosed herein to any maximum ethylene partial pressure disclosed herein. In some non-limiting aspects, the oligomer product can be formed at a reaction zone (or the reaction zone can have an) ethylene partial pressure from 100 psi (689 kPa) to 5000 psi (34.5 MPa), 100 psi (689 kPa) to 2,500 psi (17.2 MPa), 100 psi (689 kPa) to 1000 psi (6.89 MPa), 500 psi (3.45 MPa) to 4500 psi (31 MPa), 500 psi (3.45 MPa) to 2,500 psi (17.2 MPa), 500 psi (3.45 MPa) to 1000 psi (6.89 MPa), 750 psi (5.17 MPa) to 4500 psi (31 MPa), 900 psi (6.21 MPa) to 4,000 psi (27.6 MPa), or 1000 psi (6.89 MPa) to 3500 psi (24.1 MPa). Other ethylene partial pressure ranges are readily apparent to those skilled in the art with the aid of this disclosure.

The oligomer product can be formed at a reaction zone (or the reaction zone can have a) minimum temperature of 0° C., 25° C., 40° C., 50° C., 75° C., 100° C. or 125° C.; alternatively or additionally, at a maximum temperature of 250° C., 200° C., 150° C., 125° C., 100° C., or 90° C. Generally, the oligomer product can be formed at a reaction zone (or the reaction zone can have a) temperature ranging from any minimum temperature disclosed herein to any maximum temperature disclosed herein. In some non-limiting aspects, the oligomer product can be formed at a reaction zone (or the reaction zone can have a) temperature from 0° C. to 250° C., from 25° C. to 200° C., from 40° C. to 150° C., from 40° C. to 100° C., from 50° C. to 100° C., from 50° C. to 150° C., from 75° C. to 125° C., from 75° C. to 250° C., from 100° C. to 200° C., or from 100° C. to 200° C. Other temperature ranges that can be utilized are readily apparent to those skilled in the art with the aid of this disclosure.

The oligomer product can be formed at a reaction zone (or the reaction zone can have) a minimum reaction zone zirconium of the zirconium compound to ethylene molar ratio of $5 \times 10^{-7}$:1, $1 \times 10^{-6}$:1 $5 \times 10^{-5}$:1, or $2.5 \times 10^{-5}$:1; additionally of alternatively, a maximum reaction zone zirconium of the zirconium compound to ethylene molar ratio of $7.5 \times 10^{-4}$:1, $5 \times 10^{-4}$:1, $2.5 \times 10^{-4}$:1, or $1 \times 10^{-4}$:1. Generally, reaction zone zirconium of the zirconium compound to ethylene molar ratio can range from any minimum reaction zone zirconium of the zirconium compound to ethylene molar ratio disclosed herein to any maximum reaction zone zirconium of the zirconium compound to ethylene molar ratio disclosed herein. In a non-limiting aspect, the reaction zone zirconium of the zirconium compound to ethylene molar ratio can range from $5 \times 10^{-7}$:1 to $1 \times 10^{-4}$:1, $1 \times 10^{-6}$:1 to $2.5 \times 10^{-4}$:1, $5 \times 10^{-5}$:1 to $5 \times 10^{-4}$:1, or $2.5 \times 10^{-5}$:1 to $7.5 \times$ $10^{-4}$:1. Other reaction zone zirconium of the zirconium compound to ethylene molar ratio ranges that can be utilized are readily apparent to those skilled in the art with the aid of this disclosure.

The oligomer product can be formed at a reaction zone (or the reaction zone can have a) minimum ethylene:organic reaction medium mass ratio of 0.5:1, 0.75:1, 1:1, 1.25:1, or 1.5:1; additionally or alternatively, a maximum ethylene:organic reaction medium mass ratio of 4.5:1, 4:1, 3.5:1, 3:1, 2.5:1, or 2:1. Generally, the oligomer product can be formed at a reaction (or the reaction zone can have an) ethylene:organic reaction medium mass ratio in the range from any minimum ethylene:organic reaction medium mass ratio disclosed herein to any maximum ethylene:organic reaction medium mass ratio disclosed herein. In some non-limiting aspects, the oligomer product can be formed at a reaction (or the reaction zone can have an) ethylene:organic reaction medium mass ratio in the range from 0.5:1 to 4.5:1, from 0.75:1 to 4:1, from 0.75:1 to 2:1, from 1:1 to 3:1, or from 1.5:1 to 2.5:1. Other ethylene:organic reaction medium mass ratio ranges that can be utilized are readily apparent to those skilled in the art with the aid of this disclosure.

The oligomer product can be formed at (or the reaction zone can have) any desired reaction zone residence time (or average reaction zone residence time). In an aspect, the oligomer product can be formed at a reaction zone residence time (or average reaction zone residence time) to produce a desired quantity of oligomer product, a desired catalyst system productivity, provide a desired ethylene conversion, or any combination thereof; alternatively, to produce a desired quantity of oligomer product; alternatively, a desired catalyst system productivity; or alternatively, provide a desired ethylene conversion. The oligomer product can be formed at (or the reaction zone can have) a minimum reaction zone residence time (or average reaction zone residence time) of 10 minutes, 20 minutes, or 30 minutes; additionally or alternatively, a maximum reaction zone residence time (or average reaction zone residence time) of 3 hours, 2.5 hours, 2 hours, or 1.5 hours. Generally, the reaction zone residence time (or average reaction zone residence time) can range from any minimum reaction zone residence time (or average reaction zone residence time) disclosed herein to any maximum reaction zone residence time (or average reaction zone residence time) disclosed herein. In some non-limiting aspects, the oligomer product can be formed at a reaction zone residence time (or average reaction zone residence time) ranging from 10 minutes to 2.5 hours, from 20 minutes to 2 hours, from 30 minutes to 2 hours, or from 30 minutes to 1.5 hours. Other reaction zone residence time (or average reaction zone residence time) ranges that can be utilized are readily apparent to those skilled in the art with the aid of this disclosure.

The oligomer product can have (or can be form having) a minimum Schultz-Flory K value of 0.4, 0.45, 0.5; or, 0.55; alternatively or additionally, a maximum Schultz-Flory K value of 0.9, 0.85, 0.8, 0.75, 0.7, or 0.65. The oligomer product can have (or can be form having) a Schultz-Flory K ranging from any minimum Schultz-Flory K value disclosed herein to any maximum Schultz-Flory K value disclosed herein. In a non-limiting aspect, the oligomer product can have (or can be form having) a Schultz-Flory K value in the range from 0.4 to 0.9, from 0.4 to 0.8, from 0.5 to 0.8, from 0.5 to 0.7, or from 0.55 to 0.7. Other oligomer product Schultz-Flory K value ranges are readily apparent from the present disclosure. In any aspect, the Schultz-Flory K value can be determined using adjacent pairs of oligomer product where both of the adjacent oligomer product are selected from $C_8$, $C_{10}$, $C_{12}$, $C_{14}$, or $C_{16}$ oligomer products. In an embodiment, the Schultz-Flory K value can be an average of any two or more Schultz-Flory K values using different adjacent pairs of produced oligomers described herein. In some aspects, the Schultz-Flory K value can be determined using the $C_5$ and $C_{10}$ oligomer products, the $C_{10}$ and $C_{12}$ oligomer products, the $C_{12}$ and $C_{14}$ oligomer products, the $C_{14}$ and $C_{16}$ oligomer product, the $C_8$, $C_{10}$, and $C_{12}$ oligomer product, or an average of any two more of adjacent pairs of oligomer products.

The oligomer product can be formed at any desired ethylene conversion (or single pass ethylene conversion). The oligomer product can be formed at a minimum ethylene conversion (or single pass ethylene conversion) of 30%, 35%, 40%, 45%, 50% or 55%; additionally or alternatively, a maximum ethylene conversion (or single pass ethylene conversion) of 95%, 90%, 87.5% 85%, or 80%. Generally, the oligomer product can be formed at an ethylene conversion (or single pass ethylene conversion) can range from any minimum ethylene conversion (or single pass ethylene conversion) disclosed herein to any maximum ethylene conversion (or single pass ethylene conversion) disclosed herein. In some non-limiting aspects, the oligomer product can be formed at an ethylene conversion (or single pass ethylene conversion) ranging from 30% to 90%, from 35% to 90%, from 40% to 87.5%, from 45% to 87.5%, from 50% to 85%, or from 55% to 85%. Other ethylene conversion (or single pass ethylene conversion) ranges that can be utilized are readily apparent to those skilled in the art with the aid of this disclosure. In some aspects, the oligomer product can be formed at an ethylene conversion to provide an oligomer product having a desired selectivity to normal alpha olefins (e.g., % of normal alpha olefin in a designated oligomer product carbon number).

The processes described herein can produce an oligomer product with high selectivity to normal alpha olefins. In an aspect, the $C_6$ olefin oligomer product produced by the process described herein can have a 1-hexene content of at least 98.5 wt. %, 98.75 wt. %, 99.0 wt. %, 99.25 wt. %. In an aspect, the $C_8$ olefin oligomer product produced by the process described herein can have a 1-octene content of at least a 1-octene content of at least 98 wt. %, 98.25 wt. %, 98.5 wt. %, 98.75 wt. %, or 99.0 wt. %. In an aspect, the $C_{10}$ olefin oligomer product produced by the process described herein can have a 1-decene content of at least 97.5 wt. %, 97.75 wt. %, 98 wt. %) 98.25 wt. %, or 98.5 wt. %. In an aspect, the $C_2$ olefin oligomer product produced by the process described herein can have a 1-dodecene content of at least 96.5 wt. %, 97 wt. %, 97.5 wt. %, 97.75 wt. %, or 98.0 wt. %. In an aspect, the processes described herein can produce an oligomer product that can have any combination of any $C_6$ olefin oligomer product 1-hexene content described herein, any $C_8$ olefin oligomer product 1-octene content described herein, any $C_{10}$ olefin oligomer product 1-decene content described herein, and/or any $C_8$ olefin oligomer product 1-octene content described herein. In some non-limiting aspect, the oligomer product can have a $C_6$ olefin oligomer product 1-hexene content of at least 99 wt. % and a $C_{12}$ olefin oligomer product 1-dodecene content of at least 97.5 wt. %; alternatively, a $C_8$ olefin oligomer product 1-octene content of at least 98.5 wt. % and a $C_2$ olefin oligomer product 1-dodecene octene content of at least 97.5 wt. %; or alternatively, a $C_6$ olefin oligomer product 1-hexene content of at least 99 wt. %, a $C_8$ olefin oligomer product 1-octene content of at least 98.5 wt. %, a $C_{10}$ olefin oligomer product 1-decene content of at least 98 wt. %, and a $C_{12}$ olefin oligomer product 1-dodecene content of at least 97.5 wt. %. Other combinations oligomer product normal alpha olefin contents are readily apparent from the present disclosure.

In an aspect, the processes described herein can produce an oligomer product having (a) less than 2.5 wt. %, 1 wt. %, 0.75 wt. %, 0.5 wt. %, or 0.25 wt. % of polymer, (b) less than 2.5 wt. %, 1 wt. %, 0.75 wt. %, 0.5 wt. %, or 0.25 wt. %, compounds having a weight average molecular weight of greater than 1000 g/mol, or (c) any combination thereof relative to the same process not using a 1) a chain transfer agent comprising a compound having a hydrogen silicon bond, a compound having a hydrogen sulfur bond, a compound having a hydrogen phosphorus bond, or any combination thereof, 2) hydrogen, and/or 3) a transition metal compound chain transfer agent. The wt. % polymer and the weight average molecular weight of the oligomer product is based on the total weight of the oligomer product. In another separate or combinable aspect, the processes described herein can produce an oligomer product having an oligomer product (a) comprising a polymer having a lower Mw, (b) an oligomer product where the polymer has a lower Mw maximum peak, (c) an oligomer product having a reduced quantity of polymer, (d) an oligomer product having a reduced % of polymer having a molecular weight greater than 100,000 molecular weight, or (e) any combination thereof relative to the same process not using a 1) a chain transfer agent comprising a compound having a hydrogen silicon bond, a compound having a hydrogen sulfur bond, a compound having a hydrogen phosphorus bond, or any combination thereof, 2) hydrogen, and/or 3) a transition metal compound chain transfer agent. In an aspect, the amount of polymer present in the oligomer product per gram of oligomer product produced can be decreased by at least 10%, 25%, 40%, 50%, 60%, 70%, or 80% as compared to polymer produced relative to the same process not using a 1) a chain transfer agent comprising a compound having a hydrogen silicon bond, a compound having a hydrogen sulfur bond, a compound having a hydrogen phosphorus bond, or any combination thereof, 2) hydrogen, and/or 3) a transition metal compound chain transfer agent. In an aspect, the amount of polymer having a molecular weight greater than 100,000 molecular weight can be decreased by at least 10%, 25%, 40%, 50%, 60%, 70%, or 80% as compared to polymer produced relative to the same process not using a 1) a chain transfer agent comprising a compound having a hydrogen silicon bond, a compound having a hydrogen sulfur bond, a compound having a hydrogen phosphorus bond, or any combination thereof, 2) hydrogen, and/or 3) a transition metal compound chain transfer agent.

The reaction zone in which the oligomer product is formed can comprise any suitable reactor. Non-limiting examples of reactor types can include a stirred tank reactor, a plug flow reactor, or any combination thereof; alternatively, a stirred tank reactor; alternatively, a plug flow reactor; alternatively, a fixed bed reactor, a continuous stirred tank reactor, a loop slurry reactor, a solution reactor, a tubular reactor, a recycle reactor, or any combination thereof; alternatively, a continuous stirred tank reactor; alternatively, a loop slurry reactor; alternatively, a solution reactor; alternatively, a tubular reactor; or alternatively, a recycle reactor. In an aspect, the reaction zone can have more than one reactor in series and/or in parallel and including any combination of reactor types and arrangements. Moreover, the oligomerization process used to form the oligomer product can be a continuous process, a semi-continuous process, or a batch process, or any reactor or vessel within the oligomerization reaction system can be operated continuously, semi-continuously, or batchwise.

Additional information regarding zirconium based catalyst systems for oligomerizing ethylene (including specific examples) and the process utilizing zirconium based catalyst system for producing an oligomer product can be found in, but not necessarily limited to, U.S. Pat. Nos. 4,361,714, 4,377,720, 4,396,788, 4,409,414, 4,410,750, 4,434,312, 4,434,313, 4,442,309, 4,486,615, 4,783,573, 4,855,525, 4,886,933, 4,966,874, 5,260,500, 6,576,721, 7,897,826, US 2003/0153798, U.S. Pat. Nos. 7,169,961, 7,291,685, 7,566,679, 8,269,055, US 2009/0216057, US 2009/0306312, US 2010/0191029, US 2010/0292423, US 2011/0046429, US 2011/0054130, US 2011/0054233, US 2012/0184692, US2020/0055799, US2020/0062672, US2020/0055800, US2020/0062673, EP 320,571 A2, EP 444,505 A2, EP 1,749,807 A1, EP 1,752,434 A1, EP 1,780,189, EP 2,258,674 A1, WO 91/02707, Sekiyu Gakkaishi, Vol. 37, No. 4, 1994, pp. 337-346, Sekiyu Gakkaishi, Vol. 42, No. 4, 1999, pp. 235-245, Sekiyu Gakkaishi, Vol. 43, No. 5, 2000, pp. 328-338, Sekiyu Gakkaishi, Vol. 44, No. 1, 2001, pp. 25-35, and Sekiyu Gakkaishi, Vol. 44, No. 2, 2001, pp. 109-119.

Examples

The disclosure is further illustrated by the following examples, which are not to be construed in any way as imposing limitations to the scope of this disclosure. Various other aspects, modifications, and equivalents thereof which, after reading the description herein, may suggest themselves to one of ordinary skill in the art without departing from the spirit of the present disclosure or the scope of the appended claims.

Ethylene Oligomerization Apparatus

FIG. 1 provides a diagram of the continuous ethylene oligomerization apparatus. The continuous ethylene oligomerization apparatus includes a 0.5 liter autoclave (functions as the reactor), a 5 gallon high pressure product tank, a primary catalyst system pump, a secondary catalyst system pump, an organic reaction medium pump, a hydrogen feedline, an chain transfer agent feedline, and associated equipment (e.g., valves and piping among other associated equipment). An autoclave effluent sample port is located on an autoclave effluent line running between the autoclave and the high pressure product tank. The reactor effluent line connecting the reactor and high pressure product tank is heat traced and the skin temperature is maintained at the reaction temperature. The 0.5 liter autoclave includes an overhead magnetic mechanical stirrer to provide mixing of the reaction mixture, and internal cooling coils (to flow a heat exchange fluid) and external heating jacket which are utilized as necessary to maintain the desired temperature. The continuous ethylene oligomerization apparatus also includes high-pressure nitrogen feed lines to the 0.5 liter autoclave reactor and product tank to provide an inert atmosphere to both vessels. The hydrogen feedline is connected to the ethylene feedline and metered to provide a desired hydrogen:ethylene ratio (when utilized), while the chain transfer agent feedline is connected to the organic reaction medium feedline on the suction side of the diluent pump and metered to provide a desired amount of chain transfer agent to the reactor. Catalyst system is fed to the reactor via one or two ISCO syringe pumps (catalyst system feed pumps) while organic reaction medium is feed from an organic reaction medium feed tank via an organic reaction medium pump. The continuous ethylene oligomerization apparatus utilizes the primary catalyst system solution feed pump when a prepared catalyst system is fed to the reactor, The continuous ethylene oligomerization apparatus utilizes the primary and secondary catalyst system feed pumps when two solutions containing the one or more components of the catalyst system are separately fed into a feed line to the reactor.

During the continuous ethylene oligomerization, a catalyst system pump(s) (ISCO syringe pumps) continuously fed(s) the catalyst system solution(s) to the reactor at the desired rate(s), an organic reaction medium pump continuously feds the organic reaction medium to the autoclave at the desired rate, and ethylene is continuously fed to the reactor though a mass flow meter connected at the desired rate, catalyst system and ethylene are introduced into the autoclave via a dip tube such that the catalyst system solution and ethylene enter the liquid contents of the autoclave at approximately the midpoint of the vertical height of the autoclave.

Example 1

In an argon atmosphere dry box, a 500 mL flask equipped with a stirrer is charged with 20 mmol of zirconium tetrachloride anhydride ($ZrCl_4$) and 250 mL of dry cyclohexane. The mixture is then stirred for 10 minutes at room temperature. To the stirred mixture is added triethylaluminum (TEA) and then ethylaluminum sesquichloride (EASC) to provide a mixture that has a EASC:TEA molar ratio of 3.5:1 and an aluminum to zirconium molar ratio of 7:1. The resultant mixture is then heated at 70° C. for 2 hours. The mixture is then cooled to room temperature. A 50 mL portion of the cooled mixture and is transferred to a one liter volumetric flask along with an amount of thiophene to thiophene:zirconium molar ratio of 3:1. The one liter volumetric is then charged with enough dry cyclohexane to provide one liter of catalyst system mixture. The zirconium concentration of the thus prepared catalyst system mixture/liter of cyclohexane and has an aluminum to zirconium molar ratio of 7:1, a EASC:TEA molar ratio of 3.5:1, and a thiophene:zirconium molar ratio of 3:1. The catalyst system mixture volumetric flask is then capped and removed from the argon atmosphere dry box.

Run 1-1 (Comparative)

The oligomerization apparatus as previously described is utilized using only the primary catalyst system solution pump. The oligomerization reactor is prepared for ethylene oligomerization by charging the high pressure product tank to the desired pressure using the high pressure $N_2$ fill line. The reactor is also cycled through three high pressure $N_2$ fill (to 800 psig-5.5 MPa) and vent cycles while isolated from the primary catalyst system solution pump. Each nitrogen purge is performed by closing the valve leading to the product tank, charging nitrogen to the autoclave through the spare entry port to a pressure of 800 psig (5.5 MPa), holding the nitrogen pressure on the autoclave for 5 minutes and then releasing the nitrogen pressure on the autoclave by opening the valve leading to the product tank. After the nitrogen of the final nitrogen purge is released, the autoclave is maintained with a slight residual nitrogen pressure. Catalyst system mixture, 200 mL, is then transferred to the catalyst system ISCO syringe pump of the prepared ethylene oligomerization apparatus. The reactor is then quickly filled organic reaction medium (cyclohexane). The diluent pump is then turned on at rate of 335 mL per hour to bring the reactor up to a reaction pressure of 925 psi (6.37 MPa). When the reactor achieves the reaction pressure, the overhead magnetic stirrer is started and set for ~1200 rpm and the heating jacket turned on and set for 120° C. When the reactor achieves a stable temperature of 120° C., the catalyst system ISCO pump is turned on and set to feed the catalyst system mixture to the reactor at a rate of 15 mL/hr. After 30 minutes, ethylene is then introduced into the reactor at an initial rate of at 50 grams/hour and gradually increased, over a 30 minute period, to a final rate of 175 grams/hour. The oligomerization temperature is maintained by using the internal cooling coils and external heating jacket as needed. After 6 hours, the oligomerization is terminated by decreasing the catalyst system flowrate to zero, decreasing the ethylene flow rate to zero, and turning off the heating jacket. When the reactor attains room temperature, the organic reaction medium flow rate is decreased to zero, and the liquid contents of the reactor pressured into the high pressure product tank using high pressure $N_2$.

The reactor is then opened and the solids inside the reactor and covering the internal reactor surfaces collected and added to the reactor effluent collected in the high pressure product tank. A liquid sample, 250 grams, of the product tank is collected and a known amount of internal standard (e.g. nonane) is added to the sample. The sample is then treated with 5 wt. % sodium hydroxide solution to deactivate the catalyst system. The organic layer of the sodium hydroxide treated sample is then analyzed using gas chromatographic analysis to determine oligomer product distribution, Schulz-Flory K value, carbon number purities, and catalyst system productivities. The remaining contents of the product tank are then homogenized and a second sample, 250 grams, of the product tank is taken. The second sample is then subjected to rotary evaporation for 1 h at 100° C. at -30 in Hg to effectively remove all the liquid. The mass of the remaining wax and polymer is determined. A portion of the wax is then analyzed by thermogravimetric analysis (TGA) to calculate the fraction of the solid sample that is polymer using the cutoffs of A) liquid ($\leq$175° C.), B) waxes (175° C. to 420° C., and C) polymer $\geq$420° C. A second portion of the wax and polymer is analyzed by HPLC to determine the molecular weight distribution of the polymer produced in the oligomerization including Mw, Mn, and Mp. The liquid and polymer analysis results are used to determine the oligomer product distribution, Schulz-Flory K value, carbon number purities, catalyst system productivities, polymer Mw, polymer Mw maximum peak, percentage of polymer in the oligomer product, percentage of polymer having an Mw greater than 100,000, and percentage of oligomer product having a Mw greater than 1,000 g/mol.

Run 1-2.

In an argon atmosphere dry box, a 250 mL volumetric flask is charged with 0.1 mole of triethylsilane (a chain transfer agent) and then charged with enough dry cyclohexane to provide 250 mL of chain transfer agent mixture. The chain transfer agent mixture volumetric flask is then capped and removed from the argon atmosphere dry box.

A chain transfer agent feed line is connected to organic reaction medium feedline on the suction side of the organic reaction medium pump. The procedure of Run 1-1 is repeated but with the addition of the triethylsilane solution to the suction side of the diluent pump metered to provide a triethylsilane to ethylene mole ratio of $1\times10^{-3}$:1 (~15 mL/hour when ethylene flowrate is 175 grams/hour) throughout the ethylene oligomerization.

Run 1-3

In an argon atmosphere dry box, a 250 mL volumetric flask is charged with 0.1 mmole of iron(III) octanoate (a transition metal compound chain transfer agent) and then charged with enough dry cyclohexane to provide 250 mL of transition metal compound chain transfer agent mixture. The chain transfer agent mixture volumetric flask is then capped and removed from the argon atmosphere dry box.

A transition metal compound chain transfer agent feed line is connected to organic reaction medium feedline on the suction side of the organic reaction medium pump. The procedure of Run 1-1 is repeated but with the addition of the iron(III) octanoate solution to the suction side of the diluent pump metered to provide an iron(III) octanoate to ethylene mole ratio of $1 \times 10^{-6}$:1 (~ 15 mL/hour when ethylene flowrate is 175 grams/hour) throughout the ethylene oligomerization.

Run 1-4

A hydrogen feed line is connected to the ethylene feedline of the ethylene oligomerization apparatus. The procedure of Run 1-1 is repeated but with hydrogen being metered into the ethylene at a rate to provide a hydrogen to ethylene mass ratio of (1 g hydrogen)/(kg ethylene) throughout the ethylene oligomerization.

The gas chromatographic analyses and HPLC analyses of ethylene oligomerization Runs, 1-2, 1-3, and 1-4 using a chain transfer agent were reviewed and compared to the gas chromatographic analyses and HPLC analyses of ethylene oligomerization Run 1-1. The analyses show that the oligomer product that is produced in ethylene oligomerization Runs 1-2, 1-3, and 1-4 using a chain transfer agent has less than 1 wt. % of polymer and/or less than 1 wt. % compounds having a weight average molecular weight of greater than 1000 g/mol, when compared to ethylene oligomerization Run 1-1 which did not utilize a chain transfer agent. The analyses also show that the oligomer product that is produced in ethylene oligomerization Runs 1-2, 1-3, and 1-4 using a chain transfer agent produces an oligomer product comprising a polymer having a lower Mw, a polymer having a lower Mw maximum peak, a reduced percentage of polymer, and/or a polymer having a reduced percentage of polymer having a Mw greater than 100,000 when compared to ethylene oligomerization Run 1-1 which did not utilize a chain transfer agent. The gas chromatographic analyses of the oligomer product of Runs, 1-1, 1-2, 1-3, and 1-4 indicate that there is no significant discernable impact on the Schulz-Flory K value, carbon number purities, and catalyst system productivities when a chain transfer agent is utilized in the ethylene oligomerization.

Example 2

In an argon atmosphere dry box, a first 500 mL flask equipped with a stirrer is charged with zirconium(IV) isopropylcarboxylate (60 mmol), anisole (45 mmol), and dry toluene (200 mL). This first mixture is then stirred for 10 minutes at room temperature. In the argon dry box, a second 500 mL flask equipped with a stirrer is charged with 2-pyrrolidone (43 mmol) and dry toluene (200 mL). To this second mixture is added neat diethylaluminum chloride (1.2 mol) over a period of 30 minutes. This second mixture is then stirred for an additional 10 minutes. The first mixture is then transferred to a one liter volumetric flask. The second mixture is then added to the first mixture in the volumetric flask and then the volumetric flask is charged with enough dry toluene to provide a one liter solution of the first catalyst system mixture. After through mixing, a 200 mL portion of the first catalyst system mixture is transferred to a second one liter volumetric flask along with enough dry toluene to provide one liter of a second catalyst system mixture. The zirconium concentration of the thus prepared second catalyst system mixture is 12 mmol/liter and has an anisole to zirconium molar ratio of 0.75:1, an aluminun:zirconium molar ratio of 20:1, and 2-pyrrolidone:Al ratio of 0.15:1. The second catalyst system mixture volumetric flask is then capped and removed from the argon atmosphere dry box.

Run 2-1 (Comparative)

The oligomerization apparatus as previously described is utilized using only the primary catalyst system solution pump. The oligomerization reactor is prepared for ethylene oligomerization by charging the high pressure product tank to the desired pressure using the high pressure $N_2$ fill line. The reactor is also cycled through three high pressure $N_2$ fill (to 800 psig-5.5 MPa) and vent cycles while isolated from the primary catalyst system solution pump. Each nitrogen purge is performed by closing the valve leading to the product tank, charging nitrogen to the autoclave through the spare entry port to a pressure of 800 psig (5.5 MPa), holding the nitrogen pressure on the autoclave for 5 minutes and then releasing the nitrogen pressure on the autoclave by opening the valve leading to the product tank. After the nitrogen of the final nitrogen purge is released, the autoclave is maintained with a slight residual nitrogen pressure. Second catalyst system mixture, 200 mL, is then transferred to the catalyst system ISCO syringe pump of the prepared ethylene oligomerization apparatus. The reactor is then quickly filled organic reaction medium (cyclohexane). The diluent pump is then turned on at rate of 485 mL per hour to bring the reactor up to a reaction pressure of 450 psi (3.1 MPa). When the reactor achieves the reaction pressure, the overhead magnetic stirrer is started and set for ~1200 rpm and the heating jacket turned on and set for 70° C. When the reactor achieves a stable temperature of 70° C., the catalyst system ISCO pump is turned on and set to feed the catalyst system mixture to the reactor at a rate of 15 mL/hr. After 30 minutes, ethylene is then introduced into the reactor at an initial rate of at 50 grams/hour and gradually increased, over a 30 minute period, to a final rate of 175 grams/hour. The oligomerization temperature is maintained by using the internal cooling coils and external heating jacket as needed. After 6 hours, the oligomerization is terminated by decreasing the catalyst system flowrate to zero, decreasing the ethylene flow rate to zero, and turning off the heating jacket. When the reactor attains room temperature, the organic reaction medium flow rate is decreased to zero, and the liquid contents of the reactor pressured into the high pressure product tank using high pressure $N_2$.

The reactor is then opened and the solids inside the reactor and covering the internal reactor surfaces collected and added to the reactor effluent collected in the high pressure product tank. A liquid sample, 250 grams, of the product tank is collected and a known amount of internal standard (e.g. nonane) is added to the sample. The sample is then treated with 5 wt. % sodium hydroxide solution to deactivate the catalyst system. The organic layer of the sodium hydroxide treated sample is then analyzed using gas chromatographic analysis to determine oligomer product distribution, Schulz-Flory K value, carbon number purities, and catalyst system productivities. The remaining contents of the product tank are then homogenized and a second sample, 250 grams, of the product tank is taken. The second sample is then subjected to rotary evaporation for 1 h at 100° C. at −30 in Hg to effectively remove all the liquid. The mass of the remaining wax and polymer is determined. A portion of the wax is then analyzed by thermogravimetric analysis (TGA) to calculate the fraction of the solid sample that is polymer using the cutoffs of A) liquid (≤175° C.), B) waxes (175° C. to ≥420° C., and C) polymer ≥420° C. A second portion of the wax and polymer is analyzed by HPLC to determine the molecular weight distribution of the polymer produced in the oligomerization including Mw, Mn, and Mp. The liquid and polymer analysis results are used to determine the oligomer product distribution, Schulz-Flory K value, carbon number purities, catalyst system productivities, polymer Mw, polymer Mw maximum peak, percentage of polymer in the oligomer product, percentage of polymer having
Run 2-2.

In an argon atmosphere dry box, a 250 mL volumetric flask is charged with 0.1 mole of triethylsilane (a chain transfer agent) and then charged with enough dry cyclohexane to provide 250 mL of chain transfer agent mixture. The chain transfer agent mixture volumetric flask is then capped and removed from the argon atmosphere dry box.

A chain transfer agent feed line is connected to organic reaction medium feedline on the suction side of the organic reaction medium pump. The procedure of Run 2-1 is repeated but with the addition of the triethylsilane solution to the suction side of the diluent pump metered to provide a triethylsilane to ethylene mole ratio of $1\times10^{-3}:1$ (~15 mL/hour when ethylene flowrate is 175 grams/hour) throughout the ethylene oligomerization.
Run 2-3

In an argon atmosphere dry box, a 250 mL volumetric flask is charged with 0.1 mmole of iron(III) octanoate (a transition metal compound chain transfer agent) and then charged with enough dry cyclohexane to provide 250 mL of transition metal compound chain transfer agent mixture. The chain transfer agent mixture volumetric flask is then capped and removed from the argon atmosphere dry box.

A transition metal compound chain transfer agent feed line is connected to organic reaction medium feedline on the suction side of the organic reaction medium pump. The procedure of Run 2-1 is repeated but with the addition of the iron(III) octanoate solution to the suction side of the diluent pump metered to provide an iron(III) octanoate to ethylene mole ratio of $1\times10^{-6}:1$ (~ 15 mL/hour when ethylene flowrate is 175 grams/hour) throughout the ethylene oligomerization.
Run 2-4

A hydrogen feed line is connected to the ethylene feedline of the ethylene oligomerization apparatus. The procedure of Run 2-1 is repeated but with hydrogen being metered into the ethylene at a rate to provide a hydrogen to ethylene mass ratio of (1 g hydrogen)/(kg ethylene) throughout the ethylene oligomerization.

The gas chromatographic analyses and HPLC analyses of ethylene oligomerization Runs, 2-2, 2-3, and 2-4 using a chain transfer agent were reviewed and compared to the gas chromatographic analyses and HPLC analyses of ethylene oligomerization Run 2-1. The analyses show that the oligomer product that is produced in ethylene oligomerization Runs 2-2, 2-3, and 2-4 using a chain transfer agent has less than 1 wt. % of polymer and/or less than 1 wt. % compounds having a weight average molecular weight of greater than 1000 g/mol, when compared to ethylene oligomerization Run 2-1 which did not utilize a chain transfer agent. The analyses also show that the oligomer product that is produced in ethylene oligomerization Runs 2-2, 2-3, and 2-4 using a chain transfer agent produces an oligomer product comprising a polymer having a lower Mw, a polymer having a lower Mw maximum peak, a reduced percentage of polymer, and/or a polymer having a reduced percentage of polymer having a Mw greater than 100,000 when compared to ethylene oligomerization Run 1-1 which did not utilize a chain transfer agent. The gas chromatographic analyses of the oligomer product of Runs, 2-1, 2-2, 2-3, and 2-4 indicate that there is no significant discernable impact on the Schulz-Flory K value, carbon number purities, and catalyst system productivities when a chain transfer agent is utilized in the ethylene oligomerization Example 3

In an argon atmosphere dry box, a first 500 mL flask equipped with a stirrer is charged with zirconium tetrachloride (100 mmol), isodecylacetates (105 mmol), and dry ortho-xylene (200 mL). This zirconium mixture is then stirred for 10 minutes at room temperature. The first zirconium mixture then transferred to a one liter volumetric flask and the one liter volumetric flask is then charged with enough ortho-xylene to provide a one liter solution of first zirconium solution. After through mixing, a 200 mL portion of the first zirconium solution is transferred to a second one liter volumetric flask along with enough dry ortho-xylene to provide one liter of a second zirconium solution. The second zirconium solution has an isodecylacetates:Zr molar ratio of 1.05:1. The second zirconium solution volumetric flask is then capped and removed from the argon atmosphere dry box.

In the argon dry box, a second 500 mL flask equipped with a stirrer is charged with dry ortho-xylene (500 mL). To the ortho-xylene added, with stirring, neat diethylaluminum chloride (1.2 mol) over a period of 30 minutes. This mixture is then stirred for an additional 10 minutes. This diethylaluminum chloride solution is then transferred to a one liter volumetric flask and the one liter volumetric flask is then charged with enough ortho-xylene to provide a one liter solution of first zirconium solution. After through mixing, a 200 mL portion of the first diethylaluminum chloride solution is transferred to a second one liter volumetric flask along with enough dry ortho-xylene to provide one liter of a second diethylaluminum chloride solution. The second diethylaluminum chloride solution volumetric flask is then capped and removed from the argon atmosphere dry box.
Run 3-1 (Comparative)

The oligomerization apparatus as previously described is utilized with the following modification: the 500 mL autoclave is replaced by a 200 mL autoclave (also equipped with an overhead magnetic mechanical stirrer to provide mixing of the reaction mixture, and internal cooling coils and external heating jacket) and both the primary and secondary catalyst system pumps are utilized. The oligomerization reactor is prepared for ethylene oligomerization by charging the high pressure product tank to the desired pressure using the high pressure $N_2$ fill line. The reactor is also cycled through three high pressure $N_2$ fill (to 800 psig-5.5 MPa) and vent cycles while isolated from the primary and secondary catalyst system solution pump. Each nitrogen purge is performed by closing the valve leading to the product tank, charging nitrogen to the autoclave through the spare entry port to a pressure of 800 psig (5.5 MPa), holding the nitrogen pressure on the autoclave for 5 minutes and then releasing the nitrogen pressure on the autoclave by opening the valve leading to the product tank. After the nitrogen of the final nitrogen purge is released, the autoclave is maintained with a slight residual nitrogen pressure. Second zirconium mixture, 200 mL, is transferred to the primary catalyst system ISCO syringe pump of the prepared ethylene oligomerization apparatus. Second diethylaluminum chloride solution, 200 mL, is transferred to the secondary catalyst system ISCO syringe pump of the prepared ethylene oligomerization apparatus. The reactor is then quickly filled dry organic reaction medium (ortho-xylene). The diluent pump is then turned on at rate of 680 mL per hour to bring the reactor up to a reaction pressure of 3000 psi (20.7 MPa). When the reactor achieves the reaction pressure, the overhead magnetic stirrer is started and set for ~1200 rpm and the heating jacket turned on and set for 165° C. When the reactor achieves a stable temperature of 70° C., the primary and secondary catalyst system ISCO pumps are turned on and set to feed the second zirconium solution and the second diethylaluminum chloride solutions at a rate of 11 mL/hr. The feed rate of the zirconium solution and the diethylaluminum chloride solution provide an Al:Zr ratio of 12:1. After 30 minutes, ethylene is then introduced into the reactor at an initial rate of at 50 grams/hour and gradually increased, over a 30 minute period, to a final rate of 600 grams/hour. The oligomerization temperature is maintained by using the internal cooling coils and external heating jacket as needed. After 4 hours, the oligomerization is terminated by decreasing the flowrate of the zirconium solution and the diethylaluminum chloride solution feed rates to zero, decreasing the ethylene flow rate to zero, and turning off the heating jacket. When the reactor attains room temperature, the organic reaction medium flow rate is decreased to zero, and the liquid contents of the reactor pressured into the high pressure product tank using high pressure N.

The reactor is then opened and the solids inside the reactor and covering the internal reactor surfaces collected and added to the reactor effluent collected in the high pressure product tank. A liquid sample, 250 grams, of the product tank is collected and a known amount of internal standard (e.g. nonane) is added to the sample. The sample is then treated with 5 wt. % sodium hydroxide solution to deactivate the catalyst system. The organic layer of the sodium hydroxide treated sample is then analyzed using gas chromatographic analysis to determine oligomer product distribution, Schulz-Flory K value, carbon number purities, and catalyst system productivities. The remaining contents of the product tank are then homogenized and a second sample, 250 grams, of the product tank is taken. The second sample is then subjected to rotary evaporation for 1 h at 100° C. at −30 in Hg to effectively remove all the liquid. The mass of the remaining wax and polymer is determined. A portion of the wax is then analyzed by thermogravimetric analysis (TGA) to calculate the fraction of the solid sample that is polymer using the cutoffs of A) liquid ($\leq 175°$ C.), B) waxes (175° C. to 420° C., and C) polymer $\geq 420°$ C. A second portion of the wax and polymer is analyzed by HPLC to determine the molecular weight distribution of the polymer produced in the oligomerization including Mw, Mn, and Mp. The liquid and polymer analysis results are used to determine the oligomer product distribution, Schulz-Flory K value, carbon number purities, catalyst system productivities, polymer Mw, polymer Mw maximum peak, percentage of polymer in the oligomer product, percentage of polymer having
Run 3-2.

In an argon atmosphere dry box, a 250 mL volumetric flask is charged with 360 mmol of triethylsilane (a chain transfer agent) and then charged with enough dry ortho-xylene to provide 250 mL of chain transfer agent mixture. The chain transfer agent mixture volumetric flask is then capped and removed from the argon atmosphere dry box.

A chain transfer agent feed line is connected to organic reaction medium feedline on the suction side of the organic reaction medium pump. The procedure of Run 3-1 is repeated but with the addition of the triethylsilane solution to the suction side of the diluent pump metered to provide a triethylsilane to ethylene mole ratio of $1 \times 10^{-3}$:1 (~15 mL/hour when ethylene flowrate is 600 grams/hour) throughout the ethylene oligomerization.
Run 3-3

In an argon atmosphere dry box, a 250 mL volumetric flask is charged with 0.36 mmole of iron(III) octanoate (a transition metal compound chain transfer agent) and then charged with enough dry cyclohexane to provide 250 mL of transition metal compound chain transfer agent mixture. The chain transfer agent mixture volumetric flask is then capped and removed from the argon atmosphere dry box.

A transition metal compound chain transfer agent feed line is connected to organic reaction medium feedline on the suction side of the organic reaction medium pump. The procedure of Run 3-1 is repeated but with the addition of the iron(III) octanoate solution to the suction side of the diluent pump metered to provide an iron(III) octanoate to ethylene mole ratio of $1 \times 10^{-6}$:1 (~ 15 mL/hour when ethylene flowrate is 175 grams/hour) throughout the ethylene oligomerization.
Run 3-4

A hydrogen feed line is connected to the ethylene feedline of the ethylene oligomerization apparatus. The procedure of Run 3-1 is repeated but with hydrogen being metered into the ethylene at a rate to provide a hydrogen to ethylene mass ratio of (1 g hydrogen)/(kg ethylene) throughout the ethylene oligomerization.

The gas chromatographic analyses and HPLC analyses of ethylene oligomerization Runs, 3-2, 3-3, and 3-4 using a chain transfer agent were reviewed and compared to the gas chromatographic analyses and HPLC analyses of ethylene oligomerization Run 3-1. The analyses show that the oligomer product that is produced in ethylene oligomerization Runs 3-2, 3-3, and 3-4 using a chain transfer agent has less than 1 wt. % of polymer and/or less than 1 wt. % compounds having a weight average molecular weight of greater than 1000 g/mol, when compared to ethylene oligomerization Run 3-1 which did not utilize a chain transfer agent. The analyses also show that the oligomer product that is produced in ethylene oligomerization Runs 3-2, 3-3, and 3-4 using a chain transfer agent produces an oligomer product comprising a polymer having a lower Mw, a polymer having a lower Mw maximum peak, a reduced percentage of polymer, and/or a polymer having a reduced percentage of polymer having a Mw greater than 100,000 when compared to ethylene oligomerization Run 3-1 which did not utilize a chain transfer agent. The gas chromatographic analyses of the oligomer product of Runs, 3-1, 3-2, 3-3, and 3-4 indicate that there is no significant discernable impact on the Schulz-Flory K value, carbon number purities, and catalyst system productivities when a chain transfer agent is utilized in the ethylene oligomerization Illustrative statements of the subject matter claimed herein below will now be provided. In the interest of clarity, not all features of an actual implementation are described in this specification. It can be appreciated that in the development of any such actual embodiment, numerous implementation-specific decisions must be made to achieve the developers' specific goals, such as compliance with system-related and business-related constraints, which can vary from one implementation to another. Moreover, it can be appreciated that such a development effort, even if complex and time-consuming, would be a routine undertaking for those of ordinary skill in the art having the benefit of this disclosure. Furthermore, various modifications can be made within the scope of the invention as herein intended, and embodiments of the invention can include combinations of features other than those expressly claimed. In particular, flow arrangements other than those expressly described herein are within the scope of the invention.

Statement 1. A process comprising: a) contacting i) ethylene, ii) a catalyst system (or catalyst system components) comprising 1) a zirconium compound having the formula $ZrX^1{}_mY^1{}_q$, where each $X^1$ independently is a halide, each $Y^1$ independently is a hydrocarboxide, a dihydrocarbylazanide, a hydrocarbylcarboxylate, a hydrocarbylsulfonate, or a β-diketonate, n is a range from 0 to 4, q is in a range from 0 to 4, and m+q is an integer from 2 to 4, and 2) a hydrocarbylmetal compound, iii) a chain transfer agent comprising a compound having a hydrogen silicon bond, a compound having a hydrogen sulfur bond, a compound having a hydrogen phosphorus bond, or any combination thereof, and iv) optionally, an organic reaction medium; and b) forming an oligomer product in the reaction zone.

Statement 2. A process comprising: a) introducing i) ethylene, ii) a catalyst system (or catalyst system components) comprising 1) a zirconium compound having the formula $ZrX^1{}_mY^1{}_q$, where each $X^1$ independently is a halide, each $Y^1$ independently is a hydrocarboxide, a dihydrocarbylazanide, a hydrocarbylcarboxylate, a hydrocarbylsulfonate, or a 0-diketonate, m is a range from 0 to 4, q is in a range from 0 to 4, and m+q is an integer from 2 to 4, and 2) a hydrocarbylmetal compound, iii) a chain transfer agent comprising a compound having a hydrogen silicon bond, a compound having a hydrogen sulfur bond, a compound having a hydrogen phosphorus bond, or any combination thereof, and iv) optionally, an organic reaction medium into a reaction zone; and b) forming an oligomer product in a reaction zone.

Statement 3. The process of statement 1 or 2, wherein the chain transfer agent comprises a compound having the formula $R^{31}SiH_3$, $(R^{31})_2SiH_2$, $(R^{31})_3SiH$, $R^{31}OSiH_3$, $(R^{31}O)_2SiH_2$, $(R^{31}O)_3SiH$, $R^{32}SH$, $R^{32}CO_2CH_2SH$, $R^{32}CO_2CH_2CH_2SH$, $R^{33}PH_2$, $(R^{33})_2PH$, $R^{33}PH_2$, $(R^{33}O)_2PH$, or any combination thereof wherein each $R^{31}$, $R^{32}$, and $R^{33}$ independently are a $C_1$ to $C_{15}$ hydrocarbyl group.

Statement 4. The process of any one of statements 1-3, wherein the reaction zone has any hydrogen of the chain transfer agent to ethylene mole ratio disclosed herein e.g., (a minimum value of $1\times10^{-5}$: 1, $5\times10^{-4}$:1, $1\times10^{-4}$:1, or $5\times10^{-3}$:1; a maximum value of $5\times10^{-1}$: 1, $1\times10^{-1}$: 1, $5\times10^{-2}$:1, or $1\times10^{-2}$:1; in a range from $1\times10^{-5}$:1 to $5\times10^{-1}$:1, $5\times10^{-4}$:1 to $1\times10^{-1}$:1, $1\times10^{-4}$:1 to $5\times10^{-2}$:1, or $5\times10^{-3}$:1 to $1\times10^{-2}$:1; among others values and ranges).

Statement 5. A process comprising: a) contacting i) ethylene, ii) a catalyst system (or catalyst system components) comprising 1) a zirconium compound having the formula $ZrX^1{}_mY^1{}_q$, where each $X^1$ independently is a halide, each $Y^1$ independently is a hydrocarboxide, a dihydrocarbylazanide, a hydrocarbylcarboxylate, a hydrocarbylsulfonate, or a β-diketonate, m is a range from 0 to 4, q is in a range from 0 to 4, and m+q is an integer from 2 to 4, and 2) a hydrocarbylmetal compound, iii) hydrogen, and iv) optionally, an organic reaction medium; and b) forming an oligomer product in a reaction zone.

Statement 6. A process comprising: a) introducing i) ethylene, ii) a catalyst system (or catalyst system components) comprising 1) a zirconium compound having the formula $ZrX^1{}_mY^1{}_q$, where each $X^1$ independently is a halide, each $Y^1$ independently is a hydrocarboxide, a dihydrocarbylazanide, a hydrocarbylcarboxylate, a hydrocarbylsulfonate, or a β-diketonate, m is a range from 0 to 4, q is in a range from 0 to 4, and m+q is an integer from 2 to 4, and 2) a hydrocarbylmetal compound, iii) hydrogen, and iv) optionally, an organic reaction medium into a reaction zone; and b) forming an oligomer product in the reaction zone.

Statement 7. The process of statement 5 or 6, wherein the reaction zone has any hydrogen to ethylene mass ratio disclosed herein (e.g., a minimum value of (0.05 g hydrogen)/(kg ethylene), (0.1 g hydrogen)/(kg ethylene), (0.25 g hydrogen)/(kg ethylene), (0.4 g hydrogen)/(kg ethylene), or (0.5 g hydrogen)/(kg ethylene); a maximum value of (5 g hydrogen)/(kg ethylene), (3 g hydrogen)/(kg ethylene), (2.5 g hydrogen)/(kg ethylene), (2 g hydrogen)/(kg ethylene), or (1.5 g hydrogen)/(kg ethylene); in a range from (0.05 g hydrogen)/(kg ethylene) to (5 g hydrogen)/(kg ethylene), from (0.25 g hydrogen)/(kg ethylene) to (5 g hydrogen)/(kg ethylene), from (0.25 g hydrogen)/(kg ethylene) to (4 g hydrogen)/(kg ethylene), from (0.4 g hydrogen)/(kg ethylene) to (3 g hydrogen)/(kg ethylene), from (0.4 g hydrogen)/(kg ethylene) to (2.5 g hydrogen)/(kg ethylene), from (0.4 g hydrogen)/(kg ethylene) to (2 g hydrogen)/(kg ethylene), or from (0.5 g hydrogen)/(kg ethylene) to (2 g hydrogen)/(kg ethylene); among others values and ranges.

Statement 8. A process comprising: a) contacting i) ethylene, ii) a catalyst system (or catalyst system components) comprising 1) a zirconium compound having the formula $ZrX^1{}_mY^1{}_q$, where each $X^1$ independently is a halide, each $Y^1$ independently is a hydrocarboxide, a dihydrocarbylazanide, a hydrocarbylcarboxylate, a hydrocarbylsulfonate, or a β-diketonate, m is a range from 0 to 4, q is in a range from 0 to 4, and m+q is an integer from 2 to 4, and 2) a hydrocarbylmetal compound, iii) a transition metal compound chain transfer agent, and iv) optionally, an organic reaction medium; and b) forming an oligomer product in a reaction zone.

Statement 9. A process comprising: a) introducing i) ethylene, ii) a catalyst system (or catalyst system components) comprising 1) a zirconium compound having the formula $ZrX^1{}_mY^1{}_q$, where each $X^1$ independently is a halide, each $Y^1$ independently is a hydrocarboxide, a dihydrocarbylazanide, a hydrocarbylcarboxylate, a hydrocarbylsulfonate, or a β-diketonate, n is a range from 0 to 4, q is in a range from 0 to 4, and m+q is an integer from 2 to 4, and 2) a hydrocarbylmetal compound, iii) a transition metal compound chain transfer agent, and iv) optionally, an organic reaction medium into a reaction zone; and b) forming an oligomer product in the reaction zone.

Statement 10. The process of statement 8 or 9, wherein the transition metal compound chain transfer agent is any transition metal compound chain transfer agent having the formula $MX^4{}_p$ where M is the transition metal, $X^4$ is a mono anion, and p is an integer from 2 to 4.

Statement 11. The process of statement 10, wherein the transition metal compound chain transfer agent is any described herein having the formula $MX^4{}_p$ where M is iron, cobalt, or nickel.

Statement 12. The process of statement 10 or 11, wherein transition metal compound chain transfer agent is any transition metal compound chain transfer agent having the formula $MX^4{}_p$ described herein where $X^4$ is a $C_4$ to $C_{19}$ carboxylate.

Statement 13. The process of statement of any one of statements 8 to 12, wherein the reaction zone has any transition metal of the transition metal compound chain transfer agent to ethylene mole ratio disclosed herein (a minimum value of $1\times10^{-9}$:1, $5\times10^{-8}$:1, $1\times10^{-8}$:1, $5\times10^{-7}$:1, or $1\times10^{-7}$:1; a maximum value of $5\times10^{-3}$:1, $1\times10^{-3}$:1, $5\times10^{-4}$:1, $1\times10^{-4}$:1, or $5\times10^{-5}$:1; in a range from $1\times10^{-9}$:1 to $5\times10^{-3}$:1, $5\times10^{-8}$:1 to $1\times10^{-3}$:1, $1\times10^{-8}$:1 to $5\times10^{-4}$:1, $5\times10^{-7}$:1 to $1\times10^{-4}$:1, or $1\times10^{-7}$:1 to $5\times10^{-5}$:1; among others values and ranges).

Statement 14. The process of any one of Statements 1-13, wherein the hydrocarbylmetal compound is any hydrocarbylmetal compound disclosed herein (e.g., comprise any metal disclosed herein— a group 1, 2, 11, 12, 13, or 14 metal, among other metal groups disclosed herein—and any hydrocarbyl group disclosed herein—a $C_1$ to $C_{20}$, a $C_1$ to $C_{10}$, or a $C_1$ to $C_6$ hydrocarbyl group and other more specific hydrocarbyl groups disclosed herein).

Statement 15. The process of any one of Statements 1-14, wherein the metal of the hydrocarbylmetal compound to zirconium of the zirconium compound is any value disclosed herein (e.g., a minimum value of 0.1:1, 0.2:1, 0.6:1, 1:1, 2:1 10:1; a the maximum value or 100:1 75:1, 50:125:1, 15:1, or 10:1; or in a range of from 0.1:1 to 100:1, 0.2:1 to 75:1, 0.6:1 to 25:1, 1:1 to 50:1, 2:1 to 25:1, 1:1 to 15:1, 2:1 to 10:1, 10:1 to 50:1, or 10:1 to 25:1; among others values and ranges).

Statement 16. The process of any one of statement 1-15, wherein the catalyst system (or catalyst system components) further comprises a neutral non-ionic organic modifier.

Statement 17. The process of statement 16, wherein the neutral non-ionic organic modifier comprises any an ether, an ester, a ketone, an aldehyde, an alcohol, an anhydride, an acid chloride, a nitrile, a sulfide, a disulfide, a phosphine, an amine, or an amide described herein.

Statement 18. The process of statement 16 or 17, wherein the neutral non-ionic organic modifier to zirconium of the zirconium compound molar ratio can have any values described herein (e.g., a minimum value of 0.1:1, 0.5:1, 0.75:1 0.8:1, 0.9:1, or 1:1; a maximum value of 20:1, 15:1, 10:1 7.5:1, or 5:1; or in a range from 0.5:1 20:1, 0.5:1 to 15:1, 0.75: 10:1, 1:1 to 15:1, 1:1 to 10:1, 1:1 to 5:1, 0.5:1 to 5:1, 0.75:1 to 3:1, 0.8:1 to 2:1, 0.9:1 or 1.25; among other values and ranges.

Statement 19. The process of any one of statements 16-18, wherein neutral non-ionic organic modifier to hydrocarbylmetal (or hydrocarbylaluminum) compound molar ratio can have any value described herein (e.g., an minimum value of be 0.05:1, 0.1:1, 0.5:1, 0.75:1 0.8:1, 0.9:1, or 1:1; a maximum value of 5:1, 3:1, 2:1, 1.5:1, 1:1, 0.75:1, or 0.5:1; or in a range from 0.05: to 5:1, 0.1 to 1:1, 0.1:1 to 0.5:1, 0.5:1 to 5:1, 0.5:1 to 3:1, 0.75:1 to 2:1, or 0.75:1 to 1.5:1; among other values and ranges.

Statement 20. The process of any one of statements 1-19, wherein the zirconium compound has the formula $ZrX^1_m Y^1_q$, where each $X^1$ independently is chloride or bromide, each $Y^1$ independently is a $C_1$ to $C_{10}$ hydrocarboxide (e.g., any described herein), a $C_1$ to $C_{15}$ hydrocarbylcarboxylate (e.g., any described herein), or a $C_1$ to $C_{15}$ hydrocarbylsulfonate (e.g., any described herein), m is a range from 0 to 4, q is in a range from 0 to 4, and m+q is 4.

Statement 21. The process of any one of statements 1-20, wherein the hydrocarbylmetal compound comprises an alkylaluminum compound having the formula $AlX^2_{3-n}R^1_n$, $Al_2X^2_{6-q}R^1_q$, $R^1_2Zn$, or any combination thereof, where each $R^1$ independently is a $C_1$ to $C_{10}$ alkyl group, each $X^2$ independently is chloride, bromide, or iodide, n is an integer from 0 to 3, and q is an integer for 0 to 6.

Statement 22. The process of any one of statements 20-22, wherein the neutral non-ionic organic modifier comprises any $C_2$ to $C_{20}$ ether, $C_3$ to $C_{20}$ ester, $C_3$ to $C_{20}$ ketone, $C_2$ to $C_{20}$ nitrile, $C_2$ to $C_{20}$ sulfide, $C_2$ to $C_{20}$ disulfide, $C_3$ to $C_{20}$ phosphine, $C_1$ to $C_{20}$ amine, or $C_2$ to $C_{20}$ amide described herein.

Statement 23. The process of any one of statements 1-19, wherein the zirconium compound has the formula $ZrX^1_m$ where each $X^1$ independently is a chloride or bromide and m is 4, the hydrocarbylmetal compound has the formula $AlX^2_n R^1_{3-n}$, $Al_2X^2_3 R^1_3$, $R^1_2Zn$, or any combination thereof where each $X^2$ independently is a halide and each $R^1$ independently is $C_2$ to $C_4$ alkyl group, and the metal of the hydrocarbylmetal (or aluminum of the hydrocarbylaluminum) compound to zirconium of the zirconium compound molar ratio is in any range disclosed herein (e.g., in a range of from 1:1 to 50:1).

Statement 24. The process of statement 23, wherein the catalyst system (or catalyst system components) further comprise a neutral non-ionic organic modifier comprising $C_2$ to $C_{20}$ ester, and wherein the neutral non-ionic organic modifier to zirconium of the zirconium compound molar ratio is in is in any range disclosed herein (e.g., in a range of from 0.5:1 to 5:1), and the metal of the hydrocarbylmetal (or aluminum of the hydrocarbylaluminum) compound to zirconium of the zirconium compound molar ratio is in any range disclosed herein (e.g., in a range of from 10:1 to 25:1).

Statement 25. The process of statement 24, wherein the neutral non-ionic organic modifier is contacted with the zirconium compound prior to the zirconium compound contacting ethylene and/or the hydrocarbylmetal compound (and/or being introduced into the reaction zone).

Statement 26. The process of statement 23 or 24, wherein the catalyst system (or catalyst system components) further comprise a neutral non-ionic organic modifier comprising a $C_2$ to $C_{20}$ ether, a $C_2$ to $C_{20}$ sulfide, a $C_1$ to $C_{20}$ amine, a $C_3$ to $C_{20}$ phosphine, or any combination thereof, and wherein the neutral non-ionic organic modifier to zirconium of the zirconium compound molar ratio is in any range disclosed herein (e.g., in a range of from 0.5:1 to 20:1), and the metal of the hydrocarbylmetal (or aluminum of the hydrocarbylaluminum) compound to zirconium of the zirconium compound molar ratio is in any range disclosed herein (e.g., in a range of from 1:1 to 15:1).

Statement 27. The process of any one of statements 1-19, where the zirconium compound has the formula $ZrX^1_m Y^1_q$, where each $X^1$ independently is chloride or bromide, each $Y^1$ independently is a $C_1$ to $C_{10}$ hydrocarboxide (e.g., any described herein), a $C_1$ to $C_{10}$ hydrocarbylcarboxylate (e.g., any described herein), or a $C_1$ to $C_{15}$ hydrocarbylsulfonate (e.g., any described herein), m is a range from 0 to 4, q is in a range from 0 to 4, and m+q is 4, the hydrocarbylmetal compound comprises a hydrocarbylmetal compound having the formula $AlX^2_n R^1_{3-n}$, $Al_2X^2_3 R^1_3$, or any combination thereof where each $X^2$ independently is a halide and each $R^1$ independently is $C_2$ to $C_4$ alkyl group, and the metal of the hydrocarbylmetal (or aluminum of the hydrocarbylaluminum) compound to zirconium of the zirconium compound molar ratio is in a range of from 1:1 to 50:1.

Statement 28. The process of statement 27, wherein the zirconium compound is at least partially hydrolyzed by contacting the zirconium compound with water using any water to zirconium molar ratio disclosed herein (e.g., 0.01:1 to 3:1, 0.1: to 2:1, 0.25:1 to 1.75:1).

Statement 29. The process of statement 27 or 28, wherein the catalyst system (or catalyst system components) further comprise a neutral non-ionic organic modifier comprising a $C_2$ to $C_{15}$ amide, and wherein the neutral non-ionic organic modifier to metal of the hydrocarbylmetal (or aluminum of the hydrocarbylaluminum) compound molar ratio is in a range of 0.1:1 to 1:1.

Statement 30. The process of statement 29, wherein the neutral non-ionic organic modifier is contacted with the hydrocarbylmetal (or hydrocarbylaluminum) compound prior to the hydrocarbylmetal (or hydrocarbylaluminum) compound contacting ethylene (and/or being introduced into the reaction zone).

Statement 31. The process of any one of statements 27-30, wherein the catalyst system (or catalyst system components) further comprise a neutral non-ionic organic modifier comprising a $C_2$ to $C_{20}$ ether, a $C_2$ to $C_{20}$ sulfide, a $C_1$ to $C_{20}$ amine, or any combination thereof, and wherein the neutral non-ionic organic modifier to zirconium of the zirconium compound is in any range disclosed herein (e.g., in a range of from 0.1:1 to 10:1).

Statement 32. The process of statement 31, wherein the neutral non-ionic organic modifier is contacted with the zirconium compound prior to the zirconium compound contacting ethylene and/or the hydrocarbylmetal compound (and/or being introduced into the reaction zone).

The process of any one of statements 1-32, wherein the oligomer product is formed at (or the reaction zone has) any reaction zone zirconium of the zirconium compound to ethylene molar ratio described herein (e.g., a minimum reaction zone zirconium of the zirconium compound to ethylene molar ratio of $5 \times 10^{-7}$:1, $1 \times 10^{-6}$:1, $5 \times 10^{-5}$:1, or $2.5 \times 10^{-5}$:1; a maximum reaction zone zirconium of the zirconium compound to ethylene molar ratio of $7.5 \times 10^{-4}$:1, $5 \times 10^{-4}$:1, $2.5 \times 10^{-4}$:1, or $1 \times 10^{-4}$:1; a reaction zone zirconium of the zirconium compound to ethylene molar ratio ranging from $5 \times 10^{-7}$:1 to $1 \times 10^{-4}$:1, $1 \times 10^{-6}$:1 to $2.5 \times 10^{-4}$:1, $5 \times 10^{-5}$:1 to $5 \times 10^{-4}$:1, or $2.5 \times 10^{-5}$:1 to $7.5 \times 10^{-4}$:1; among other reaction zone zirconium of the zirconium compound to ethylene molar ratios and ranges).

Statement 34. The process of any one of statements 1-33, wherein the oligomer product is formed at (or the reaction zone has) any pressure described herein (e.g., a minimum pressure of 100 psi (689 kPa), 250 psi (1.72 MPa), 500 psi (3.45 MPa), 750 psi (5.17 MPa), 900 psi (6.21 MPa), or 1000 psi (6.89 MPa); a maximum pressure of 5000 psi (34.5 MPa), 4500 psi (31 MPa), 4,000 psi (27.6 MPa), 3500 psi (24.1 MPa), 3000 psi (20.7 MPa), 2,500 psi (17.2 MPa), 2,000 psi (13.8 MPa), 1,500 psi (10.3 MPa), 1250 psi (8.62 MPa), or 1000 psi (6.89 MPa); or a pressure in the range of from 100 psi (689 kPa) to 5000 psi (34.5 MPa), 100 psi (689 kPa) to 2,500 psi (17.2 MPa), 100 psi (689 kPa) to 1000 psi (6.89 MPa), 500 psi (3.45 MPa) to 4500 psi (31 MPa), 500 psi (3.45 MPa) to 2,500 psi (17.2 MPa), 500 psi (3.45 MPa) to 1000 psi (6.89 MPa), 750 psi (5.17 MPa) to 4500 psi (31 MPa), 900 psi (6.21 MPa) to 4,000 psi (27.6 MPa), or 1000 psi (6.89 MPa) to 3500 psi (24.1 MPa); among other pressures and pressure ranges).

Statement 35. The process of any one of statements 1-34, wherein the oligomer product is formed at (or the reaction zone has) any ethylene partial pressure described herein (e.g., a minimum ethylene partial pressure of 100 psi (689 kPa), 250 psi (1.72 MPa), 500 psi (3.45 MPa), 750 psi (5.17 MPa), 900 psi (6.21 MPa), or 1000 psi (6.89 MPa); a maximum ethylene partial pressure of 5000 psi (34.5 MPa), 4500 psi (31 MPa), 4,000 psi (27.6 MPa), 3500 psi (24.1 MPa), 3000 psi (20.7 MPa), 2,500 psi (17.2 MPa), 2,000 psi (13.8 MPa), 1,500 psi (10.3 MPa), 1250 psi (8.62 MPa), or 1000 psi (6.89 MPa); or an ethylene partial pressure in the range of from 100 psi (689 kPa) to 5000 psi (34.5 MPa), 100 psi (689 kPa) to 2,500 psi (17.2 MPa), 100 psi (689 kPa) to 1000 psi (6.89 MPa), 500 psi (3.45 MPa) to 4500 psi (31 MPa), 500 psi (3.45 MPa) to 2,500 psi (17.2 MPa), 500 psi (3.45 MPa) to 1000 psi (6.89 MPa), 750 psi (5.17 MPa) to 4500 psi (31 MPa), 900 psi (6.21 MPa) to 4,000 psi (27.6 MPa), or 1000 psi (6.89 MPa) to 3500 psi (24.1 MPa); among other ethylene partial pressures and pressure ranges).

Statement 36. The process of any one of statements 1-35, wherein the oligomer product is formed at (or the reaction zone has) any temperature described herein (e.g., a minimum temperature of 0° C., 25° C., 40° C., 50° C., 75° C., 100° C. or 125° C.; a maximum temperature of 250° C., 200° C., 150° C., 125° C., 100° C., or 90° C.; a temperature in ranging from 0° C. to 250° C., from 25° C. to 200° C., from 40° C. to 150° C., from 40° C. to 100° C., from 50° C. to 100° C., from 50° C. to 150° C., from 75° C. to 125° C., from 75° C. to 250° C., from 100° C. to 200° C., or from 100° C. to 200° C.; among other temperature values and ranges).

Statement 37. The process of any one of statements 1-36, wherein the oligomer product is formed at (or the reaction zone has) any ethylene:organic reaction medium mass ratio described herein (e.g., a minimum ethylene:organic reaction medium mass ratio of 0.5:1, 0.75:1, 1:1, 1.25:1, or 1.5:1; a maximum ethylene:organic reaction medium mass ratio of 4.5:1, 4:1, 3.5:1, 3:1, 2.5:1, or 2:1; an ethylene:organic reaction medium mass ratio ranging from 0.5:1 to 4.5:1, from 0.75:1 to 4:1, from 0.75:1 to 2:1, from 1:1 to 3:1, or from 1.5:1 to 2.5:1; among other ethylene:organic reaction medium mass ratio values and ranges).

Statement 38. The process of any one of statements 1-37, wherein the oligomer product is formed at (or the reaction zone has) any reaction zone residence time (or average reaction zone residence time) described herein (e.g., a minimum reaction zone residence time (or average reaction zone residence time) of 10 minutes, 20 minutes, or 30 minutes; a maximum reaction zone residence time (or average reaction zone residence time) of 3 hours, 2.5 hours, 2 hours, or 1.5 hours; a reaction zone residence time (or average reaction zone residence time) ranging from 10 minutes to 2.5 hours, from 20 minutes to 2 hours, from 30 minutes to 2 hours, or from 30 minutes to 1.5 hours; among other reaction zone residence time (or average reaction zone residence time) values and ranges.

Statement 39. The process of any one of statements 1-38, wherein the oligomer product can be formed at any ethylene conversion (or single pass ethylene conversion) described herein (e.g., a minimum ethylene conversion (or single pass ethylene conversion) of 30%, 35%, 40%, 45%, 50% or 55%; additionally or alternatively, a maximum ethylene conversion (or single pass ethylene conversion) of 95%, 90%, 87.5% 85%, or 80%; an ethylene conversion (or single pass ethylene conversion) ranging from 30% to 90%, from 35% to 90%, from 40% to 87.5%, from 45% to 87.5%, from 50% to 85%, or from 55% to 85%; among other ethylene conversion (or single pass ethylene conversion) values and ranges.

Statement 40. The process of any one of statements 1-39, wherein the oligomer product can have any Schulz-Flory K value disclosed herein (e.g., a minimum Schulz-Flory K value of 0.4, 0.45, 0.5, or 0.55; a maximum Schulz-Flory K value of 0.9, 0.85, 0.8, 0.75, 0.7, or 0.65; a Schulz-Flory K ranging from 0.4 to 0.9, from 0.4 to 0.8, from 0.5 to 0.8, from 0.5 to 0.7, or from 0.55 to 0.7; among other Schulz-Flory K values and ranges.

Statement 41. The process of any one of statements 1-40, wherein the process produces an oligomer product comprising (a) polymer having a lower Mw, (b) a polymer having a lower Mw maximum peak, (c) a reduced percentage of polymer, (d) a polymer having a reduced percentage of polymer having a Mw greater than 100,000, or (e) any combination thereof relative to the same process not using a) the chain transfer agent comprising a compound having a hydrogen silicon bond, a compound having a hydrogen sulfur bond, a compound having a hydrogen phosphorus bond, or any combination thereof in any one of statements 1-4, 2) hydrogen in any one statements 5-7, and/or 3) the transition metal compound chain transfer agent in any one of statements 8-13.

Statement 42. The process of any one of statements 1-41, wherein the oligomer product comprises (a) less than 1 wt.

% of polymer, (b) less than 1 wt. % compounds having a weight average molecular weight of greater than 1000 g/mol, or (c) any combination thereof wherein the wt. % is based on the total weight of the oligomer product.

All publications and patents mentioned herein are incorporated herein by reference. The publications and patents mentioned herein can be utilized for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

We claim:

1. A process comprising:
   a) contacting
      i) ethylene,
      ii) a catalyst system comprising
         1) a zirconium compound having the formula $ZrX^1_m Y^1_q$, where each $X^1$ independently is a halide, each $Y^1$ independently is a hydrocarboxide, a dihydrocarbylazanide, a hydrocarbylcarboxylate, a hydrocarbylsulfonate, or a β-diketonate, m is in a range from 0 to 4, q is in a range from 0 to 4, and m+q is an integer from 2 to 4, and
         2) a hydrocarbylmetal compound,
      iii) a chain transfer agent comprising a compound having a hydrogen silicon bond, a compound having a hydrogen sulfur bond, a compound having a hydrogen phosphorus bond, or any combination thereof, and
      iv) optionally, an organic reaction medium; and
   b) forming an oligomer product in a reaction zone; and
   wherein the oligomer product has a Schulz-Flory K value from 0.4 to 0.8.

2. The process of claim 1, wherein the chain transfer agent comprises a compound having the formula $R^{31}SiH_3$, $(R^{31})_2SiH_2$, $(R^{31})_3SiH$, $R^{31}OSiH_3$, $(R^{31}O)_2SiH_2$, $(R^{31}O)_3SiH$, $R^{32}SH$, $R^{32}CO_2CH_2SH$, $R^{32}CO_2CH_2CH_2SH$, $R^{33}PH_2$, $(R^{33})_2PH$, $R^{33}OPH_2$, $(R^{33}O)_2PH$, or any combination thereof, wherein each $R^{31}$, $R^{32}$, and $R^{33}$ independently is a $C_1$ to $C_{15}$ hydrocarbyl group.

3. The process of claim 1, wherein the reaction zone has a chain transfer agent to ethylene mole ratio in a range from $1\times10^{-5}:1$ to $5\times10^{-1}:1$.

4. The process of claim 1, wherein the oligomer product comprises (a) less than 1 wt. % of polymer, (b) less than 1 wt. % compounds having a weight average molecular weight of greater than 1000 g/mol, or (c) any combination thereof, wherein the wt. % is based on the total weight of the oligomer product.

5. The process of claim 1, wherein the process produces an oligomer product comprising (a) polymer having a lower Mw, (b) a polymer having a lower Mw maximum peak, (c) a reduced percentage of polymer, (d) a polymer having a reduced percentage of polymer having a Mw greater than 100,000 g/mol, or (e) any combination thereof, relative to the same process not using the chain transfer agent comprising a compound having a hydrogen silicon bond, a compound having a hydrogen sulfur bond, a compound having a hydrogen phosphorus bond, or any combination thereof.

6. The process of claim 1, wherein the hydrocarbylmetal compound has the formula $AlX^2_{3-n}R^1_n$, $Al_2X^2_{6-q}R^1_q$, $R^1_2Zn$, or any combination thereof, wherein each $R^1$ independently is a $C_1$ to $C_{10}$ alkyl group, each $X^2$ independently is chloride, bromide, or iodide, n is an integer from 0 to 3, and q is an integer for 0 to 6.

7. The process of claim 1, wherein the catalyst system further comprises a neutral non-ionic organic modifier.

8. The process of claim 7, wherein the neutral non-ionic organic modifier comprises an ether, an ester, a ketone, an aldehyde, an alcohol, an anhydride, an acid chloride, a nitrile, a sulfide, a disulfide, a phosphine, an amine, or an amide.

9. The process of claim 1, wherein the zirconium compound has the formula $ZrX^1_m$ where each $X^1$ independently is chloride or bromide and m is 4, and wherein the hydrocarbylmetal compound has the formula $AlX^2_n R^1_{3-n}$, $Al_2X^2_3 R^1_3$, $R^1_2Zn$, or any combination thereof, wherein each $X^2$ independently is a halide and each $R^1$ independently is $C_2$ to $C_4$ alkyl group.

10. The process of claim 9, wherein the catalyst system further comprises a $C_2$ to $C_{20}$ ester, a $C_2$ to $C_{20}$ ether, or a $C_2$ to $C_{20}$ sulfide as a neutral non-ionic organic modifier.

11. The process of claim 1, wherein the zirconium compound has the formula $ZrY^1_q$ where each $Y^1$ independently is $^-OR^2$, wherein $R^2$ is a $C_1$ to $C_{10}$ alkyl group or $^-OC(=O)R^3$, wherein $R^3$ is a $C_1$ to $C_{10}$ alkyl group and q is an integer from 2 to 4, and wherein the hydrocarbylmetal compound has the formula $AlX^3_n R^1_{3-n}$, $Al_2X^3_3 R^1_3$, or any combination thereof, wherein each $X^2$ independently is a halide and each $R^1$ independently is $C_2$ to $C_4$ alkyl group.

* * * * *